United States Patent
Xu et al.

(10) Patent No.: US 12,421,240 B2
(45) Date of Patent: Sep. 23, 2025

(54) HYDROPYRAZINO[1,2-D][1,4]DIAZEPINE COMPOUNDS FOR THE TREATMENT OF AUTOIMMUNE DISEASE

(71) Applicant: Hoffmann-La Roche Inc., Little Falls, NJ (US)

(72) Inventors: Hongtao Xu, Shanghai (CN); Zhisen Zhang, Shanghai (CN); Wei Zhu, Shanghai (CN); Ge Zou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 663 days.

(21) Appl. No.: 17/772,930

(22) PCT Filed: Oct. 29, 2020

(86) PCT No.: PCT/EP2020/080430
§ 371 (c)(1),
(2) Date: Apr. 28, 2022

(87) PCT Pub. No.: WO2021/084022
PCT Pub. Date: May 6, 2021

(65) Prior Publication Data
US 2023/0034723 A1    Feb. 2, 2023

(30) Foreign Application Priority Data

Oct. 31, 2019  (WO) ................ PCT/CN2019/114755

(51) Int. Cl.
*C07D 487/04*   (2006.01)
*A61P 37/00*    (2006.01)
*C07D 519/00*   (2006.01)

(52) U.S. Cl.
CPC ......... *C07D 487/04* (2013.01); *C07D 519/00* (2013.01)

(58) Field of Classification Search
CPC ...... C07D 487/04; C07D 519/00; A61P 37/00
See application file for complete search history.

(56) References Cited

U.S. PATENT DOCUMENTS

| | | |
|---|---|---|
| 7,642,350 B2 | 1/2010 | Pryde |
| 8,163,738 B2 | 4/2012 | Doherty et al. |
| 8,729,088 B2 | 5/2014 | Carson et al. |
| 10,544,143 B2 | 1/2020 | Dyckman et al. |
| 2012/0083473 A1 | 4/2012 | Holldack et al. |
| 2014/0088085 A1 | 3/2014 | Burgess et al. |
| 2015/0105370 A1 | 4/2015 | Carlson et al. |
| 2017/0008885 A1 | 1/2017 | Koul et al. |
| 2017/0174653 A1 | 6/2017 | Sherer et al. |
| 2018/0037570 A1 | 2/2018 | Sherer et al. |
| 2019/0185469 A1 | 6/2019 | Dyckman et al. |
| 2020/0325142 A1 | 10/2020 | Chakravarty et al. |
| 2022/0340597 A1 | 10/2022 | Zhu et al. |
| 2023/0022297 A1 | 1/2023 | Chen et al. |
| 2023/0219959 A1 | 7/2023 | Chen et al. |

FOREIGN PATENT DOCUMENTS

| | | | |
|---|---|---|---|
| CL | 2014003278 A1 | 6/2015 | |
| CL | 2016000662 A1 | 12/2016 | |
| CL | 2018001624 A1 | 9/2018 | |
| CL | 2021002521 A1 | 4/2022 | |
| CN | 108794485 A | 11/2018 | |
| WO | 2012/084704 A1 | 6/2012 | |
| WO | 2012/097177 A2 | 7/2012 | |
| WO | 2013/181579 A2 | 12/2013 | |
| WO | 2015/057659 A1 | 4/2015 | |
| WO | 2015/057655 A1 | 5/2015 | |
| WO | 2015/088045 A1 | 6/2015 | |
| WO | 2017/081111 A1 | 5/2017 | |
| WO | WO-2017106607 A1 * | 6/2017 | ......... A61K 31/4375 |
| WO | 2018/005586 A1 | 1/2018 | |
| WO | 2018/026620 A1 | 2/2018 | |
| WO | 2018/031434 A1 | 2/2018 | |
| WO | 2018/047081 A1 | 3/2018 | |

(Continued)

OTHER PUBLICATIONS

Devarapu, S. K. & Anders, H. J. J. Biomed. Sci. 2018, 25:35 (Year: 2018).*
"International Preliminary Report on Patentability—PCT/EP2020/080430" (Report Issuance Date: May 3, 2022; Chapter I), :pp. 1-8 (May 12, 2022).
"International Search Report—PCT/EP2020/080430" (w/Written Opinion), :pp. 1-11 (Dec. 23, 2020).
Alper, P., et al., "Discovery of potent, orally bioavailable in vivo efficacious antagonists of the TLR7/8 pathway" Bioorg Med Chem Lett 30(17):127366 (1-5)(Sep. 1, 2020).
Barrat, F., et al., "Treatment of lupus-prone mice with a dual inhibitor of TLR7 and TLR9 leads to reduction of autoantibody production and amelioration of disease symptoms" Eur J Immunol (EPUB: Nov. 29, 2007), 37(12):3582-3586 (Dec. 1, 2007).

(Continued)

*Primary Examiner* — Clinton A Brooks
*Assistant Examiner* — Kendall Nicole Heitmeier
(74) *Attorney, Agent, or Firm* — Bradley E. Davis

(57) ABSTRACT

The present invention relates to compounds of formula (I), wherein $R^1$ and $R^3$ and n are as described herein, and their pharmaceutically acceptable salt thereof, and compositions including the compounds and methods of using the compounds.

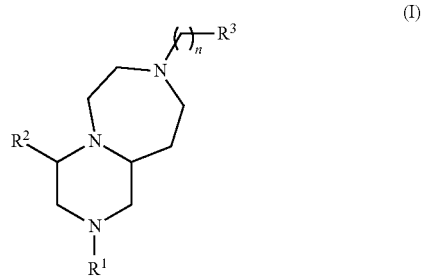

(I)

16 Claims, No Drawings

(56) References Cited

FOREIGN PATENT DOCUMENTS

| | | |
|---|---|---|
| WO | 2018/049089 A1 | 3/2018 |
| WO | 2018/232274 A1 | 12/2018 |
| WO | 2019/018354 A1 | 1/2019 |
| WO | 2019/028301 A1 | 2/2019 |
| WO | 2019/028302 A1 | 2/2019 |
| WO | 2019/099336 A1 | 5/2019 |
| WO | 2019/118799 A1 | 6/2019 |
| WO | 2019/123294 A2 | 6/2019 |
| WO | 2019/125849 A1 | 6/2019 |
| WO | 2019/126081 A1 | 6/2019 |
| WO | 2019/126082 A1 | 6/2019 |
| WO | 2019/126083 A1 | 6/2019 |
| WO | 2019/126113 A1 | 6/2019 |
| WO | 2019/126242 A1 | 6/2019 |
| WO | 2019/126253 A1 | 6/2019 |
| WO | 2019/220390 A1 | 11/2019 |
| WO | 2019/233941 A1 | 12/2019 |
| WO | 2019/238629 A1 | 12/2019 |
| WO | 2020/020800 A1 | 1/2020 |
| WO | 2020/064792 A1 | 4/2020 |
| WO | 2020/207991 A1 | 10/2020 |
| WO | 2021/084022 A1 | 5/2021 |
| WO | 2021/099284 A1 | 5/2021 |
| WO | 2021/110614 A1 | 6/2021 |

OTHER PUBLICATIONS

Devarapu, S et al., "Toll-like receptors in lupus nephritis" Journal of Biomedical Science:1-11 (2018).

Horig, H., et al., "From bench to clinic and back: Perspective on the 1st IQPC Translational Research conference" J Transl Med 2:44-44 (Dec. 20, 2004).

"International Preliminary Report on Patentability—PCT/EP2020/082316" (Report Issuance Date: May 17, 2022; Chapter I),:pp. 1-8 (Jun. 2, 2022).

"International Preliminary Report on Patentability—PCT/EP2020/083996" (Report Issuance Date: May 17, 2022; Chapter I),:pp. 1-10 (Jun. 16, 2022).

"International Preliminary Report on Patentability—PCT/EP2020/059831" (Report Issuance Date: Sep. 28, 2021, Chapter I),: 1-8 (Oct. 21, 2021).

"International Search Report—PCT/EP2020/059831" (w/Written Opinion),:pp. 1-12 (Jun. 3, 2020).

"International Search Report—PCT/EP2020/082316" (w/Written Opinion),:pp. 1-13 (Dec. 16, 2020).

"International Search Report—PCT/EP2020/083996" (w/Written Opinion),:pp. 1-17 (Feb. 19, 2021).

Knoepfel, T., et al., "Target-Based Identification and Optimization of 5-Indazol-5-yl Pyridones as Toll-like Receptor 7 and 8 Antagonists Using a Biochemical TLR8 Antagonist Competition Assay" J Med Chem 63(15):8276-8295 (Jul. 30, 2020).

Mussari, C., et al., "Discovery of Potent and Orally Bioavailable Small Molecule Antagonists of Toll-like Receptors 7/8/9 (TLR7/8/9)" ACS Med Chem Lett 11(9):1751-1758 (Jul. 29, 2020).

"PubChem CID 5234, National Center for Biotechnology Information. PubChem Compound Summary for CID 5234, Sodium Chloride. https://pubchem.ncbi.nlm.nih.gov/compound/Sodium-Chloride. Accessed Apr. 25, 2025 (Year: 2005)".

Schafer, S. et al., "Failure is an option: learning from unsuccessful proof-of-concept trials" Drug Discov Today (EPUB: Jun. 17, 2008), 13(21-22): 913-916 (Nov. 1, 2008).

\* cited by examiner

HYDROPYRAZINO[1,2-D][1,4]DIAZEPINE COMPOUNDS FOR THE TREATMENT OF AUTOIMMUNE DISEASE

CROSS-REFERENCE TO RELATED APPLICATIONS

This application is a National Stage Entry under 35 U.S.C. § 371 of International Application No. PCT/EP2020/080430, filed Oct. 29, 2020, which claims benefit of priority to Chinese Application No. PCT/CN2019/114755 filed Oct. 31, 2019, each of which is incorporated herein by reference in its entirety.

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with non-specific anti-inflammatory or immunosuppressive drugs. However, long-term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al Lancet 2011, 377, 721.). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many autoimmune as well as autoinflammation diseases.

Toll like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7, 8, 9 is considered as a key node in a broad of autoimmune and auto-inflammatory diseases (Krieg, A. M. et al. Immunol. Rev. 2007, 220, 251. Jiménez-Dalmaroni, M. J. et al Autoimmun Rev. 2016, 15, 1. Chen, J. Q., et al. Clinical Reviews in Allergy & Immunology 2016, 50, 1.). Anti-RNA and anti-DNA antibodies are well-established diagnostic markers of SLE, and these antibodies can deliver both self-RNA and self-DNA to endosomes. While self-RNA complexes can be recognized by TLR7 and TLR8, self-DNA complexes can trigger TLR9 activation. Indeed, defective clearance of self-RNA and self-DNA from blood and/or tissues is evident in SLE (Systemic Lupus Erythematosus) patients. TLR7 and TLR9 have been reported to be upregulated in SLE tissues, and correlate with chronicity and activity of lupus nephritis, respectively. In B cells of SLE patients, TLR7 expression correlates with anti-RNP antibody production, while TLR9 expression with IL-6 and anti-dsDNA antibody levels. Consistently, in lupus mouse models, TLR7 is required for anti-RNA antibodies, and TLR9 is required for anti-nucleosome antibody. On the other hand, overexpression of TLR7 or human TLR8 in mice promotes autoimmunity and auto-inflammation. Moreover, activation of TLR8 specifically contributes to inflammatory cytokine secretion of mDC/macrophages, neutrophil NETosis, induction of Th17 cells, and suppression of Treg cells. In addition to the described role of TLR9 in promoting autoantibody production of B cells, activation of TLR9 by self-DNA in pDC also leads to induction of type I IFNs and other inflammatory cytokines. Given these roles of TLR9 in both pDC and B cells, both as key contributors to the pathogenesis of autoimmune diseases, and the extensive presence of self-DNA complexes that could readily activate TLR9 in many patients with autoimmune diseases, it may have extra benefit to further block self-DNA mediated TLR9 pathways on top of inhibition of TLR7 and TLR8 pathways. Taken together, TLR7, 8 and 9 pathways represent new therapeutic targets for the treatment of autoimmune and auto-inflammatory diseases, for which no effective steroid-free and non-cytotoxic oral drugs exist, and inhibition of all these pathways from the very upstream may deliver satisfying therapeutic effects. As such, we invented oral compounds that target and suppress TLR7, TLR8 and TLR9 for the treatment of autoimmune and auto-inflammatory diseases.

SUMMARY OF THE INVENTION

The present invention relates to novel compounds of formula (I) or (Ia),

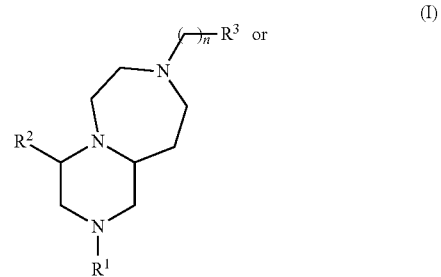

(I)

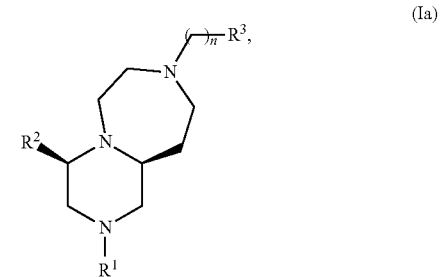

(Ia)

wherein
R¹ is

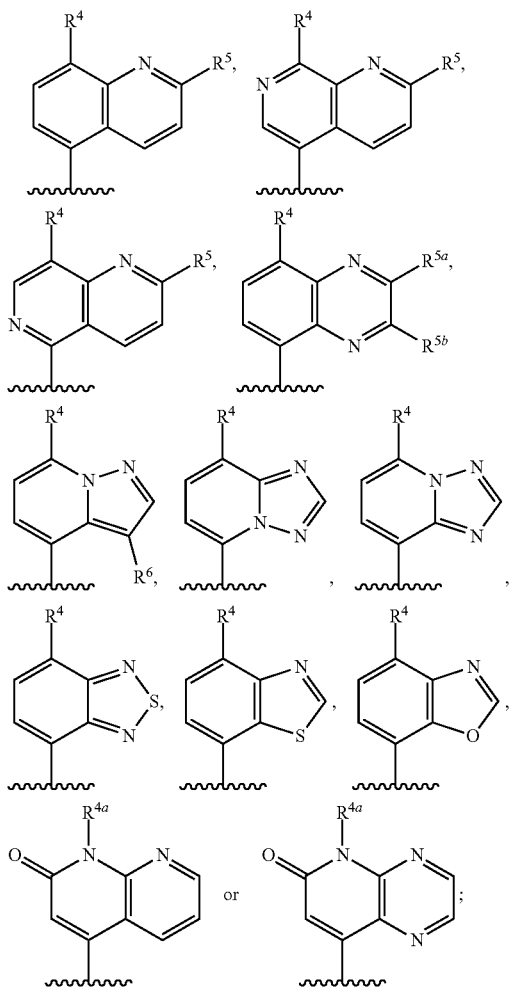

wherein R⁴ is $C_{1-6}$alkyl, $C_{1-6}$alkoxy, halo$C_{1-6}$alkyl, halogen, nitro or cyano; R⁴ᵃ is $C_{1-6}$alkyl or $C_{3-7}$cycloalkyl;

R⁵, R⁵ᵃ and R⁵ᵇ are independently selected from H and deuterium; R⁶ is H or halogen; R² is $C_{1-6}$alkyl;

R³ is a 5-7 membered monocyclic aryl or heteroaryl; or a 7-12 membered bicyclic heterocyclyl;

n is 0, 1 or 2;

or a pharmaceutically acceptable salt thereof.

Another object of the present invention is related to novel compounds of formula (I) or (Ia). Their manufacture, medicaments based on a compound in accordance with the invention and their production as well as the use of compounds of formula (I) or (Ia) as TLR7 and/or TLR8 and/or TLR9 antagonist, and for the treatment or prophylaxis of systemic lupus erythematosus or lupus nephritis. The compounds of formula (I) or (Ia) show superior TLR7 and TLR8 and TLR9 antagonism activity. In addition, the compounds of formula (I) or (Ia) also show good cytotoxicity, phototoxicity, solubility, hPBMC, human microsome stability and SDPK profiles, as well as low CYP inhibition.

DETAILED DESCRIPTION OF THE INVENTION

Definitions

The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "halogen" and "halo" are used interchangeably herein and denote fluoro, chloro, bromo, or iodo.

The term "halopyrrolidinyl" denotes a pyrrolidinyl substituted once, twice or three times by halogen. Examples of halopyrrolidinyl include, but not limited to, difluoropyrrolidinyl and fluoropyrrolidinyl.

The term "aryl" denotes an aromatic hydrocarbon mono- or bicyclic ring system of 5 to 12 ring atoms. Examples of aryl include, but not limited to, phenyl and naphthyl. Aryl can be further substituted by substituents includes, but not limited to $C_{1-6}$alkyl; 3,4,4a,5,7,7a-hexahydro-2H-pyrrolo[3,4-b][1,4]oxazinyl; 1,4-diazepanyl; 2,6-diazaspiro[3.3]heptanyl substituted by $C_{1-6}$alkyl; 5-oxa-2,8-diazaspiro[3.5]nonanyl; amino-1,4-oxazepanyl; azetidinyl substituted by one or two substituents independently selected from amino and $C_{1-6}$alkyl; piperazinyl unsubstituted or substituted by $C_{1-6}$alkyl; and pyrrolidinyl substituted by one or two substituents independently selected from amino, $C_{1-6}$alkoxy and halogen.

The term "heteroaryl" denotes an aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include, but not limited to, pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl or quinoxalinyl. Heteroaryl can be further substituted by substituents include, but not limited to $C_{1-6}$alkyl; 3,4,4a,5,7,7a-hexahydro-2H-pyrrolo[3,4-b][1,4]oxazinyl; 1,4-diazepanyl; 2,6-diazaspiro[3.3]heptanyl substituted by $C_{1-6}$alkyl; 5-oxa-2,8-diazaspiro[3.5]nonanyl; amino-1,4-oxazepanyl; azetidinyl substituted by one or two substituents independently selected from amino and $C_{1-6}$alkyl; piperazinyl unsubstituted or substituted by $C_{1-6}$alkyl; and pyrrolidinyl substituted by one or two substituents independently selected from amino, $C_{1-6}$alkoxy and halogen.

The term "heterocyclyl" or "heterocyclic" denotes a monovalent saturated or partly unsaturated mono or bicyclic ring system of 3 to 12 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl.

Examples for bicyclic saturated heterocyclic ring are azabicyclo[3.2.1]octyl, quinuclidinyl, oxaazabicyclo[3.2.1]octanyl, azabicyclo[3.3.1]nonanyl, oxaaza-bicyclo[3.3.1]nonanyl, azabicyclo[3.1.0]hexanyl, oxodiazaspiro[3.4]octanyl, acetyloxodiazaspiro[3.4]octanyl, thiaazabicyclo[3.3.1]nonanyl, oxoazaspiro[2.4]heptanyl, oxoazaspiro[3.4]octanyl, oxoazabicyclo[3.1.0]hexanyl and dioxotetrahydropyrrolo[1,2-a]pyrazinyl. Examples for bicyclic heterocyclyl include, but not limited to, 1,2,3,4-tetrahydroisoquinolinyl; 5,6,7,8-tetrahydro-1,6-naphthyridinyl; 5,6,7,8-tetrahydro-1,7-naphthyridinyl; 5,6,7,8-tetrahydro-2,6-naphthyridinyl; 5,6,7,8-tetrahydro-2,7-naphthyridinyl; isoindolinyl.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to (i) a compound of formula (I),

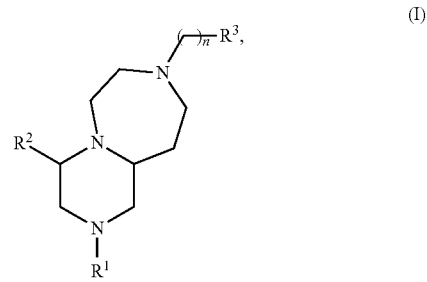

wherein

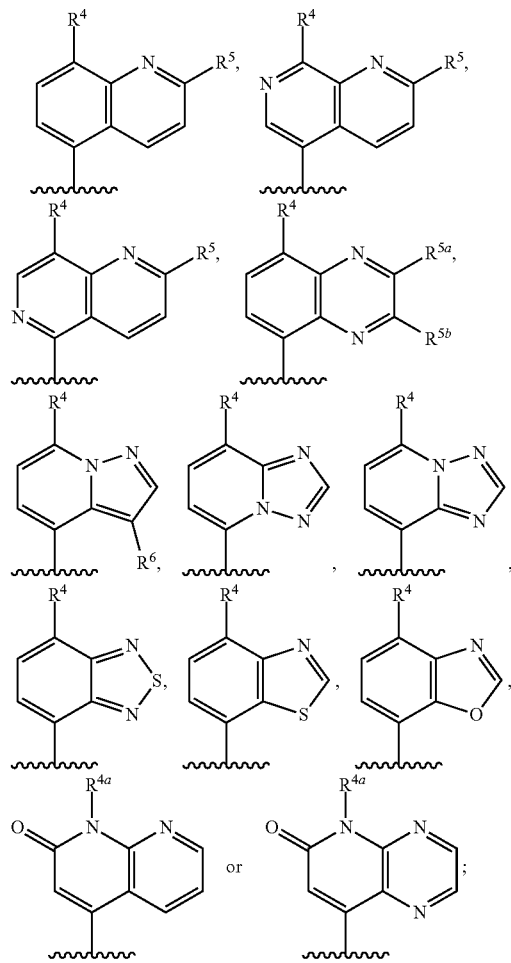

R[1] is wherein R[4] is $C_{1-6}$alkyl, $C_{1-6}$alkoxy, halo$C_{1-6}$alkyl, halogen, nitro or cyano; R[4a] is $C_{1-6}$alkyl or $C_{3-7}$cycloalkyl; R[5], R[5a] and R[5b] are independently selected from H and deuterium; R[6] is H or halogen;

R[2] is $C_{1-6}$alkyl;

R[3] is a 5-7 membered monocyclic aryl or heteroaryl; or a 7-12 membered bicyclic heterocyclyl;

n is 0, 1 or 2;

or a pharmaceutically acceptable salt thereof.

Further embodiment of present invention is (ii) a compound of formula (I) according to (i), wherein R[3] is 1,2,3,4-tetrahydroisoquinolinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl;
5,6,7,8-tetrahydro-2,7-naphthyridinyl;
phenyl substituted by morpholinyl;
pyrazinyl substituted by piperazinyl;
pyridinyl which is substituted by one or two substituents independently selected from halogen, piperazinyl, aminohalopyrrolidinyl, amino-1,4-oxazepanyl and amino($C_{1-6}$alkoxy)pyrrolidinyl; or
pyrimidinyl substituted by piperazinyl or amino($C_{1-6}$alkoxy)pyrrolidinyl.

Another embodiment of present invention is (iii) a compound of formula (Ia),

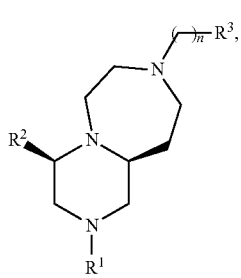

wherein

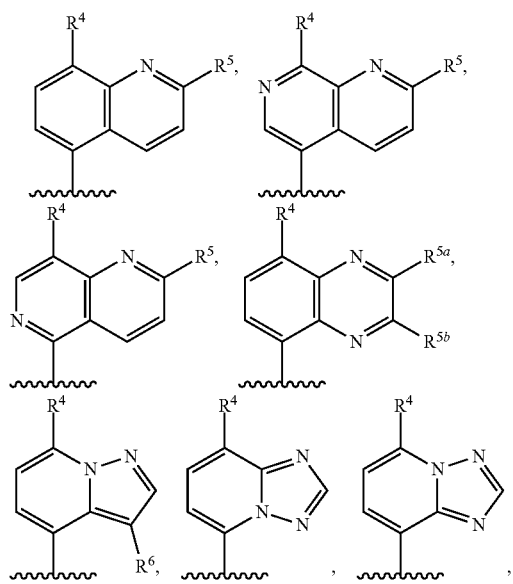

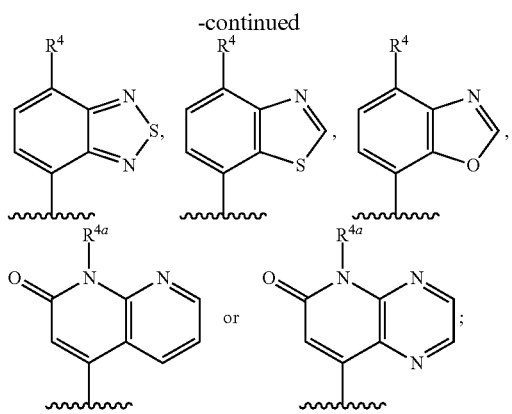

R[1] is wherein R[4] is $C_{1-6}$alkyl, $C_{1-6}$alkoxy, halo$C_{1-6}$alkyl, halogen, nitro or cyano; R[4a] is $C_{1-6}$alkyl or $C_{3-7}$cycloalkyl; R[5], R[5a] and R[5b] are independently selected from H and deuterium; R[6] is H or halogen;

R[2] is $C_{1-6}$alkyl;

R[3] is 1,2,3,4-tetrahydroisoquinolinyl;

5,6,7,8-tetrahydro-1,6-naphthyridinyl;

5,6,7,8-tetrahydro-1,7-naphthyridinyl;

5,6,7,8-tetrahydro-2,6-naphthyridinyl;

5,6,7,8-tetrahydro-2,7-naphthyridinyl;

phenyl substituted by morpholinyl;

pyrazinyl substituted by piperazinyl;

pyridinyl which is substituted by one or two substituents independently selected from halogen, piperazinyl, aminohalopyrrolidinyl, amino-1,4-oxazepanyl and amino($C_{1-6}$alkoxy)pyrrolidinyl; or pyrimidinyl substituted by piperazinyl or amino($C_{1-6}$alkoxy)pyrrolidinyl;

n is 0, 1 or 2;

or a pharmaceutically acceptable salt thereof.

A further embodiment of present invention is (iv) a compound of formula (I) or (Ia), or a pharmaceutically acceptable salt thereof, according to any one of (i) to (iii), wherein R[1] is

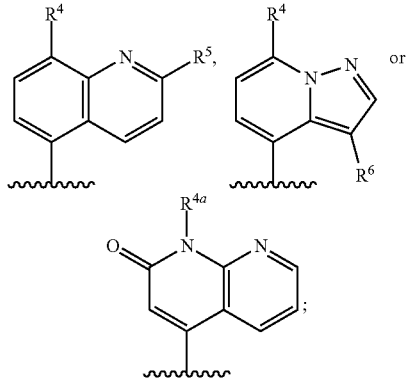

wherein R[4] is cyano; R[4a] is $C_{1-6}$alkyl; R[5] is H; R[6] is H or halogen; and n is 0 or 1.

A further embodiment of present invention is (v) a compound of formula (I) or (Ia) according to any one of (i) to (iv), wherein
R¹ is

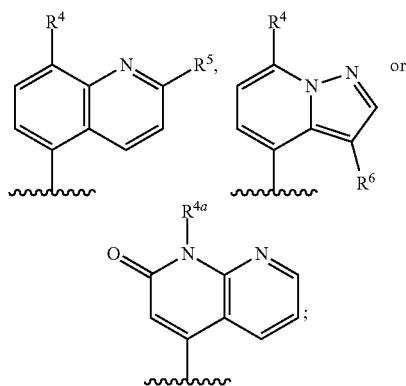

wherein R⁴ is cyano; R⁴ᵃ is methyl; R⁵ is H; R⁶ is H or fluoro;

R² is methyl;

R³ is 1,2,3,4-tetrahydroisoquinolin-6-yl;
1,2,3,4-tetrahydroisoquinolin-7-yl;
5,6,7,8-tetrahydro-1,6-naphthyridin-2-yl;
5,6,7,8-tetrahydro-1,6-naphthyridin-3-yl;
5,6,7,8-tetrahydro-1,7-naphthyridin-2-yl;
5,6,7,8-tetrahydro-2,6-naphthyridin-3-yl;
5,6,7,8-tetrahydro-2,7-naphthyridin-3-yl;
5,6,7,8-tetrahydro-2,7-naphthyridin-4-yl;
morpholin-2-ylphenyl;
piperazin-1-ylpyrazinyl;
pyridinyl which is substituted by one or two substituents independently selected from fluoro, piperazin-1-yl, 3-amino-4-fluoro-pyrrolidin-1-yl, 6-amino-1,4-oxazepan-4-yl and 3-amino-4-methoxy-pyrrolidin-1-yl; or
pyrimidinyl substituted by piperazin-1-yl or 3-amino-4-methoxy-pyrrolidin-1-yl;

n is 0 or 1;

or a pharmaceutically acceptable salt thereof.

A further embodiment of present invention is (vi) a compound of formula (I) or (Ia), or a pharmaceutically acceptable salt thereof, according to any one of (i) to (v), wherein R¹ is

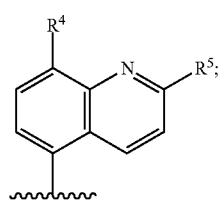

wherein R⁴ is cyano; R⁵ is H.

A further embodiment of present invention is (vii) a compound of formula (I) or (Ia), or a pharmaceutically acceptable salt thereof, according to any one of (i) to (vi), wherein R³ is 5,6,7,8-tetrahydro-2,6-naphthyridinyl; 5,6,7,8-tetrahydro-2,7-naphthyridinyl; pyridinyl substituted by amino($C_{1-6}$alkoxy)pyrrolidinyl; or pyrimidinyl substituted by piperazinyl.

A further embodiment of present invention is (viii) a compound of formula (I) or (Ia), or a pharmaceutically acceptable salt thereof, according to any one of (i) to (vii), wherein R³ is 5,6,7,8-tetrahydro-2,7-naphthyridin-4-yl; 5,6,7,8-tetrahydro-2,6-naphthyridin-3-yl; piperazin-1-ylpyrimidinyl; or 3-amino-4-methoxy-pyrrolidin-1-ylpyridinyl.

A further embodiment of present invention is (ix) a compound of formula (I) or (Ia), or a pharmaceutically acceptable salt thereof, according to any one of (i) to (viii), wherein
R¹ is

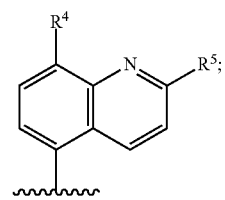

wherein R⁴ is cyano; R⁵ is H;

R² is $C_{1-6}$alkyl;

R³ is 5,6,7,8-tetrahydro-2,6-naphthyridinyl; 5,6,7,8-tetrahydro-2,7-naphthyridinyl; pyridinyl substituted by amino($C_{1-6}$alkoxy)pyrrolidinyl; or pyrimidinyl substituted by piperazinyl;

n is 0 or 1;

or a pharmaceutically acceptable salt thereof.

A further embodiment of present invention is (x) a compound of formula (I) or (Ia), or a pharmaceutically acceptable salt thereof, according to any one of (i) to (ix), wherein
R¹ is

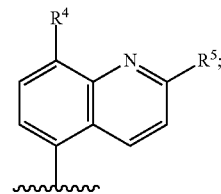

wherein R⁴ is cyano; R⁵ is H;

R² is methyl;

R³ is 5,6,7,8-tetrahydro-2,7-naphthyridin-4-yl;5,6,7,8-tetrahydro-2,6-naphthyridin-3-yl; piperazin-1-ylpyrimidinyl; or 3-amino-4-methoxy-pyrrolidin-1-ylpyridinyl;

n is 0 or 1;

or a pharmaceutically acceptable salt thereof.

Another embodiment of present invention is a compound of formula (I) or (Ia) selected from the following:

- 5-[(4R,10aS)-4-methyl-8-(6-piperazin-1-yl-3-pyridyl)-1,3,4,6,7,9,10,10a-octahydropyrazino[1,2-d][1,4]diazepin-2-yl]quinoline-8-carbonitrile;
- 5-[(4R,10aS)-4-methyl-8-(2-piperazin-1-ylpyrimidin-5-yl)-1,3,4,6,7,9,10,10a-octahydropyrazino[1,2-d][1,4]diazepin-2-yl]quinoline-8-carbonitrile;
- 5-[(4R,10aS)-4-methyl-8-[4-[(2S)-morpholin-2-yl]phenyl]-1,3,4,6,7,9,10,10a-octahydropyrazino[1,2-d][1,4]diazepin-2-yl]quinoline-8-carbonitrile;
- 5-[(4R,10aS)-4-methyl-8-(5,6,7,8-tetrahydro-2,7-naphthyridin-4-yl)-1,3,4,6,7,9,10,10a-octahydropyrazino[1,2-d][1,4]diazepin-2-yl]quinoline-8-carbonitrile;
- 5-[(4R,10aS)-4-methyl-8-(5,6,7,8-tetrahydro-1,7-naphthyridin-2-yl)-1,3,4,6,7,9,10,10a-octahydropyrazino[1,2-d][1,4]diazepin-2-yl]quinoline-8-carbonitrile;
- 5-[(4R,10aS)-4-methyl-8-(5,6,7,8-tetrahydro-1,6-naphthyridin-2-yl)-1,3,4,6,7,9,10,10a-octahydropyrazino[1,2-d][1,4]diazepin-2-yl]quinoline-8-carbonitrile;
- 5-[(4R,10aS)-4-methyl-8-(5,6,7,8-tetrahydro-2,7-naphthyridin-3-yl)-1,3,4,6,7,9,10,10a-octahydropyrazino[1,2-d][1,4]diazepin-2-yl]quinoline-8-carbonitrile;
- 5-[(4R,10aS)-4-methyl-8-(5,6,7,8-tetrahydro-2,7-naphthyridin-3-ylmethyl)-1,3,4,6,7,9,10,10a-octahydropyrazino[1,2-d][1,4]diazepin-2-yl]quinoline-8-carbonitrile;
- 5-[(4R,10aS)-4-methyl-8-(5,6,7,8-tetrahydro-2,6-naphthyridin-3-ylmethyl)-1,3,4,6,7,9,10,10a-octahydropyrazino[1,2-d][1,4]diazepin-2-yl]quinoline-8-carbonitrile;
- 5-[(4R,10aS)-4-methyl-8-(5,6,7,8-tetrahydro-1,6-naphthyridin-3-ylmethyl)-1,3,4,6,7,9,10,10a-octahydropyrazino[1,2-d][1,4]diazepin-2-yl]quinoline-8-carbonitrile;
- 5-[(4R,10aS)-4-methyl-8-(1,2,3,4-tetrahydroisoquinolin-6-ylmethyl)-1,3,4,6,7,9,10,10a-octahydropyrazino[1,2-d][1,4]diazepin-2-yl]quinoline-8-carbonitrile;
- 5-[(4R,10aS)-4-methyl-8-(1,2,3,4-tetrahydroisoquinolin-7-ylmethyl)-1,3,4,6,7,9,10,10a-octahydropyrazino[1,2-d][1,4]diazepin-2-yl]quinoline-8-carbonitrile;
- 5-[(4R,10aS)-4-methyl-8-[(5-piperazin-1-ylpyrimidin-2-yl)methyl]-1,3,4,6,7,9,10,10a-octahydropyrazino[1,2-d][1,4]diazepin-2-yl]quinoline-8-carbonitrile;
- 5-[(4R,10aS)-4-methyl-8-[(2-piperazin-1-ylpyrimidin-5-yl)methyl]-1,3,4,6,7,9,10,10a-octahydropyrazino[1,2-d][1,4]diazepin-2-yl]quinoline-8-carbonitrile;
- 5-[(4R,10aS)-4-methyl-8-[(5-piperazin-1-ylpyrazin-2-yl)methyl]-1,3,4,6,7,9,10,10a-octahydropyrazino[1,2-d][1,4]diazepin-2-yl]quinoline-8-carbonitrile;
- 5-[(4R,10aS)-4-methyl-8-[(5-piperazin-1-yl-3-pyridyl)methyl]-1,3,4,6,7,9,10,10a-octahydropyrazino[1,2-d][1,4]diazepin-2-yl]quinoline-8-carbonitrile;
- 5-[(4R,10aS)-4-methyl-8-[(6-piperazin-1-yl-3-pyridyl)methyl]-1,3,4,6,7,9,10,10a-octahydropyrazino[1,2-d][1,4]diazepin-2-yl]quinoline-8-carbonitrile;
- 5-[(4R,10aS)-4-methyl-8-[(6-piperazin-1-yl-2-pyridyl)methyl]-1,3,4,6,7,9,10,10a-octahydropyrazino[1,2-d][1,4]diazepin-2-yl]quinoline-8-carbonitrile;
- 5-[(4R,10aS)-4-methyl-8-[(5-piperazin-1-yl-2-pyridyl)methyl]-1,3,4,6,7,9,10,10a-octahydropyrazino[1,2-d][1,4]diazepin-2-yl]quinoline-8-carbonitrile;
- 5-[(4R,10aS)-8-[[5-[(3R,4S)-3-amino-4-fluoro-pyrrolidin-1-yl]-2-pyridyl]methyl]-4-methyl-1,3,4,6,7,9,10,10a-octahydropyrazino[1,2-d][1,4]diazepin-2-yl]quinoline-8-carbonitrile;
- 5-[(4R,10aS)-8-[[5-[(6R)-6-amino-1,4-oxazepan-4-yl]-2-pyridyl]methyl]-4-methyl-1,3,4,6,7,9,10,10a-octahydropyrazino[1,2-d][1,4]diazepin-2-yl]quinoline-8-carbonitrile;
- 5-[(4R,10aS)-8-[[5-[(3R,4R)-3-amino-4-methoxy-pyrrolidin-1-yl]-2-pyridyl]methyl]-4-methyl-1,3,4,6,7,9,10,10a-octahydropyrazino[1,2-d][1,4]diazepin-2-yl]quinoline-8-carbonitrile;
- 5-[(4R,10aS)-8-[(3-fluoro-5-piperazin-1-yl-2-pyridyl)methyl]-4-methyl-1,3,4,6,7,9,10,10a-octahydropyrazino[1,2-d][1,4]diazepin-2-yl]quinoline-8-carbonitrile;
- 5-[(4R,10aS)-8-[[5-[(3R,4R)-3-amino-4-methoxy-pyrrolidin-1-yl]-3-fluoro-2-pyridyl]methyl]-4-methyl-1,3,4,6,7,9,10,10a-octahydropyrazino[1,2-d][1,4]diazepin-2-yl]quinoline-8-carbonitrile;
- 4-[(4R,10aS)-8-[[5-[(3R,4R)-3-amino-4-methoxy-pyrrolidin-1-yl]pyrazin-2-yl]methyl]-4-methyl-1,3,4,6,7,9,10,10a-octahydropyrazino[1,2-d][1,4]diazepin-2-yl]pyrazolo[1,5-a]pyridine-7-carbonitrile;
- 4-[(4R,10aS)-8-[[5-[(3R,4R)-3-amino-4-methoxy-pyrrolidin-1-yl]-3-fluoro-2-pyridyl]methyl]-4-methyl-1,3,4,6,7,9,10,10a-octahydropyrazino[1,2-d][1,4]diazepin-2-yl]pyrazolo[1,5-a]pyridine-7-carbonitrile;
- 4-[(4R,10aS)-8-[[5-[(3R,4R)-3-amino-4-methoxy-pyrrolidin-1-yl]-3-fluoro-2-pyridyl]methyl]-4-methyl-1,3,4,6,7,9,10,10a-octahydropyrazino[1,2-d][1,4]diazepin-2-yl]-3-fluoro-pyrazolo[1,5-a]pyridine-7-carbonitrile; and
- 4-[(4R,10aS)-4-methyl-8-(1,2,3,4-tetrahydroisoquinolin-7-ylmethyl)-1,3,4,6,7,9,10,10a-octahydropyrazino[1,2-d][1,4]diazepin-2-yl]-1-methyl-1,8-naphthyridin-2-one;

or a pharmaceutically acceptable salt thereof.

Synthesis

The compounds of the present invention can be prepared by any conventional means. Suitable processes for synthesizing these compounds as well as their starting materials are provided in the schemes below and in the examples. All substituents, in particular, $R^1$ and $R^2$ are as defined above unless otherwise indicated. Furthermore, and unless explicitly otherwise stated, all reactions, reaction conditions, abbreviations and symbols have the meanings well known to a person of ordinary skill in organic chemistry.

General synthetic routes for preparing the compound of formula (I), (VII) and (XI) are shown below.

Scheme 1

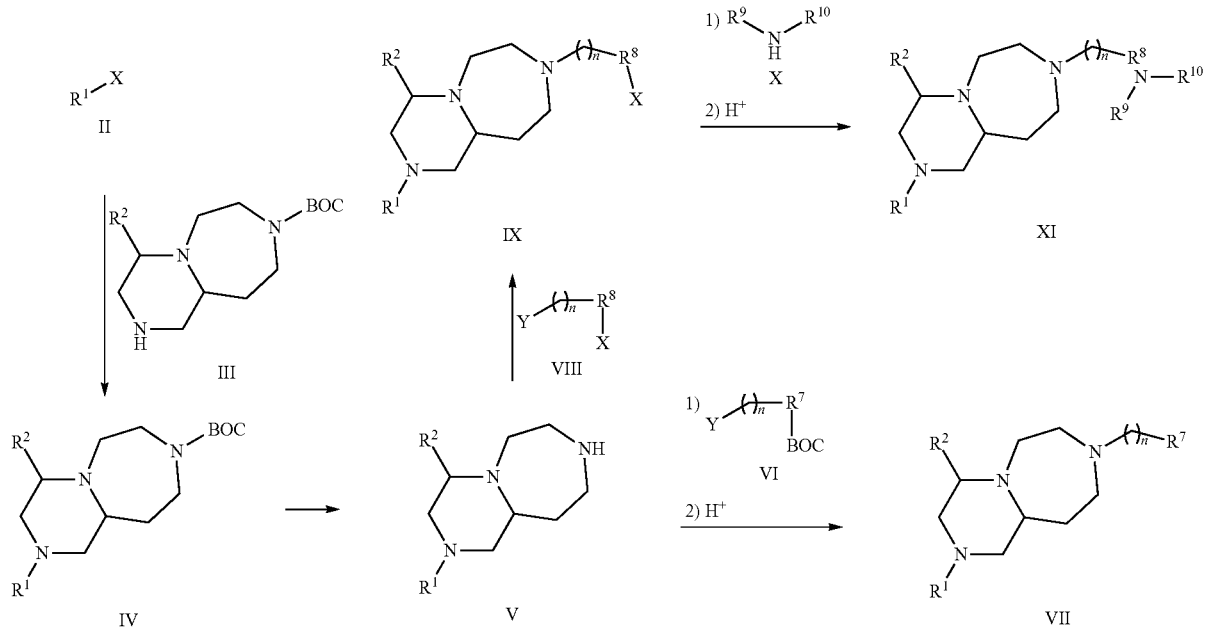

Wherein n is 0, 1 or 2; X is halogen; Y is halogen or methanesulfonate; $R^7$ and $R^8$ is aryl or heteroaryl; $R^9$ and $R^{10}$ together with the nitrogen atom they are attached to form a heterocyclyl.

The synthesis of compounds of the present invention started from halide II. Buchwald-Hartwig amination reaction between halide II and compound of formula III with a catalyst, such as Ruphos Pd-G2, and a base, such as $Cs_2CO_3$ provides compound of formula IV (ref: Acc. Chem. Res. 1998, 31, 805-818; Chem. Rev. 2016, 116, 12564-12649; Topics in Current Chemistry, 2002, 219, 131-209; and references cited therein). Alternatively, compound of formula IV can also be obtained via nucleophilic substitution between halide II and compound of formula III in the presence of a base, such as DIPEA, $NaHCO_3$ and $K_2CO_3$. Boc deprotection of compound of formula IV in acidic condition (such as HCl in EtOAc and TFA in DCM) gives compound V, which can be transformed into compound of formula VII via either nucleophilic substitution with compound of formula VI in the presence of a base, such as DIPEA $NaHCO_3$ and $K_2CO_3$, or Buchwald-Hartwig amination reaction with compound of formula VI followed by appropriate deprotection. Meanwhile, compound of formula V can react with compound of formula VIII via nucleophilic substitution to give compound of formula IX. Buchwald-Hartwig amination reaction or nucleophilic substitution between compound of formula IX and amine X, followed by appropriate deprotection can provide compound of formula XI.

Compounds of formula (Ia) can be synthesized according to Scheme 1 using chiral starting materials.

Compounds of this invention can be obtained as mixtures of diastereomers or enantiomers, which can be separated by methods well known in the art, e.g. (chiral) HPLC or SFC.

This invention also relates to a process for the preparation of a compound of formula (I) or (Ia) comprising any one of the following steps:

a) Buchwald-Hartwig amination reaction or nucleophilic substitution between compound of formula (IX),

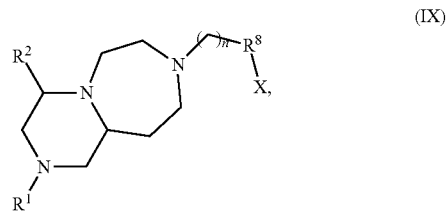

(IX)

and amine (X),

(X)

b) Buchwald-Hartwig amination reaction or nucleophilic substitution between compound of formula (V),

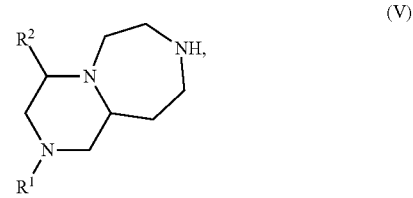

(V)

and compound of formula (VI),

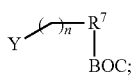

(VI)

wherein n is 0, 1 or 2; X is halogen; Y is halogen or methanesulfonate; $R^7$ and $R^8$ is aryl or heteroaryl; $R^9$ and $R^{10}$ together with the nitrogen atom they are attached to form a heterocyclyl.

Compound of formula (Ia) can also be synthesized according to Scheme 1 by using chiral intermediates.

A compound of formula (I) or (Ia) when manufactured according to the above process is also an object of the invention.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:
ACN: acetonitrile
DCM: dichloromethane
DCE: dichloroethane
DIPEA or DIEA: N,N-diisopropylethylamine
DMF: N,N-Dimethylformamide
EA or EtOAc: ethyl acetate
FA: formic acid
HATU: 1-[Bis(dimethylamino)methylene]-1H-1,2,3-triazolo[4,5-b]pyridinium 3-oxid hexafluorophosphate
$IC_{50}$: half inhibition concentration
IPA: isopropanol
MS: mass spectrometry
prep-HPLC: preparative high performance liquid chromatography
prep-TLC: preparative thin layer chromatography
RuPhos Pd G2: chloro(2-dicyclohexylphosphino-2',6'-diisopropoxy-1,1'-biphenyl)[2-(2'-amino-1,1'-biphenyl)]palladium(II) 2nd generation
Selectfluor 1-chloromethyl-4-fluoro-1,4-diazoniabicyclo[2.2.2]octane bis(tetrafluoroborate)
SFC: supercritical fluid chromatography
TEA: trimethylamine
TFA: trifluoroacetic acid
THF: tetrahydrofuran
XantPhos: 4,5-bis(diphenylphosphino)-9,9-dimethylxanthene
v/v volume ratio

GENERAL EXPERIMENTAL CONDITIONS

Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 µm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 µm, OBD™ 30×100 mm) column, SunFire™ Prep-C18 (5 µm, OBD™ 30×100 mm) column, Phenomenex Synergi-C18 (10 µm, 25×150 mm) or Phenomenex Gemini-C18 (10 µm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 µm, 30×250 mm), AS (10 µm, 30×250 mm) or AD (10 µm, 30×250 mm) using Mettler Toledo Multigram III system SFC, Waters 80Q preparative SFC or Thar 80 preparative SFC, solvent system: $CO_2$ and IPA (0.5% TEA in IPA) or $CO_2$ and MeOH (0.1% $NH_3 \cdot H_2O$ in MeOH), back pressure 100 bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):
Acidic condition I: A: 0.1% TFA in $H_2O$; B: 0.1% TFA in acetonitrile;
Acidic condition II: A: 0.0375% TFA in $H_2O$; B: 0.01875% TFA in acetonitrile;
Basic condition I: A: 0.1% $NH_3 \cdot H_2O$ in $H_2O$; B: acetonitrile;
Basic condition II: A: 0.025% $NH_3 \cdot H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

PREPARATIVE EXAMPLES

The following examples are intended to illustrate the meaning of the present invention but should by no means represent a limitation within the meaning of the present invention:

Intermediate A1

5-fluoroquinoline-8-carbonitrile

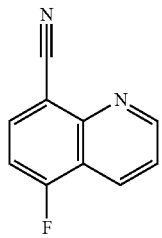

The titled compound was synthesized according to the following scheme:

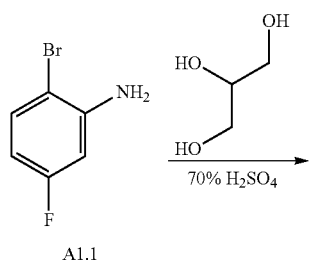

Step (a): Preparation of 8-bromo-5-fluoro-quinoline (Compound A1.2)

In a 100 mL pear-shaped flask, 2-bromo-5-fluoroaniline (compound A1.1, 2.0 g, 10.5 mmol), propane-1,2,3-triol (969 mg, 10.5 mmol) and sodium 3-nitrobenzenesulfonate (2.4 g, 10.5 mmol) were combined with 70% $H_2SO_4$ (20 mL) to afford a dark brown solution, which was heated to 150° C. and stirred for 3 hrs. After being cooled to room temperature, the reaction mixture was poured into ice-water, and neutralized with sodium hydroxide solution. The resultant mixture was filtered. The filter cake was dissolved in EtOAc and filtered. The resultant filtrate was concentrated in vacuo. The crude material was purified by flash chromatography (silica gel, 40 g, 0% to 30% EtOAc in PE) to afford compound A1.2 (2.0 g, 84% yield). MS: calc'd 226 and 228 [(M+H)$^+$], measured 226 and 228 [(M+H)$^+$].

Step (b): Preparation of 5-fluoroquinoline-8-carbonitrile (intermediate A1)

To a solution of 8-bromo-5-fluoroquinoline (compound A1.2, 4.9 g, 21.7 mmol) in DMF (30 mL) was added dicyanozinc (5.0 g, 43.4 mmol) and RuPhos Pd G2 (CAS: 1375325-68-0, Sigma-Aldrich, Catalog: 753246, 842 mg, 1.1 mmol). The reaction mixture was stirred at 100° C. for 3 hrs, then cooled to room temperature. The reaction mixture was filtered and the filtrate was diluted with water (50 mL), then extracted with EA (80 mL) for three times. The combined organic layer was washed with brine, dried over $Na_2SO_4$, filtered and concentrated in vacuo. The residue was purified by flash chromatography (silica gel, 40 g, 0% to 70% EtOAc in PE) to afford intermediate A1 (3.0 g, 80% yield). MS: calc'd 173 [(M+H)$^+$], measured 173 [(M+H)$^+$]. $^1$H NMR (400 MHz, METHANOL-$d_4$) δ ppm 9.11 (dd, J=4.28, 1.71 Hz, 1H), 8.64 (dd, J=8.56, 1.71 Hz, 1H), 8.29 (dd, J=8.19, 5.62 Hz, 1H), 7.76 (dd, J=8.56, 4.28 Hz, 1H), 7.49 (dd, J=9.35, 8.25 Hz, 1H).

Intermediate A2

4-chloro-1-methyl-1,8-naphthyridin-2-one

The titled compound was synthesized according to the following scheme:

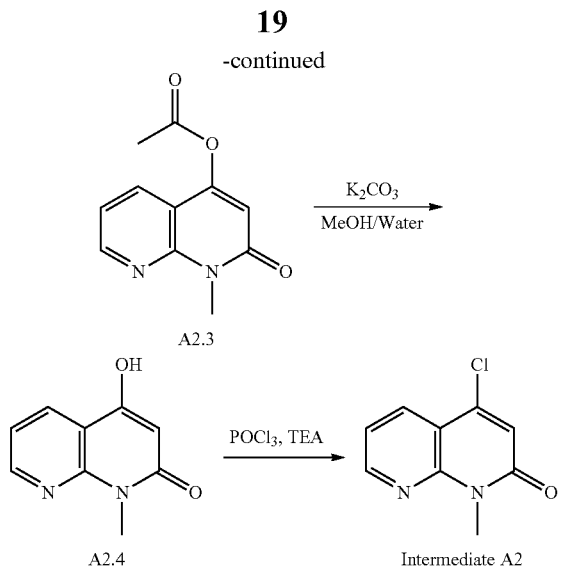

Step (a): Preparation of 2-(methylamino)pyridine-3-carboxylic acid (Compound A2.2)

2-chloronicotinic acid (compound A2.1, 1.0 kg, 6.3 mmol) was dissolved in 33% monomethylamine (386.3 mol) solution in ethanol. The reaction mixture was stirred in the autoclave at 80° C. for 80 hrs, then concentrated in vacuo to afford compound A2.2 (1.4 kg, crude). MS: calc'd 153 [(M+H)$^+$], measured 153 [(M+H)$^+$].

Step (b): Preparation of (1-methyl-2-oxo-1,8-naphthyridin-4-yl) acetate (Compound A2.3)

A solution of 2-(methylamino)pyridine-3-carboxylic acid (compound A2.2, 1.4 kg, crude) in acetic anhydride (10.0 L, 105789 mmol) and acetic acid (5.0 L) was heated to reflux for 2 hrs. The reaction mixture was concentrated in vacuo to afford compound A2.3 (1.8 kg, crude). MS: calc'd 219 [(M+H)$^+$], measured 219 [(M+H)$^+$].

Step (c): Preparation of 4-hydroxy-1-methyl-1,8-naphthyridin-2-one (Compound A2.4)

To a solution of (1-methyl-2-oxo-1,8-naphthyridin-4-yl) acetate (Compound A2.3, 1.8 kg, crude) in methanol (12.0 L) was added a solution of potassium carbonate (1.9 kg, 13.75 mol) in water (3.6 L). The mixture was stirred at 25° C. for 2 hrs. Then the reaction mixture was concentrated under reduced pressure to remove the MeOH. The residue was acidified with HCl solution (6 N) to pH 4-5, extracted with EA (1500 mL) for three times. The combined organic layer was washed with sat. brine (1500 mL), dried over Na$_2$SO$_4$, and concentrated in vacuo to afford compound A2.4 (450 g, 40.2% yield). MS: calc'd 177 [(M+H)$^+$], measured 177 [(M+H)$^+$]; $^1$H NMR (400 MHz, DMSO-d$_6$) δ ppm 11.68 (s, 1H), 8.63 (dd, J=4.60, 1.80 Hz, 1H), 8.22 (dd, J=7.80, 1.80 Hz, 1H), 7.27 (dd, J=7.80, 4.60 Hz, 1H), 5.93 (s, 1H), 3.59 (s, 3H)

Step (d): Preparation of 4-chloro-1-methyl-1,8-naphthyridin-2-one (Intermediate A2)

A solution of 4-hydroxy-1-methyl-1,8-naphthyridin-2-one (compound A2.4, 150 g, 0.85 mol) in phosphorus oxychloride (300 mL) was stirred at 100° C. for 2 hrs. The reaction mixture was concentrated in reduced pressure to remove the phosphorus oxychloride. The residue was neutralized by adding saturated aqueous NaHCO$_3$ at room temperature to pH 7-8, and the mixture was extracted with DCM (1000 mL) twice. The combined organic layer was washed sat. brine (500 mL), dried over Na$_2$SO$_4$ and concentrated in vacuo to give a crude product, which was purified by silica gel chromatography (PE/EtOAc=1:0 to 7:1) to afford Intermediate A2 (39 g, 24% yield). MS: calc'd 195 [(M+H)$^+$], measured 195 [(M+H)$^+$]; $^1$H NMR (400 MHz, DMSO-d$_6$) δ ppm 8.75 (dd, J=4.60, 1.60 Hz, 1H), 8.32 (dd, J=7.90, 1.70 Hz, 1H), 7.44 (dd, J=8.00, 4.60 Hz, 1H), 7.03 (s, 1H), 3.66 (s, 3H).

Intermediate A3

4-fluoropyrazolo[1,5-a]pyridine-7-carbonitrile

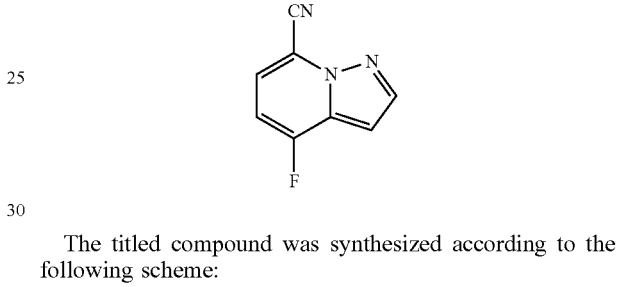

The titled compound was synthesized according to the following scheme:

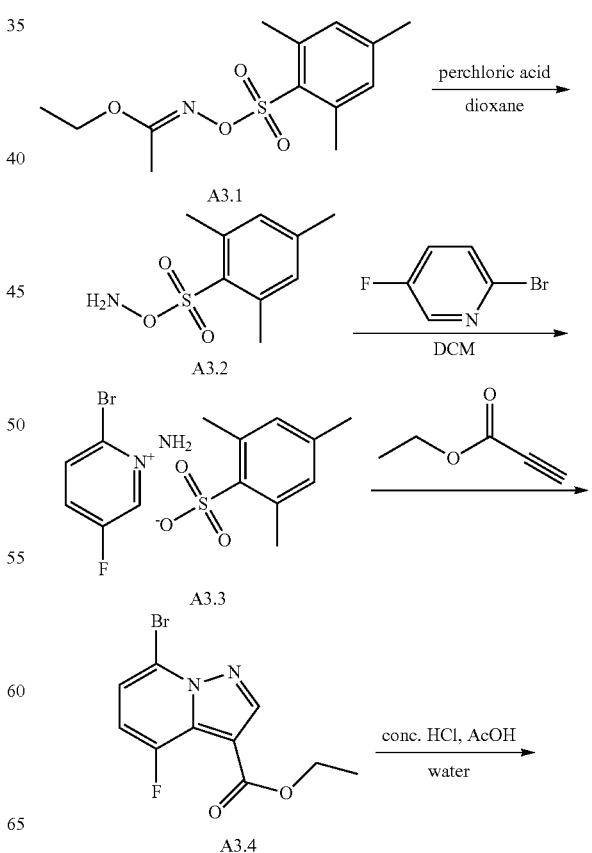

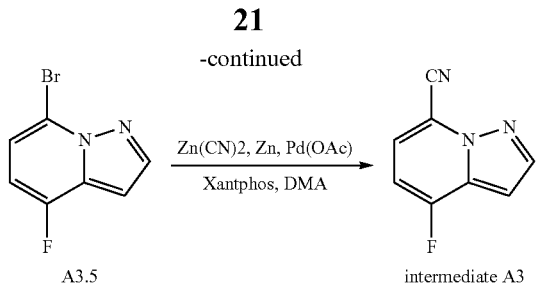

Step (a): Preparation of amino 2,4,6-trimethylbenzenesulfonate (Compound A3.2)

A solution of ethyl (1E)-N-(2,4,6-trimethylphenyl)sulfonyloxyethanimidate (compound A3.1, CAS: 38202-27-6, Bide Pharmatech, Catalog: BD129455, 200 g, 700 mmol) in 1,4-dioxane (500 mL) was added perchloric acid (110 mL) dropwise in 30 min and stirred for 1 hr at 0° C. 1000 mL ice water was added and the mixture was filtered. The filter cake was dissolved in 1.5 L EtOAc and then was stirred for 30 minutes. The organic layer was concentrated (keep the temperature below 25° C.) to afford crude product. The crude product was recrystallized (petroleum/EtOAc=10/1) to afford compound A3.2 (110 g, 73% yield). MS: calc'd 216 [(M+H)$^+$], measured 216 [(M+H)$^+$].

Step (b): Preparation of 2-bromo-5-fluoro-pyridin-1-ium-1-amine;2,4,6-trimethylbenzenesulfonate (Compound A3.3)

A solution of amino 2,4,6-trimethylbenzenesulfonate (compound A3.2, 110 g, 511 mmol) and 2-bromo-5-fluoro-pyridine (60 g, 341 mmol) in DCM (1800 mL) was stirred at 10° C. for 18 hrs. The mixture was concentrated, the residue was recrystallized in EtOAc to afford compound A3.3 (90 g, 92% yield). MS: calc'd 191 [(M+H)$^+$], measured 191 [(M+H)$^+$].

Step (c): Preparation of ethyl 7-bromo-4-fluoro-pyrazolo[1,5-a]pyridine-3-carboxylate (Compound A3.4)

A solution of 2-bromo-5-fluoro-pyridin-1-ium-1-amine; 2,4,6-trimethylbenzenesulfonate (compound A3.3, 90 g, 230 mmol), K$_2$CO$_3$ (64 g, 460 mmol) and ethyl propiolate (28 mL, 276 mmol) in DMF (1300 mL) was stirred at 10° C. for 18 hrs. The reaction was diluted with water, extracted with EtOAc. The organic layer was dried over Na$_2$SO$_4$, filtered and the filtrate was concentrated in vacuo. The residue was purified by chromatography column to afford compound A3.4 (11 g, 16.7% yield). MS: calc'd 287 [(M+H)$^+$], measured 287 [(M+H)$^+$].

Step (d): Preparation of 7-bromo-4-fluoropyrazolo[1,5-a]pyridine (Compound A3.5)

To a mixture of ethyl 7-bromo-4-fluoro-pyrazolo[1,5-a]pyridine-3-carboxylate (compound A3.4, 8.0 g, 26.7 mmol) in acetic acid (48 mL) and water (48 mL) was added conc. HCl (36 mL, 432 mmol). The mixture was stirred at 100° C. for 18 hrs. The mixture was diluted with water (200 mL), basified with aq. NaOH (1N) to pH 8, extracted with EA (200 mL) for three times. The combined organic layer was washed with brine, dried over Na$_2$SO$_4$ and concentrated in vacuo to afford compound A3.5 (5 g, 86.9% yield) which was used directly for the next step.

MS: calc'd 215 [(M+H)$^+$], measured 215 [(M+H)$^+$].

Step (e): Preparation of 4-fluoropyrazolo[1,5-a]pyridine-7-carbonitrile (Intermediate A3)

A mixture of 7-bromo-4-fluoro-pyrazolo[1,5-a]pyridine (Compound A3.5, 1000 mg, 4.6 mmol), zinc cyanide (880 mg, 7.5 mmol), zinc (31 mg, 0.5 mmol), XantPhos (1076 mg, 1.8 mmol) and Pd(OAc)$_2$ (209 mg, 0.9 mmol) in DMA (10 mL) was degassed and purged with Ar for 3 times, and then the mixture was stirred at 120° C. for 1 h under Ar atmosphere. The mixture was diluted with EA (150 mL), filtered and the filtrate was washed with water (50 mL), brine (50 mL) three times, dried over Na$_2$SO$_4$ and concentrated in vacuo. The residue was purified by Prep-TLC (PE:EA=3:1) to afford Intermediate A3 (600 mg, 68% yield). MS: calc'd 162 [(M+H)$^+$], measured 162 [(M+H)$^+$].

Intermediate A4

3,4-Difluoropyrazolo[1,5-a]pyridine-7-carbonitrile

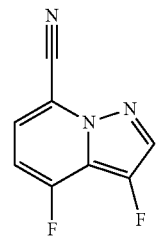 [SMILES: N#Cc1ccc(F)c2c(F)cnn12]

The titled compound was synthesized according to the following scheme:

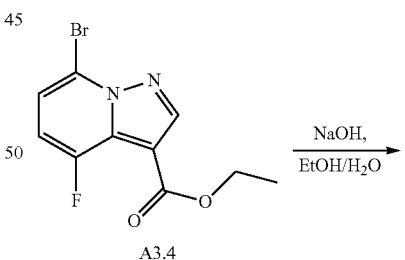

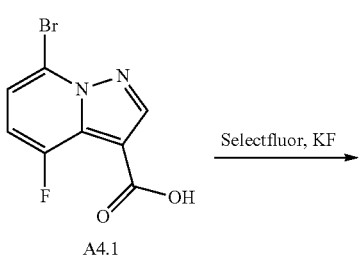

23

-continued

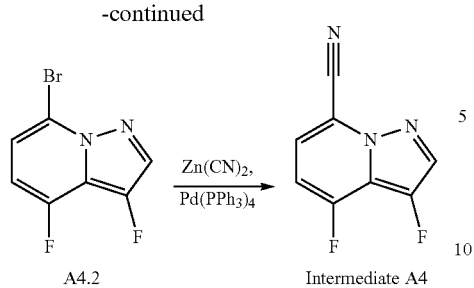

Step (a): Preparation of 7-bromo-4-fluoro-pyrazolo[1,5-a]pyridine-3-carboxylic acid (Compound A4.1)

The mixture of ethyl 7-bromo-4-fluoro-pyrazolo[1,5-a]pyridine-3-carboxylate (compound A3.4, 5.2 g, 18.1 mmol), NaOH (2.1 g, 54.3 mmol) in EtOH (90.0 mL) and water (70.0 mL) was stirred at 60° C. for 2 hrs. The reaction mixture was concentrated and then diluted with water. After adjusting pH to 4 with 1 N HCl, grey solid was precipitated, which was collected by filtration to afford compound A4.1 (4.0 g, 85.6% yield). MS: calc'd 259 [(M+H)$^+$], measured 259 [(M+H)$^+$].

Step (b): Preparation of 7-bromo-3,4-difluoro-pyrazolo[1,5-a]pyridine (Compound A4.2)

To a solution of 7-bromo-4-fluoro-pyrazolo[1,5-a]pyridine-3-carboxylic acid (compound A4.1, 4.0 g, 15.4 mmol) and KF (3.6 g, 61.8 mmol) in DCE (60.0 mL) and water (50.0 mL) was added Selectfluor (10.9 g, 30.9 mmol). The reaction was stirred at 70° C. for 18 hrs. The reaction was quenched with water, extracted with DCM twice. The combined organic layer was dried over Na$_2$SO$_4$, filtered and the filtrate was concentrated in vacuo to afford crude compound A4.2 (2.8 g, 78% yield). MS: calc'd 233 [(M+H)$^+$], measured 233 [(M+H)$^+$].

Step (c): Preparation of 3,4-difluoropyrazolo[1,5-a]pyridine-7-carbonitrile (Intermediate A4)

A solution of 7-bromo-3, 4-difluoro-pyrazolo[1,5-a]pyridine (Compound A4.2, 2.8 g, 12.0 mmol) and zinc cyanide (5.6 g, 48.0 mmol) in DMF (70.0 mL) was added tetrakis(triphenylphosphine)palladium (1.4 g, 1.2 mmol). The reaction mixture was stirred at 120° C. for 18 hrs under N$_2$ atmosphere. The mixture was quenched with water and extracted with EtOAc twice. The combined organic layer was dried over Na$_2$SO$_4$, filtered and the filtrate was concentrated in vacuo. The residue was purified by column chromatography to afford Intermediate A4 (810 mg, 37.7% yield). MS: calc'd 180 [(M+H)$^+$], measured 180 [(M+H)$^+$]. $^1$H NMR (400 MHz, CHLOROFORM-d) δ ppm 8.00 (d, J=3.6 Hz, 1H), 7.31 (dd, J=4.7, 8.0 Hz, 1H), 6.83 (t, J=8.4 Hz, 1H).

24

Intermediate B tert-Butyl (4R,10aS)-4-methyl-2,3,4,6,7,9,10,10a-octahydro-1H-pyrazino[1,2-d][1,4]diazepine-8-carboxylate

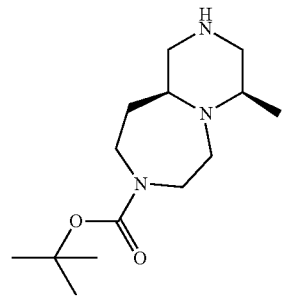 [SMILES: C[C@@H]1CNC[C@@H]2CCN(C(=O)OC(C)(C)C)CCN21]

The titled compound was synthesized according to the following scheme:

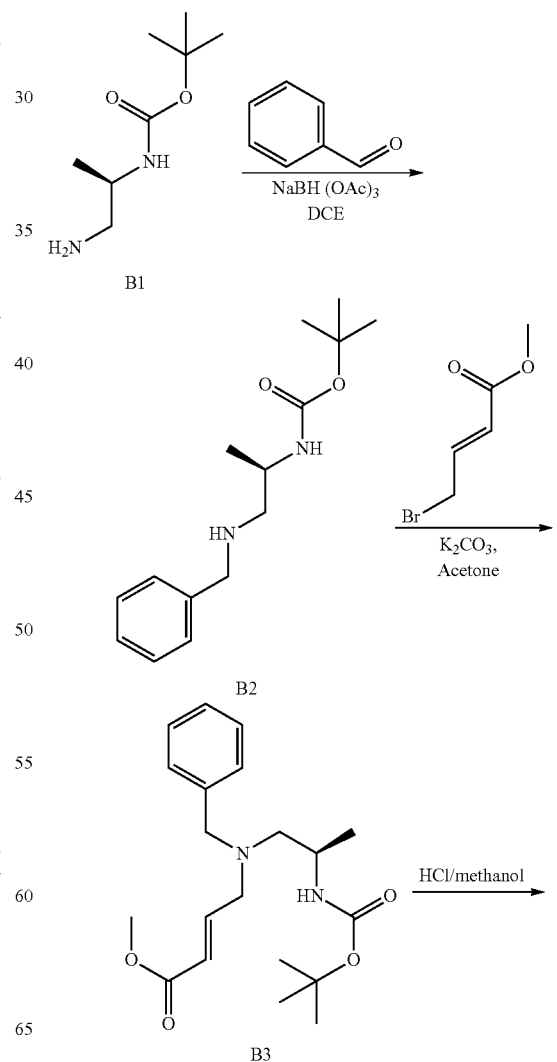

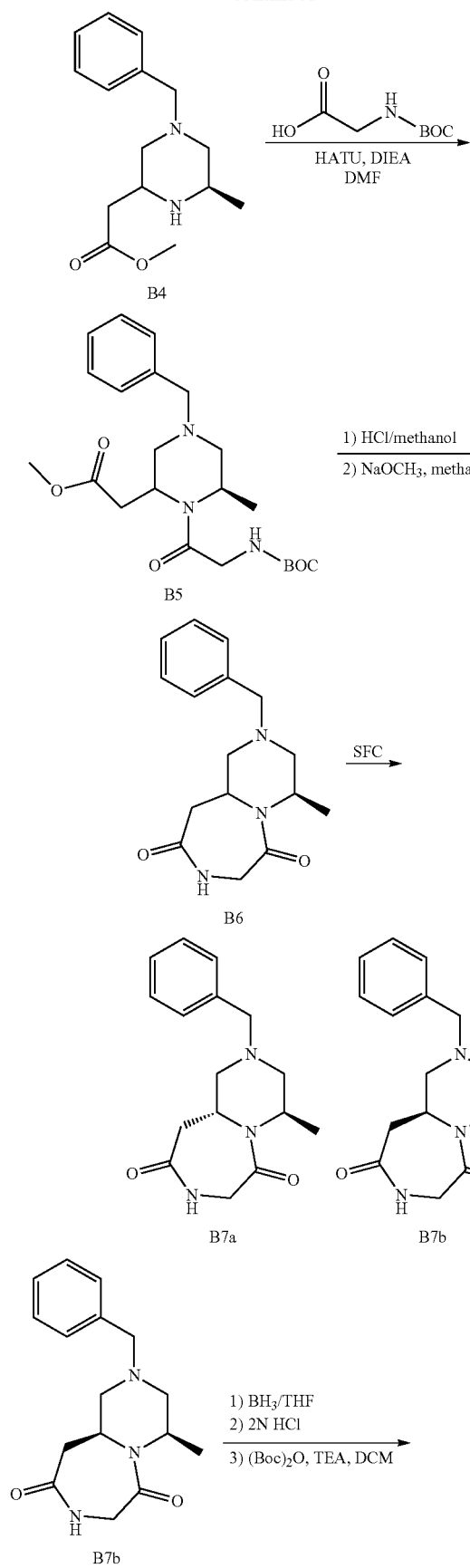

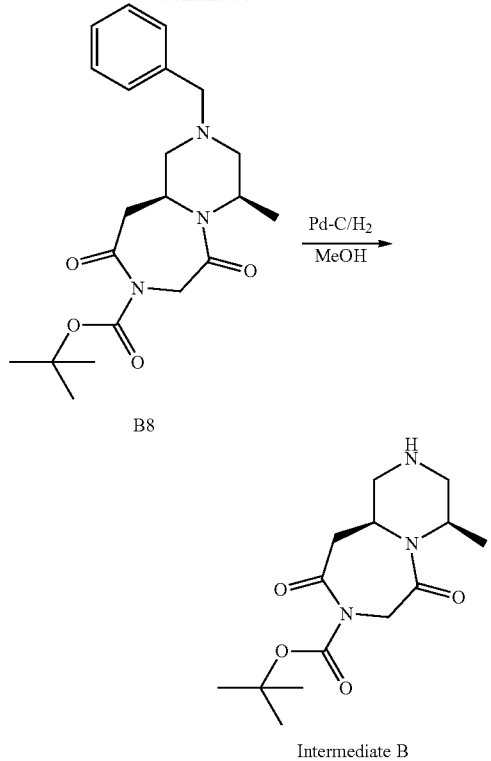

Intermediate B

Step (a): Preparation of tert-butyl N-[(1R)-2-(benzylamino)-1-methyl-ethyl]carbamate (Compound B2)

The mixture of tert-butyl (R)-(1-aminopropan-2-yl)carbamate (4.95 g, 28.40 mmol), benzaldehyde (2.86 g, 27 mmol) and DCE (80 mL) was stirred at room temperature for 30 min. Then NaBH(OAc)$_3$ (12.0 g, 56.80 mmol) was added to the mixture. The resultant mixture was stirred at room temperature for 2 hrs, then quenched with water (100 mL), extracted with DCM (80 mL) for three times. The combined organic layer was washed with brine, dried over Na$_2$SO$_4$ and concentrated in vacuo. The residue was purified by flash chromatography (silica gel, 80 g, 0% to 30% EtOAc in DCM) to afford compound B2 (5.10 g, 68% yield). MS: calc'd 265 [(M+H)$^+$], measured 265 [(M+H)$^+$].

Step (b): Preparation of methyl (E)-4-[benzyl-[(2R)-2-(tert-butoxycarbonylamino) propyl]amino] but-2-enoate (Compound B3)

To a solution of tert-butyl N-[(1R)-2-(benzylamino)-1-methyl-ethyl]carbamate (compound B2, 5.10 g, 19.30 mmol) in acetone (150 mL) was added methyl (E)-4-bromobut-2-enoate (3.45 g, 19.3 mmol) and K$_2$CO$_3$ (5.33 g, 38.6 mmol). The reaction mixture was stirred at room temperature for 20 hrs, then filtered through celite and the filtrate was concentrated. The residue was purified by flash chromatography (silica gel, 80 g, 0% to 30% EtOAc in PE) to afford compound B3 (4.20 g, 60% yield). MS: calc'd 363 [(M+H)$^+$], measured 363 [(M+H)$^+$].

Step (c): Preparation of methyl 2-[(6R)-4-benzyl-6-methyl-piperazin-2-yl]acetate (Compound B4)

The mixture of methyl (E)-4-[benzyl-[2R)-2-(tert-butoxycarbonylamino)propyl]amino]but-2-enoate (compound B3, 4.20 g, 11.60 mmol) and HCl/MeOH (1 N, 70 mL, 70 mmol) was heated at reflux for 2 hrs. After being cooled to room temperature, the reaction mixture was neutralized with saturated aq. $K_2CO_3$, and extracted with DCM (80 mL) twice. The combined organic layer was washed with brine, dried over $Na_2SO_4$, filtered and concentrated in vacuo. The residue was purified by flash chromatography (silica gel, 40 g, 0% to 20% MeOH in DCM) to afford compound B4 (2.40 g, 79% yield). MS: calc'd 263 [(M+H)$^+$], measured 263 [(M+H)$^+$].

Step (d): Preparation of methyl 2-[(6R)-4-benzyl-1-[2-(tert-butoxycarbonylamino)-acetyl]-6-methyl-piperazin-2-yl]acetate (Compound B5)

To a solution of (tert-butoxycarbonyl)glycine (3.50 g, 20.0 mmol) in DMF (40 mL) was added methyl 2-[(6R)-4-benzyl-6-methyl-piperazin-2-yl]acetate (compound B4, 5.24 g, 20.0 mmol), DIEA (7.74 g, 60.0 mmol) and HATU (7.60 g, 20.0 mmol). The resultant mixture was stirred at room temperature for 3 hrs. The reaction was quenched with water (100 mL), and extracted with DCM (80 mL) for three times. The combined organic layer was washed with brine, dried over $Na_2SO_4$, filtered and the filtrate was concentrated in vacuo. The residue was purified by flash chromatography (silica gel, 120 g, 0% to 60% EtOAc in PE) to afford compound B5 (7.2 g, 85.9% yield). MS: calc'd 420 [(M+H)$^+$], measured 420 [(M+H)$^+$].

Step (e): Preparation of (4R)-2-benzyl-4-methyl-3,4,7,8,10,10a-hexahydro-1H-pyrazino[1,2-d][1,4]diazepine-6,9-dione (Compound B6)

The mixture of methyl 2-[(6R)-4-benzyl-1-[2-(tert-butoxycarbonylamino)-acetyl]-6-methyl-piperazin-2-yl]acetate (compound B5, 5.0 g, 11.9 mmol) and HCl/MeOH (7% HCl in MeOH, 80 mL) was stirred at reflux for 2 hrs. The reaction mixture was concentrated, the residue was diluted with MeOH (100 mL), and then sodium methoxide (3.22 g, 59.60 mmol) was added. The resultant mixture was stirred at reflux for 5 hrs. After being cooled to room temperature, the reaction was quenched with water (300 mL), and extracted with EA (100 mL) for three times. The combined organic layer was washed with brine, dried over $Na_2SO_4$, filtered and the filtrate was concentrated in vacuo. The residue was purified by flash chromatography to afford compound B6 (2.30 g, 67.3% yield). MS: calc'd 288 [(M+H)$^+$], measured 288 [(M+H)$^+$].

Step (f): Preparation of (4R,10aR)-2-benzyl-4-methyl-3,4,7,8,10,10a-hexahydro-1H-pyrazino[1,2-d][1,4]diazepine-6,9-dione (Compound B7a) and (4R,10aS)-2-benzyl-4-methyl-3,4,7,8,10,10a-hexahydro-1H-pyrazino[1,2-d][1,4]diazepine-6,9-dione (Compound B7b)

Compound B7a (2.30 g) was resolved by SFC to give two single isomers: compound B7a (faster eluting, 0.63 g, 27.4% yield) and compound B7b (slower eluting, 1.56 g, 67.8% yield) with 25% Methanol/CO$_2$ on OJ (5 μm, 250×30 mm) column. The stereochemistry was confirmed by NOESY.

Compound B7a: MS: calc'd 288 (M+H)$^+$, measured 288 (M+H)$^+$; $^1$H NMR (400 MHz, METHANOL-d$_4$) δ ppm 7.05-7.55 (m, 5H), 4.82 (ddd, J=1.71, 4.03, 6.85 Hz, 1H), 4.04 (s, 2H), 3.91-4.01 (m, 1H), 3.54-3.64 (m, 1H), 3.43-3.49 (m, 1H), 2.95 (dd, J=4.40, 14.43 Hz, 1H), 2.87 (td, J=2.17, 11.19 Hz, 1H), 2.78 (dd, J=7.76, 14.49 Hz, 1H), 2.72 (td, J=1.71, 11.49 Hz, 1H), 2.14 (dd, J=3.91, 11.49 Hz, 1H), 2.04 (t, J=11.07 Hz, 1H), 1.32 (d, J=6.85 Hz, 3H).

Compound B7b: MS: calc'd 288 (M+H)$^+$, measured 288 (M+H)$^+$; $^1$H NMR (400 MHz, METHANOL-d$_4$) δ ppm 7.38-7.42 (m, 2H), 7.32-7.39 (m, 2H), 7.05-7.71 (m, 1H), 4.58 (d, J=14.79 Hz, 1H), 4.45 (td, J=3.81, 13.54 Hz, 1H), 4.30-4.39 (m, 1H), 3.52-3.65 (m, 2H), 3.46 (d, J=14.92 Hz, 1H), 3.10 (dd, J=13.45, 18.46 Hz, 1H), 2.75-2.82 (m, 1H), 2.77 (s, 1H), 2.53 (dd, J=2.87, 18.40 Hz, 1H), 2.39 (dd, J=5.26, 12.10 Hz, 1H), 2.27 (dd, J=4.46, 11.55 Hz, 1H), 1.27 (d, J=6.72 Hz, 3H).

Step (g): Preparation of tert-butyl (4R,10aS)-2-benzyl-4-methyl-1,3,4,6,7,9,10,10a-octahydropyrazino[1,2-d][1,4]diazepine-8-carboxylate (Compound B8)

A mixture of (4R,10aS)-2-benzyl-4-methyl-3,4,7,8,10,10a-hexahydro-1H-pyrazino[1,2-d][1,4]diazepine-6,9-dione (Compound B7b, 1.56 g, 5.43 mmol) and BH$_3$ solution (1M in THF, 40 mL, 40 mmol) was heated at 80° C. with stirring on for 20 hrs. The reaction mixture was cooled to 0° C., then HCl solution (2 N, 10 mL) was added slowly to the reaction mixture at same temperature. The resultant mixture was stirred at reflux for 3 hrs, then the mixture was cooled back to room temperature. After the organic solvent was removed in vacuo, the residue was diluted with DCM (100 mL). Boc-Anhydride (1.77 g, 8.12 mmol) and TEA (2.74 g, 27.1 mmol) were added respectively. The resultant mixture was stirred at room temperature for 2 hrs. The reaction was quenched with water (50 mL), and extracted with DCM (50 mL) for three times. The combined organic layer was washed with brine, dried over $Na_2SO_4$, filtered and concentrated in vacuo. The residue was purified by flash chromatography (silica gel, 80 g, 20% to 80% EtOAc in DCM) to afford compound B8 (1.8 g, 92.4% yield). MS: calc'd 360 [(M+H)$^+$], measured 360 [(M+H)$^+$].

Step (h): Preparation of tert-butyl (4R,10aS)-4-methyl-2,3,4,6,7,9,10,10a-octahydro-1H-pyrazino[1,2-d][1,4]diazepine-8-carboxylate (Intermediate B)

A mixture of tert-butyl (4R,10aS)-2-benzyl-4-methyl-1,3,4,6,7,9,10,10a-octahydropyrazino[1,2-d][1,4]diazepine-8-carboxylate (compound B8, 1.8 g, 5.01 mmol) and Pd—C (100 mg) in MeOH (100 mL) was hydrogenated by a hydrogen balloon at room temperature for 5 hrs. After the catalyst was filtered off, the filtrate was concentrated in vacuo to afford Intermediate B (1.2 g, 89% yield) which was used directly for the next step without further purification. MS: calc'd 270 [(M+H)$^+$], measured 270 [(M+H)$^+$].

Intermediate C1

5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride

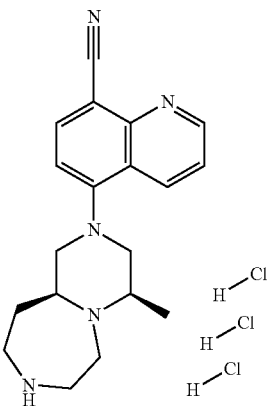

The titled compound was synthesized according to the following scheme:

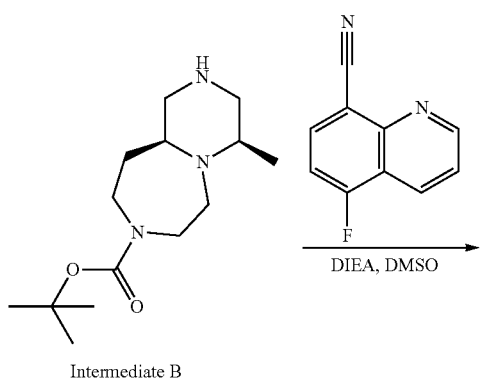

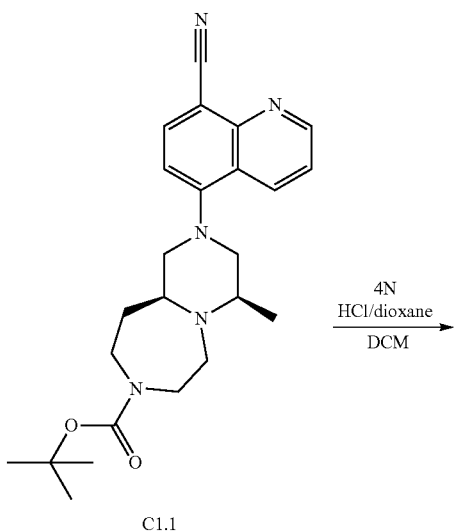

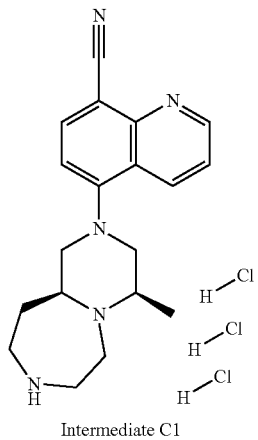

Intermediate C1

Step (a): Preparation of tert-butyl (4R,10aS)-2-(8-cyano-5-quinolyl)-4-methyl-1,3,4,6,7, 9,10,10a-octahydropyrazino[1,2-d][1,4]diazepine-8-carboxylate (Compound C1.1)

To a solution of tert-butyl (4R,10aS)-4-methyl-2,3,4,6,7, 9,10,10a-octahydro-1H-pyrazino [1,2-d][1,4]diazepine-8-carboxylate (Intermediate B, 1.20 g, 4.45 mmol) in DMSO (20 mL) was added 5-fluoroquinoline-8-carbonitrile (Intermediate A1, 0.77 g, 4.45 mmol) and DIEA (0.58 g, 4.45 mmol). The resultant mixture was stirred at 120° C. for 5 hrs. After being cooled to room temperature, the reaction was quenched with water (100 mL) and extracted with EA (90 mL) for three times. The combined organic layer was washed with brine, dried over $Na_2SO_4$, filtered and concentrated in vacuo. The residue was purified by flash chromatography (silica gel, 40 g, 0% to 100% EtOAc in PE) to afford compound C1.1 (1.41 g, 75.1% yield). MS: calc'd 422 [(M+H)$^+$], measured 422 [(M+H)$^+$].

Step (b): Preparation of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1)

To a solution of tert-butyl (4R,10aS)-2-(8-cyano-5-quinolyl)-4-methyl-1,3,4,6,7,9,10,10a-octahydropyrazino[1,2-d][1,4]diazepine-8-carboxylate (compound C1.1, 1.41 g, 3.34 mmol) in DCM (30 mL) was added dropwise HCl/dioxane (4 N, 8 mL) at 0° C. After addition, the mixture was stirred at rt for 2 hrs, then the reaction mixture was concentrated. The residue was dissolved in pure water (20 mL), and dried by lyophilization to afford Intermediate C1 (1.44 g, 100% yield). MS: calc'd 322 [(M+H)$^+$], measured 322 [(M+H)$^+$].

Intermediate C2

4-[(4R,10aS)-4-methyl-3,4,6,7,8,9,10,10a-octahydro-1H-pyrazino[1,2-d][1,4]diazepin-2-yl]-1-methyl-1,8-naphthyridin-2-one;trihydrochloride

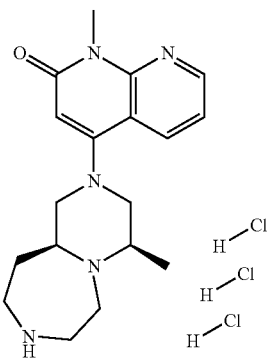

4-[(4R,10aS)-4-methyl-3,4,6,7,8,9,10,10a-octahydro-1H-pyrazino[1,2-d][1,4]diazepin-2-yl]-1-methyl-1,8-naphthyridin-2-one;trihydrochloride (Intermediate C2) was prepared in analogy to Intermediate C1, by replacing 5-fluoroquinoline-8-carbonitrile (Intermediate A1) with 4-chloro-1-methyl-1,8-naphthyridin-2-one (Intermediate A2) and CsF with the DIEA in step (a). MS: calc'd 328 [(M+H)$^+$], measured 328 [(M+H)$^+$].

Intermediate C3

4-[(4R,10aS)-4-methyl-3,4,6,7,8,9,10,10a-octahydro-1H-pyrazino[1,2-d][1,4]diazepin-2-yl]pyrazolo[1,5-a]pyridine-7-carbonitrile;trihydrochloride

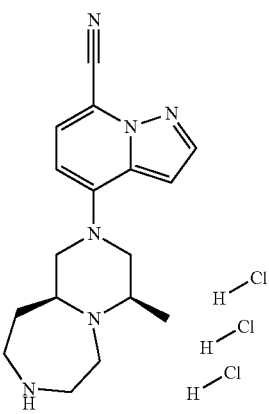

4-[(4R,10aS)-4-methyl-3,4,6,7,8,9,10,10a-octahydro-1H-pyrazino[1,2-d][1,4]diazepin-2-yl]pyrazolo[1,5-a]pyridine-7-carbonitrile;trihydrochloride (Intermediate C3) was prepared in analogy to Intermediate C1, by replacing 5-fluoroquinoline-8-carbonitrile (Intermediate A1) with 4-fluoropyrazolo[1,5-a]pyridine-7-carbonitrile (Intermediate A3) in step (a). MS: calc'd 311 [(M+H)$^+$], measured 311 [(M+H)$^+$].

Intermediate C4

4-[(4R,10aS)-4-methyl-3,4,6,7,8,9,10,10a-octahydro-1H-pyrazino[1,2-d][1,4]diazepin-2-yl]-3-fluoro-pyrazolo[1,5-a]pyridine-7-carbonitrile;trihydrochloride

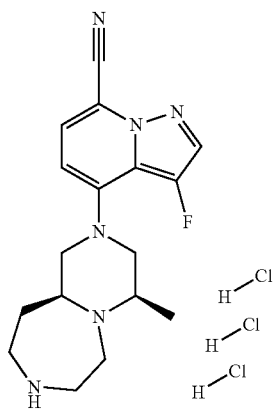

4-[(4R,10aS)-4-methyl-3,4,6,7,8,9,10,10a-octahydro-1H-pyrazino[1,2-d][1,4]diazepin-2-yl]-3-fluoro-pyrazolo[1,5-a]pyridine-7-carbonitrile;trihydrochloride (Intermediate C4) was prepared in analogy to Intermediate C1, by replacing 5-fluoroquinoline-8-carbonitrile (Intermediate A1) with 3,4-difluoropyrazolo[1,5-a]pyridine-7-carbonitrile (Intermediate A4) in step (a). MS: calc'd 329 [(M+H)$^+$], measured 329 [(M+H)$^+$].

Example 1

5-[(4R,10aS)-4-methyl-8-(6-piperazin-1-yl-3-pyridyl)-1,3,4,6,7,9,10,10a-octahydropyrazino [1,2-d][1,4]diazepin-2-yl]quinoline-8-carbonitrile

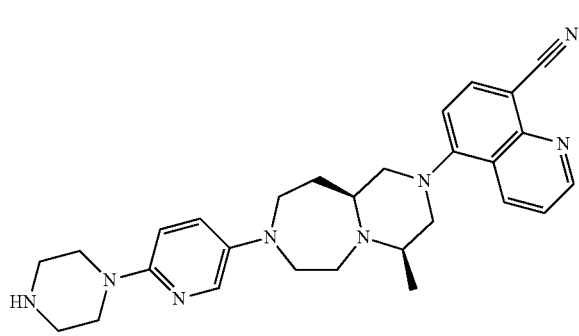 [SMILES: C[C@@H]1CN(c2ccc(C#N)c3ncccc23)C[C@@H]2CCN(c3ccc(N4CCNCC4)nc3)CCN21]

The titled compound was synthesized according to the following scheme:

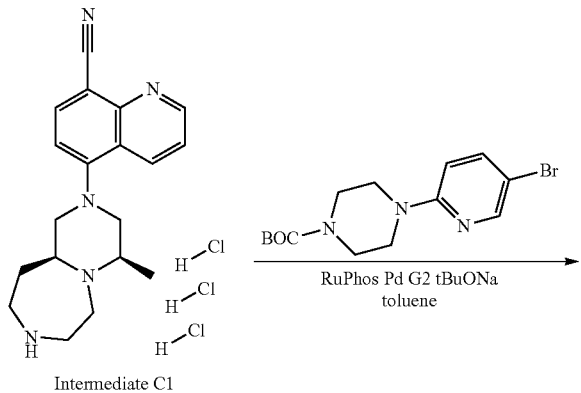

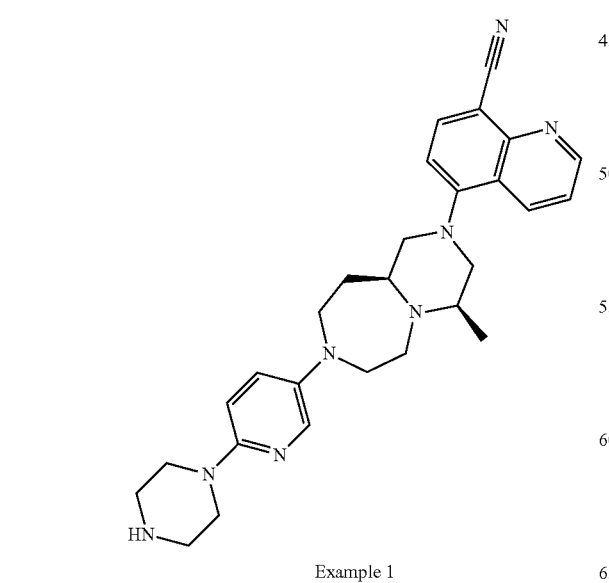

Example 1

Step (a): Preparation of tert-butyl 4-[5-[(4R,10aS)-2-(8-cyano-5-quinolyl)-4-methyl-1,3,4,6,7,9,10,10a-octahydropyrazino[1,2-d][1,4]diazepin-8-yl]-2-pyridyl]piperazine-1-carboxylate (Compound 1.1)

To a solution of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1, 70 mg, 162 μmol) in toluene (5 mL) was added tert-butyl 4-(5-bromopyridin-2-yl)piperazine-1-carboxylate (CAS: 153747-97-8, BePharm, Catalog: BD94595, 55.6 mg, 162 μmol), tBuONa (78.1 mg, 812 μmol) and RuPhos Pd G2 (CAS: 1375325-68-0, ALDRICH, Catalog: 753246, 12.6 mg, 16.2 μmol). The resultant mixture was stirred at 100° C. overnight. After being cooled to room temperature, the mixture was diluted with water (20 mL) and extracted with EA (20 mL) for three times. The combined organic layer was washed with brine, dried over $Na_2SO_4$, filtered and concentrated in vacuo. The residue was purified by flash chromatography (silica gel, 20 g, 0% to 100% EtOAc in PE) to afford compound 1.1 (38 mg, 40.1% yield). MS: calc'd 583 [(M+H)$^+$], measured 583 [(M+H)$^+$].

Step (b): Preparation of 5-[(4R,10aS)-4-methyl-8-(6-piperazin-1-yl-3-pyridyl)-1,3,4,6,7,9,10,10a-octahydropyrazino[1,2-d][1,4]diazepin-2-yl]quinoline-8-carbonitrile (Example 1)

To a solution of tert-butyl 4-[5-[(4R,10aS)-2-(8-cyano-5-quinolyl)-4-methyl-1,3,4,6,7,9,10,10a-octahydropyrazino[1,2-d][1,4]diazepin-8-yl]-2-pyridyl]piperazine-1-carboxylate (compound 1.1, 38 mg, 65.2 μmol) in DCM (2 mL) was added TFA (1 mL). The reaction mixture was stirred at room temperature for 2 hrs, then concentrated to afford a crude product, which was purified by pre-HPLC to afford Example 1 (9.4 mg, 30.3% yield). MS: calc'd 483 [(M+H)$^+$], measured 483 [(M+H)$^+$]. $^1$H NMR (400 MHz, METHANOL-d$_4$) δ ppm 9.07-8.97 (m, 1H), 8.76-8.62 (m, 1H), 8.19 (d, J=8.1 Hz, 1H), 7.87 (d, J=3.1 Hz, 1H), 7.75-7.62 (m, 1H), 7.40-7.28 (m, 2H), 6.95 (d, J=9.2 Hz, 1H), 4.14-4.02 (m, 1H), 3.89-3.52 (m, 12H), 3.40-3.34 (m, 5H), 3.23-3.09 (m, 2H), 2.37-2.24 (m, 1H), 2.20 (br s, 1H), 1.53 (d, J=6.5 Hz, 3H).

Example 2

5-[(4R,10aS)-4-methyl-8-(2-piperazin-1-ylpyrimidin-5-yl)-1,3,4,6,7,9,10,10a-octahydropyrazino[1,2-d][1,4]diazepin-2-yl]quinoline-8-carbonitrile

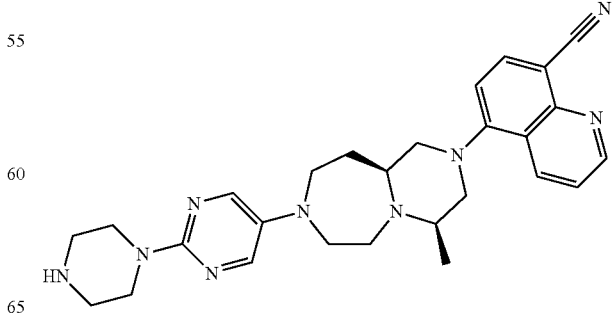

The title compound was prepared in analogy to the preparation of Example 1 by using tert-Butyl 4-(5-bromopyrimidin-2-yl)piperazine-1-carboxylate (CAS: 374930-88-8, BePharm, Catalog: BD28540) instead of tert-butyl 4-(5-bromopyridin-2-yl) piperazine-1-carboxylate in step (a). Example 2 was obtained. MS: calc'd 484 [(M+H)$^+$], measured 484 [(M+H)$^+$]. $^1$H NMR (400 MHz, METHANOL-d$_4$) δ ppm 9.11-9.02 (m, 1H), 8.75-8.66 (m, 1H), 8.32-8.20 (m, 3H), 7.76-7.60 (m, 1H), 7.39 (d, J=8.1 Hz, 1H), 4.22-4.09 (m, 1H), 4.08-3.84 (m, 6H), 3.84-3.65 (m, 4H), 3.61-3.44 (m, 4H), 3.31-3.26 (m, 3H), 3.25-3.09 (m, 2H), 2.45-2.13 (m, 2H), 1.58 (d, J=6.4 Hz, 3H).

Example 3

5-[(4R,10aS)-4-methyl-8-[4-[(2S)-morpholin-2-yl]phenyl]-1,3,4,6,7,9,10,10a-octahydropyrazino[1,2-d][1,4]diazepin-2-yl]quinoline-8-carbonitrile

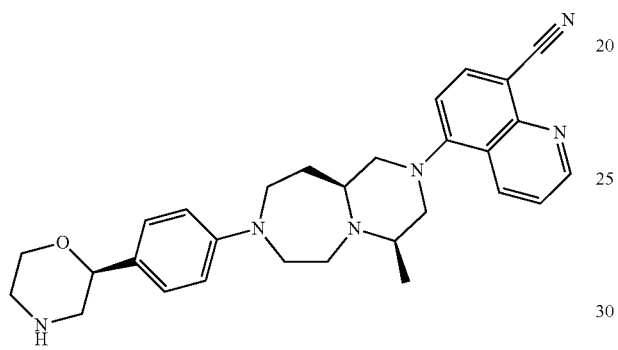

The title compound was prepared in analogy to the preparation of Example 1 by using tert-butyl (2S)-2-(4-bromophenyl)morpholine-4-carboxylate instead of tert-butyl 4-(5-bromopyridin-2-yl) piperazine-1-carboxylate in step (a). Example 3 was obtained. MS: calc'd 483 [(M+H)$^+$], measured 483 [(M+H)$^+$]. $^1$H NMR (400 MHz, METHANOL-d$_4$) δ ppm 9.08-8.99 (m, 1H), 8.75-8.64 (m, 1H), 8.22 (d, J=7.9 Hz, 1H), 7.73-7.63 (m, 1H), 7.38 (d, J=8.1 Hz, 1H), 7.33 (d, J=8.8 Hz, 2H), 6.90 (d, J=8.8 Hz, 2H), 4.72-4.61 (m, 1H), 4.27-4.13 (m, 2H), 4.04-3.59 (m, 9H), 3.54-3.45 (m, 1H), 3.42-3.35 (m, 2H), 3.29-3.07 (m, 4H), 2.39-2.08 (m, 2H), 1.57 (d, J=6.2 Hz, 3H).

Example 4

5-[(4R,10aS)-4-methyl-8-(5,6,7,8-tetrahydro-2,7-naphthyridin-4-yl)-1,3,4,6,7,9,10,10a-octahydropyrazino[1,2-d][1,4]diazepin-2-yl]quinoline-8-carbonitrile

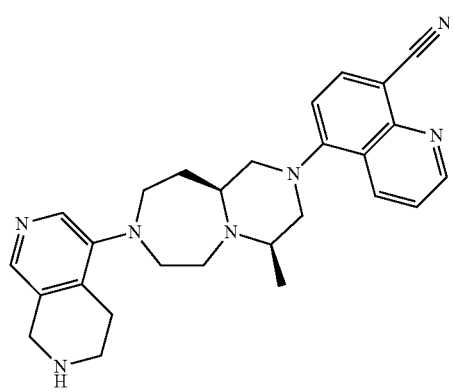 [SMILES: C[C@@H]1CN(c2ccc(C#N)c3ncccc23)C[C@@H]2CCN(c3cncc4c3CCNC4)CCN21]

The title compound was prepared in analogy to the preparation of Example 1 by using tert-butyl 5-bromo-3,4-dihydro-1H-2,7-naphthyridine-2-carboxylate (CAS: 1251012-16-4) instead of tert-butyl 4-(5-bromopyridin-2-yl) piperazine-1-carboxylate in step (a). Example 4 was obtained. MS: calc'd 454 [(M+H)$^+$], measured 454 [(M+H)$^+$]. $^1$H NMR (400 MHz, METHANOL-d$_4$) δ ppm 9.09-9.00 (m, 1H), 8.79-8.69 (m, 1H), 8.51 (s, 1H), 8.38 (s, 1H), 8.23 (d, J=7.9 Hz, 1H), 7.79-7.66 (m, 1H), 7.41 (d, J=8.1 Hz, 1H), 4.55 (s, 2H), 4.17 (br s, 2H), 4.04-3.84 (m, 2H), 3.79-3.53 (m, 7H), 3.48-3.40 (m, 1H), 3.31-3.18 (m, 4H), 2.49-2.34 (m, 1H), 2.28-2.12 (m, 1H), 1.59 (d, J=6.4 Hz, 3H).

Example 5

5-[(4R,10aS)-4-methyl-8-(5,6,7,8-tetrahydro-1,7-naphthyridin-2-yl)-1,3,4,6,7,9,10,10a-octahydropyrazino[1,2-d][1,4]diazepin-2-yl]quinoline-8-carbonitrile

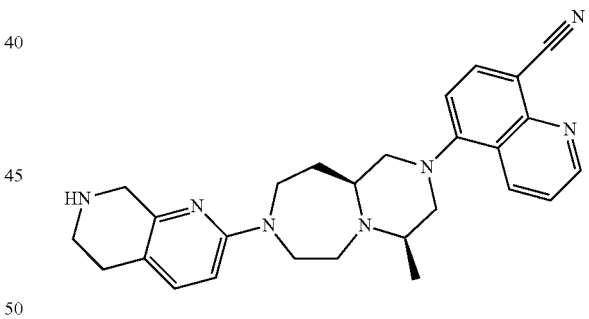

The title compound was prepared in analogy to the preparation of Example 1 by using tert-butyl 2-chloro-6,8-dihydro-5H-1,7-naphthyridine-7-carboxylate (CAS: 1211581-54-2, PharmaBlock, Catalog: PBLJ8189) instead of tert-butyl 4-(5-bromopyridin-2-yl)piperazine-1-carboxylate in step (a). Example 5 was obtained. MS: calc'd 454 [(M+H)$^+$], measured 454 [(M+H)$^+$]. $^1$H NMR (400 MHz, METHANOL-d$_4$) δ ppm 9.04-8.98 (m, 1H), 8.70-8.62 (m, 1H), 8.19 (d, J=7.9 Hz, 1H), 7.74-7.61 (m, 1H), 7.47 (d, J=8.7 Hz, 1H), 7.35 (d, J=7.9 Hz, 1H), 6.71 (d, J=8.7 Hz, 1H), 4.57-4.45 (m, 1H), 4.24 (s, 2H), 4.11-3.99 (m, 1H), 3.88-3.56 (m, 7H), 3.54-3.44 (m, 2H), 3.25 (br t, J=12.0 Hz, 1H), 3.20-3.07 (m, 2H), 3.01 (t, J=6.1 Hz, 2H), 2.40-2.25 (m, 1H), 2.20-2.08 (m, 1H), 1.51 (d, J=6.2 Hz, 3H).

Example 6

5-[(4R,10aS)-4-methyl-8-(5,6,7,8-tetrahydro-1,6-naphthyridin-2-yl)-1,3,4,6,7,9,10,10a-octahydropyrazino[1,2-d][1,4]diazepin-2-yl]quinoline-8-carbonitrile

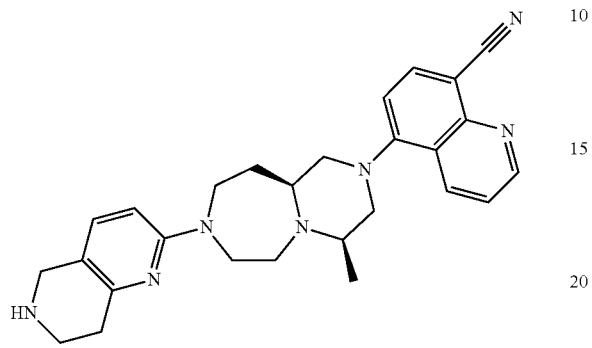

The title compound was prepared in analogy to the preparation of Example 1 by using tert-butyl 2-chloro-5,6,7,8-tetrahydro-1,6-naphthyridine-6-carboxylate (CAS: 1151665-15-4, PharmaBlock, Catalog: PB06675) instead of tert-butyl 4-(5-bromopyridin-2-yl)piperazine-1-carboxylate in step (a). Example 6 was obtained. MS: calc'd 454 [(M+H)$^+$], measured 454 [(M+H)$^+$]. $^1$H NMR (400 MHz, METHANOL-d$_4$) δ ppm 9.04-8.92 (m, 1H), 8.80-8.70 (m, 1H), 8.17 (d, J=8.1 Hz, 1H), 7.81 (d, J=9.4 Hz, 1H), 7.74-7.64 (m, 1H), 7.34 (d, J=7.9 Hz, 1H), 7.24 (d, J=9.7 Hz, 1H), 4.26 (s, 2H), 4.23-4.01 (m, 4H), 3.99-3.78 (m, 3H), 3.71-3.46 (m, 5H), 3.30-3.23 (m, 4H), 2.63-2.47 (m, 1H), 2.27-2.10 (m, 1H), 1.54 (d, J=6.4 Hz, 3H).

Example 7

5-[(4R,10aS)-4-methyl-8-(5,6,7,8-tetrahydro-2,7-naphthyridin-3-yl)-1,3,4,6,7,9,10,10a-octahydropyrazino[1,2-d][1,4]diazepin-2-yl]quinoline-8-carbonitrile

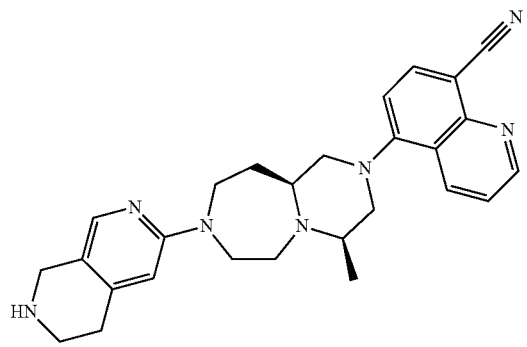 [SMILES: C[C@@H]1CN(c2ccc(C#N)c3ncccc23)C[C@@H]2CCN(c3cc4c(cn3)CNCC4)CCN21]

The title compound was prepared in analogy to the preparation of Example 1 by using tert-butyl 6-chloro-3,4-dihydro-1H-2,7-naphthyridine-2-carboxylate instead of tert-butyl 4-(5-bromopyridin-2-yl)piperazine-1-carboxylate in step (a). Example 7 was obtained. MS: calc'd 454 [(M+H)$^+$], measured 454 [(M+H)$^+$]. $^1$H NMR (400 MHz, METHANOL-d$_4$) δ ppm 9.06-8.98 (m, 1H), 8.73-8.61 (m, 1H), 8.19 (d, J=7.9 Hz, 1H), 8.05 (s, 1H), 7.80-7.62 (m, 1H), 7.35 (d, J=7.9 Hz, 1H), 6.62 (s, 1H), 4.55-4.45 (m, 1H), 4.32 (s, 2H), 4.15-4.03 (m, 1H), 3.86-3.66 (m, 6H), 3.64-3.57 (m, 1H), 3.51 (t, J=6.5 Hz, 2H), 3.31-3.25 (m, 1H), 3.22-3.01 (m, 4H), 2.42-2.26 (m, 1H), 2.22-2.09 (m, 1H), 1.52 (d, J=6.4 Hz, 3H).

Example 8

5-[(4R,10aS)-4-methyl-8-(5,6,7,8-tetrahydro-2,7-naphthyridin-3-ylmethyl)-1,3,4,6,7,9,10,10a-octahydropyrazino[1,2-d][1,4]diazepin-2-yl]quinoline-8-carbonitrile

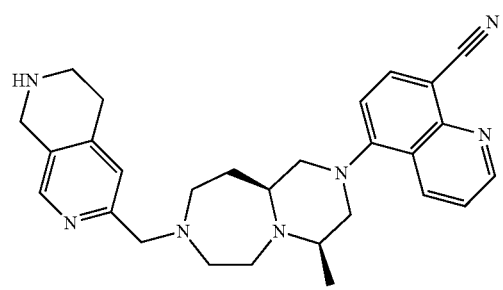 [SMILES: C[C@@H]1CN(c2ccc(C#N)c3ncccc23)C[C@@H]2CCN(Cc3cc4c(cn3)CNCC4)CCN21]

The titled compound was synthesized according to the following scheme:

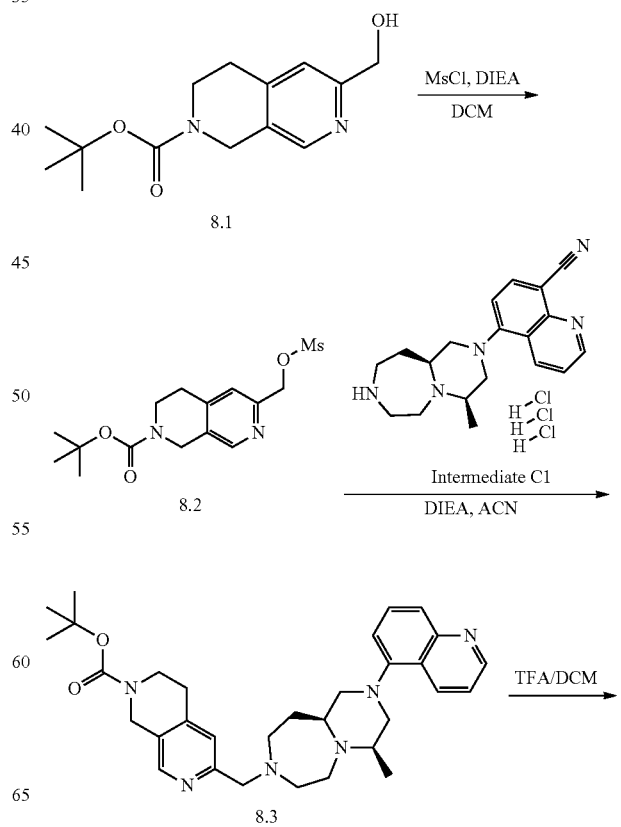

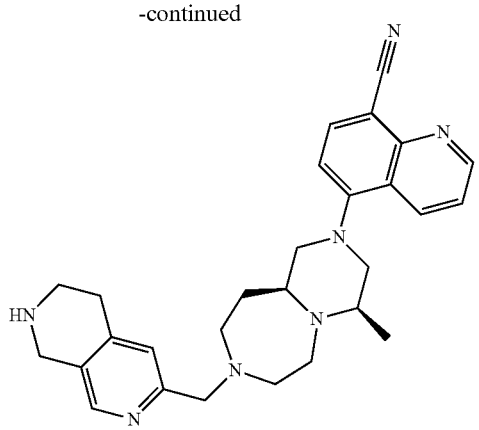

Example 8

Step (a): Preparation of tert-butyl 6-(methylsulfonyloxymethyl)-3,4-dihydro-1H-2,7-naphthyridine-2-carboxylate (Compound 8.2)

To a solution of tert-butyl 6-(hydroxymethyl)-3,4-dihydro-1H-2,7-naphthyridine-2-carboxylate (compound 8.1, 40 mg, 151 μmol) and DIEA (58.7 mg, 454 μmol) in DCM (5 mL) was added dropwise methanesulfonyl chloride (19.1 mg, 166 μmol). The resultant mixture was stirred at room temperature for 2 hrs. The reaction was quenched with aq.NaHCO$_3$, extracted with DCM (20 mL) twice. The combined organic layer was washed with brine, dried over Na$_2$SO$_4$, filtered and the filtrate was concentrated to afford compound 8.2 (52 mg, 100% yield) which was used directly for the next step without further purification. MS: calc'd 343 [(M+H)$^+$], measured 343 [(M+H)$^+$].

Step (b): Preparation of tert-butyl 6-[[(4R,10aS)-2-(8-cyano-5-quinolyl)-4-methyl-1,3,4,6,7,9,10,10a-octahydropyrazino[1,2-d][1,4]diazepin-8-yl]methyl]-3,4-dihydro-1H-2,7-naphthyridine-2-carboxylate (Compound 8.3)

To a solution of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1, 80 mg, 186 μmol) in acetonitrile (10 mL) was added tert-butyl 6-(methylsulfonyloxymethyl)-3,4-dihydro-1H-2,7-naphthyridine-2-carboxylate (compound 8.2, 52 mg, 152 μmol) and DIEA (98.1 mg, 759 μmol). The resultant mixture was stirred at reflux for 5 hrs, then concentrated, the residue was purified by flash chromatography to afford compound 8.3 (49 mg, 56.8% yield). MS: calc'd 568 [(M+H)$^+$], measured 568 [(M+H)$^+$].

Step (c): Preparation of 5-[(4R,10aS)-4-methyl-8-(5,6,7,8-tetrahydro-2,7-naphthyridin-3-ylmethyl)-1,3,4,6,7,9,10,10a-octahydropyrazino[1,2-d][1,4]diazepin-2-yl]quinoline-8-carbonitrile (Example 8)

To a solution of tert-butyl 6-[[(4R,10aS)-2-(8-cyano-5-quinolyl)-4-methyl-1,3,4,6,7,9,10,10a-octahydropyrazino[1,2-d][1,4]diazepin-8-yl]methyl]-3,4-dihydro-1H-2,7-naphthyridine-2-carboxylate (compound 8.3, 50 mg, 88.1 μmol) in DCM (10 mL) was added TFA (3 mL). The reaction mixture was stirred at room temperature for 2 hrs, then concentrated to afford a crude product, which was purified by pre-HPLC to afford Example 8 (18 mg, 43.7% yield). MS: calc'd 468 [(M+H)$^+$], measured 468 [(M+H)$^+$]. $^1$H NMR (400 MHz, METHANOL-d$_4$) δ ppm 9.01-8.97 (m, 1H), 8.67-8.59 (m, 1H), 8.37 (s, 1H), 8.16 (d, J=8.1 Hz, 1H), 7.74-7.61 (m, 1H), 7.38 (s, 1H), 7.25 (d, J=8.1 Hz, 1H), 4.22 (s, 2H), 4.03 (br s, 2H), 3.45-3.36 (m, 3H), 3.29-3.24 (m, 1H), 3.19-2.97 (m, 8H), 2.92-2.70 (m, 4H), 2.14-1.99 (m, 1H), 1.90-1.78 (m, 1H), 1.22 (d, J=6.1 Hz, 3H).

Example 9

5-[(4R,10aS)-4-methyl-8-(5,6,7,8-tetrahydro-2,6-naphthyridin-3-ylmethyl)-1,3,4,6,7,9,10,10a-octahydropyrazino[1,2-d][1,4]diazepin-2-yl]quinoline-8-carbonitrile

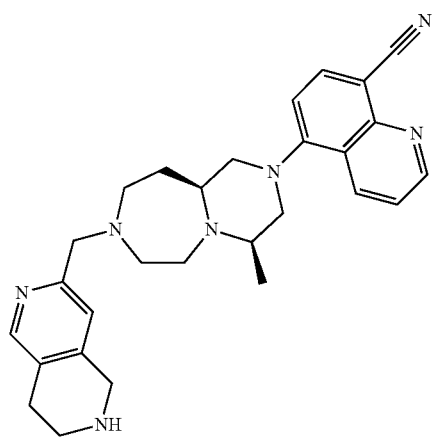 [SMILES: C[C@@H]1CN(c2ccc(C#N)c3ncccc23)C[C@@H]2CCN(Cc3cc4c(cn3)CCNC4)CCN21]

The title compound was prepared in analogy to the preparation of Example 8 by using tert-butyl 7-(hydroxymethyl)-3,4-dihydro-1H-2,6-naphthyridine-2-carboxylate instead of tert-butyl 6-(hydroxymethyl)-3,4-dihydro-1H-2,7-naphthyridine-2-carboxylate in step (a). Example 9 was obtained. MS: calc'd 468 [(M+H)$^+$], measured 468 [(M+H)$^+$]. $^1$H NMR (400 MHz, METHANOL-d$_4$) δ ppm 9.06-8.98 (m, 1H), 8.69-8.64 (m, 1H), 8.62 (s, 1H), 8.19 (d, J=8.1 Hz, 1H), 7.72-7.65 (m, 1H), 7.43 (s, 1H), 7.32 (d, J=8.1 Hz, 1H), 4.49 (d, J=6.6 Hz, 4H), 3.82-3.74 (m, 1H), 3.67-3.48 (m, 10H), 3.41-3.35 (m, 1H), 3.21 (t, J=6.2 Hz, 2H), 3.13-3.06 (m, 1H), 3.03-2.94 (m, 1H), 2.31-2.11 (m, 2H), 1.39 (d, J=6.1 Hz, 3H).

Example 10

5-[(4R,10aS)-4-methyl-8-(5,6,7,8-tetrahydro-1,6-naphthyridin-3-ylmethyl)-1,3,4,6,7,9,10,10a-octahydropyrazino[1,2-d][1,4]diazepin-2-yl]quinoline-8-carbonitrile

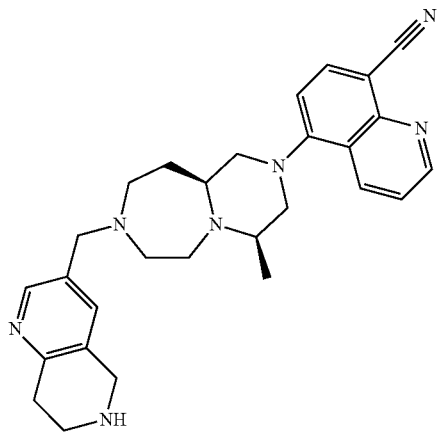 [SMILES: C[C@@H]1CN(c2ccc(C#N)c3ncccc23)C[C@@H]2CCN(Cc3cnc4c(c3)CNCC4)CCN21]

The title compound was prepared in analogy to the preparation of Example 8 by using tert-butyl 3-(hydroxymethyl)-7,8-dihydro-5H-1,6-naphthyridine-6-carboxylateinstead instead of tert-butyl 6-(hydroxymethyl)-3,4-dihydro-1H-2,7-naphthyridine-2-carboxylate in step (a). Example 10 was obtained. MS: calc'd 468 [(M+H)$^+$], measured 468 [(M+H)$^+$]. $^1$H NMR (400 MHz, METHANOL-d$_4$) δ ppm 9.07-8.98 (m, 1H), 8.72-8.60 (m, 2H), 8.19 (d, J=8.1 Hz, 1H), 7.95 (d, J=1.7 Hz, 1H), 7.72-7.62 (m, 1H), 7.34 (d, J=8.1 Hz, 1H), 4.51 (s, 2H), 4.35 (s, 2H), 3.97-3.75 (m, 2H), 3.73-3.40 (m, 10H), 3.32-3.25 (m, 2H), 3.19-3.00 (m, 2H), 2.29-2.16 (m, 2H), 1.43 (d, J=6.2 Hz, 3H).

Example 11

5-[(4R,10aS)-4-methyl-8-(1,2,3,4-tetrahydroisoquinolin-6-ylmethyl)-1,3,4,6,7,9,10,10a-octahydropyrazino[1,2-d][1,4]diazepin-2-yl]quinoline-8-carbonitrile

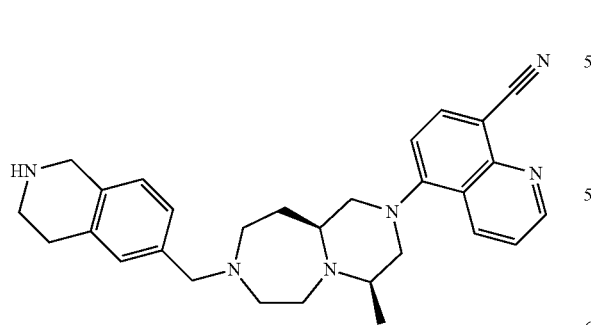

The title compound was prepared in analogy to the preparation of Example 8 by using tert-butyl 6-(bromomethyl)-3,4-dihydro-1H-isoquinoline-2-carboxylate instead of tert-butyl 6-(methylsulfonyloxymethyl)-3,4-dihydro-1H-2,7-naphthyridine-2-carboxylate (compound 8.2) in step (b). Example 11 was obtained. MS: calc'd 467 [(M+H)$^+$], measured 467 [(M+H)$^+$]. $^1$H NMR (400 MHz, METHANOL-d$_4$) δ ppm 9.05-8.95 (m, 1H), 8.67-8.57 (m, 1H), 8.15 (d, J=8.1 Hz, 1H), 7.72-7.60 (m, 1H), 7.51-7.42 (m, 2H), 7.36 (d, J=7.8 Hz, 1H), 7.24 (d, J=8.1 Hz, 1H), 4.43 (s, 2H), 4.33 (s, 2H), 3.61-3.48 (m, 3H), 3.47-3.35 (m, 5H), 3.30-3.08 (m, 5H), 3.00-2.81 (m, 2H), 2.74 (t, J=11.2 Hz, 1H), 2.30-2.14 (m, 1H), 2.00-1.86 (m, 1H), 1.23 (d, J=6.1 Hz, 3H).

Example 12

5-[(4R,10aS)-4-methyl-8-(1,2,3,4-tetrahydroisoquinolin-7-ylmethyl)-1,3,4,6,7,9,10,10a-octahydropyrazino[1,2-d][1,4]diazepin-2-yl]quinoline-8-carbonitrile

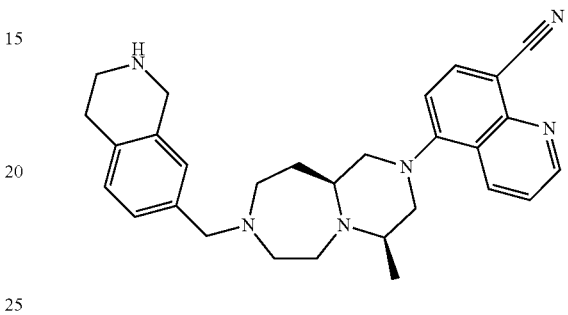

The title compound was prepared in analogy to the preparation of Example 8 by using tert-butyl 7-(hydroxymethyl)-3,4-dihydro-1H-isoquinoline-2-carboxylate instead of tert-butyl 6-(hydroxymethyl)-3,4-dihydro-1H-2,7-naphthyridine-2-carboxylate in step (a). Example 12 was obtained. MS: calc'd 467 [(M+H)$^+$], measured 467 [(M+H)$^+$]. $^1$H NMR (400 MHz, METHANOL-d$_4$) δ ppm 9.04-8.96 (m, 1H), 8.67-8.59 (m, 1H), 8.15 (d, J=8.1 Hz, 1H), 7.67-7.58 (m, 1H), 7.52-7.45 (m, 1H), 7.42-7.35 (m, 2H), 7.25 (d, J=8.1 Hz, 1H), 4.43 (s, 2H), 4.34 (s, 2H), 3.55 (t, J=6.4 Hz, 3H), 3.46-3.35 (m, 5H), 3.28-3.10 (m, 5H), 2.99-2.85 (m, 2H), 2.74 (t, J=11.2 Hz, 1H), 2.33-2.15 (m, 1H), 2.04-1.86 (m, 1H), 1.23 (d, J=6.1 Hz, 3H).

Example 13

5-[(4R,10aS)-4-methyl-8-[(5-piperazin-1-ylpyrimidin-2-yl)methyl]-1,3,4,6,7,9,10,10a-octahydropyrazino[1,2-d][1,4]diazepin-2-yl]quinoline-8-carbonitrile

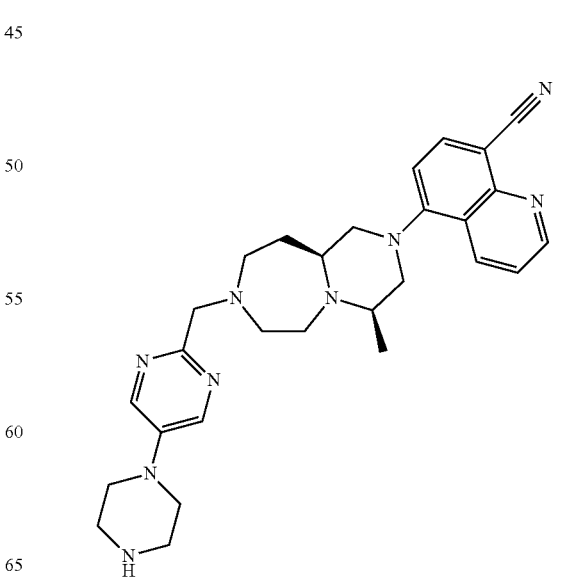

The titled compound was synthesized according to the following scheme:

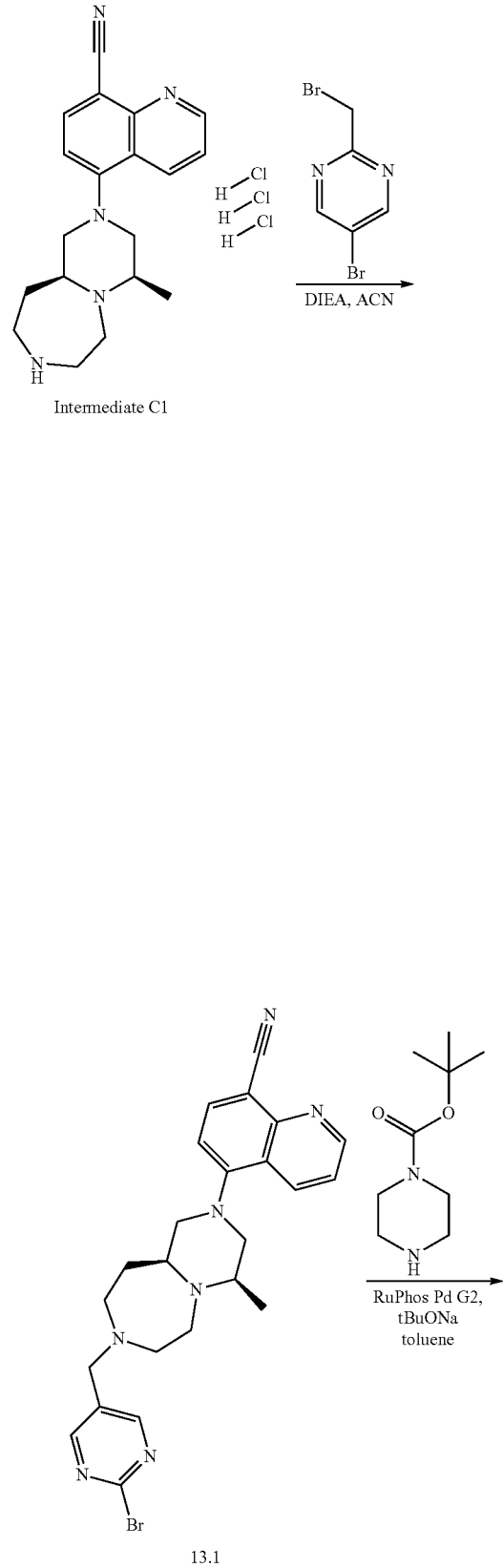

Intermediate C1

13.1

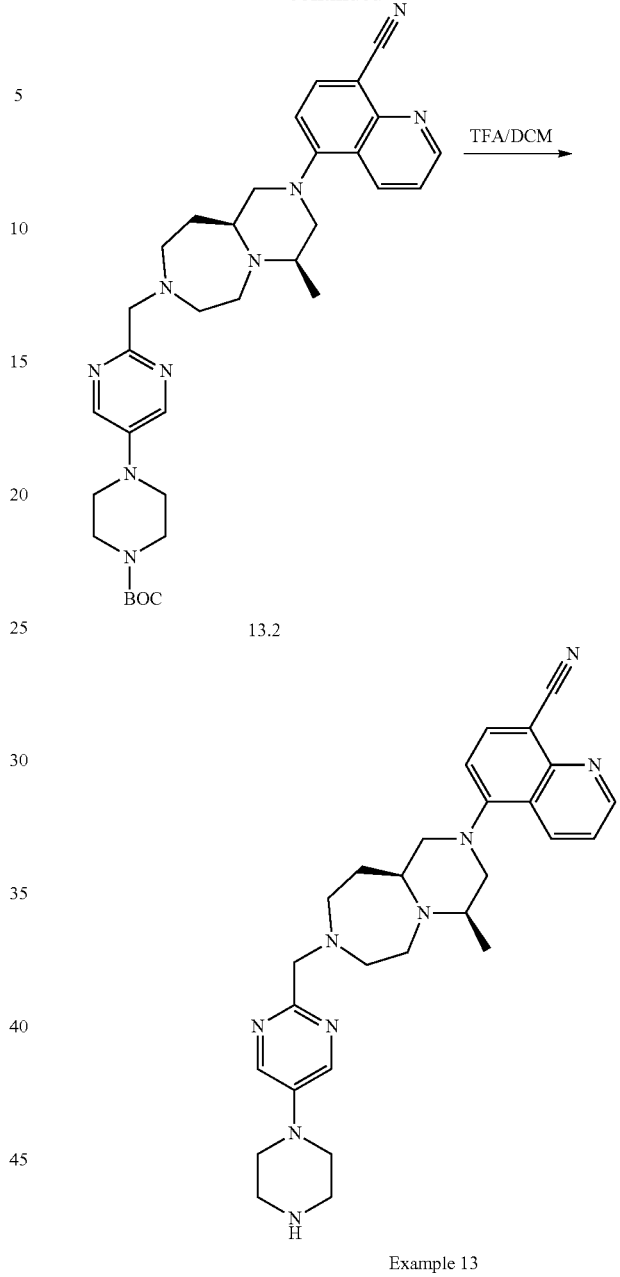

13.2

Example 13

Step (a): Preparation of 5-[(4R,10aS)-8-[(5-bromopyrimidin-2-yl)methyl]-4-methyl-1,3,4,6,7,9,10,10a-octahydropyrazino[1,2-d][1,4]diazepin-2-yl]quinoline-8-carbonitrile (Compound 13.1)

To a solution of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1, 90 mg, 209 μmol) in acetonitrile (8 mL) was added 5-bromo-2-(bromomethyl)pyrimidine (CAS: 1193116-74-3, BePharm, Catalog: BD266661, 105 mg, 418 μmol) and DIPEA (135 mg, 1.04 mmol). The mixture was stirred at reflux for 2 hrs. The reaction mixture was concentrated, the residue was purified by flash chromatography to afford compound 13.1 (32 mg, 31.1% yield). MS: calc'd 492,494 [(M+H)$^+$], measured 492,494 [(M+H)$^+$].

Step (b): Preparation of tert-butyl 4-[2-[[(4R,10aS)-2-(8-cyano-5-quinolyl)-4-methyl-1,3,4,6,7,9,10,10a-octahydropyrazino[1,2-d][1,4]diazepin-8-yl]methyl]pyrimidin-5-yl]piperazine-1-carboxylate (Compound 13.2)

To a solution of 5-[(4R,10aS)-8-[(5-bromopyrimidin-2-yl)methyl]-4-methyl-1,3,4,6,7,9,10,10a-octahydropyrazino[1,2-d][1,4]diazepin-2-yl]quinoline-8-carbonitrile (compound 13.1, 30 mg, 60.9 μmol) in toluene (5 ml) was added tert-butyl piperazine-1-carboxylate (22.7 mg, 122 μmol), tBuONa (11.7 mg, 122 μmol) and RuPhos Pd G2 (4.73 mg, 6.09 μmol). The reaction mixture was stirred at 100° C. overnight. The mixture was cooled to room temperature, diluted with water (20 mL) and extracted with EA (20 mL) for three times. The combined organic layer was washed with brine, dried over $Na_2SO_4$, filtered and concentrated in vacuo. The residue was purified by flash chromatography (silica gel 20 g, 0% to 100% EtOAc in PE) to afford compound 13.2 (20 mg, 54.9% yield). MS: calc'd 598 [(M+H)$^+$], measured 598 [(M+H)$^+$].

Step (c): Preparation of 5-[(4R,10aS)-4-methyl-8-[(5-piperazin-1-ylpyrimidin-2-yl)methyl]-1,3,4,6,7,9,10,10a-octahydropyrazino[1,2-d][1,4]diazepin-2-yl]quinoline-8-carbonitrile (Example 13)

To a solution of tert-butyl 4-[2-[[(4R,10aS)-2-(8-cyano-5-quinolyl)-4-methyl-1,3,4,6,7,9, 10,10a-octahydropyrazino[1,2-d][1,4]diazepin-8-yl]methyl]pyrimidin-5-yl]piperazine-1-carboxylate (compound 13.2, 20 mg, 33.5 μmol) in DCM (5 mL) was added TFA (2 mL). The reaction mixture was stirred at room temperature for 2 hrs, then concentrated to afford a crude product, which was purified by pre-HPLC to afford Example 13 (11 mg, 66.0% yield). MS: calc'd 498 [(M+H)$^+$], measured 498 [(M+H)$^+$]. $^1$H NMR (400 MHz, METHANOL-d$_4$) δ ppm 9.11-8.94 (m, 1H), 8.72-8.60 (m, 3H), 8.16 (d, J=7.9 Hz, 1H), 7.77-7.61 (m, 1H), 7.26 (d, J=8.1 Hz, 1H), 4.48 (s, 2H), 3.65-3.36 (m, 15H), 3.30-3.09 (m, 2H), 3.06-2.96 (m, 1H), 2.95-2.85 (m, 1H), 2.84-2.71 (m, 1H), 2.22 (br d, J=7.2 Hz, 1H), 1.98 (br d, J=7.5 Hz, 1H), 1.27 (d, J=6.1 Hz, 3H).

Example 14

5-[(4R,10aS)-4-methyl-8-[(2-piperazin-1-ylpyrimidin-5-yl)methyl]-1,3,4,6,7,9,10,10a-octahydropyrazino[1,2-d][1,4]diazepin-2-yl]quinoline-8-carbonitrile

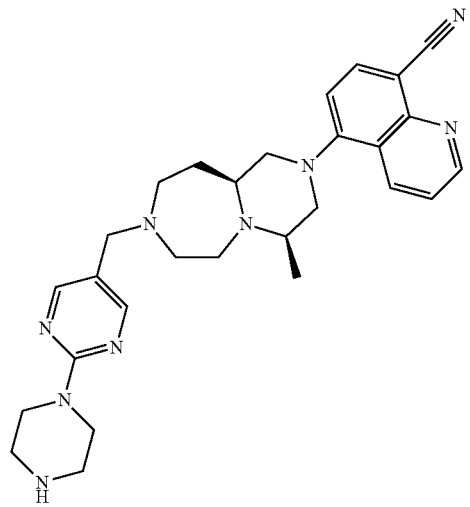 [SMILES: C[C@@H]1CN(c2ccc(C#N)c3ncccc23)C[C@@H]2CCN(Cc3cnc(N4CCNCC4)nc3)CCN21]

The titled compound was synthesized according to the following scheme:

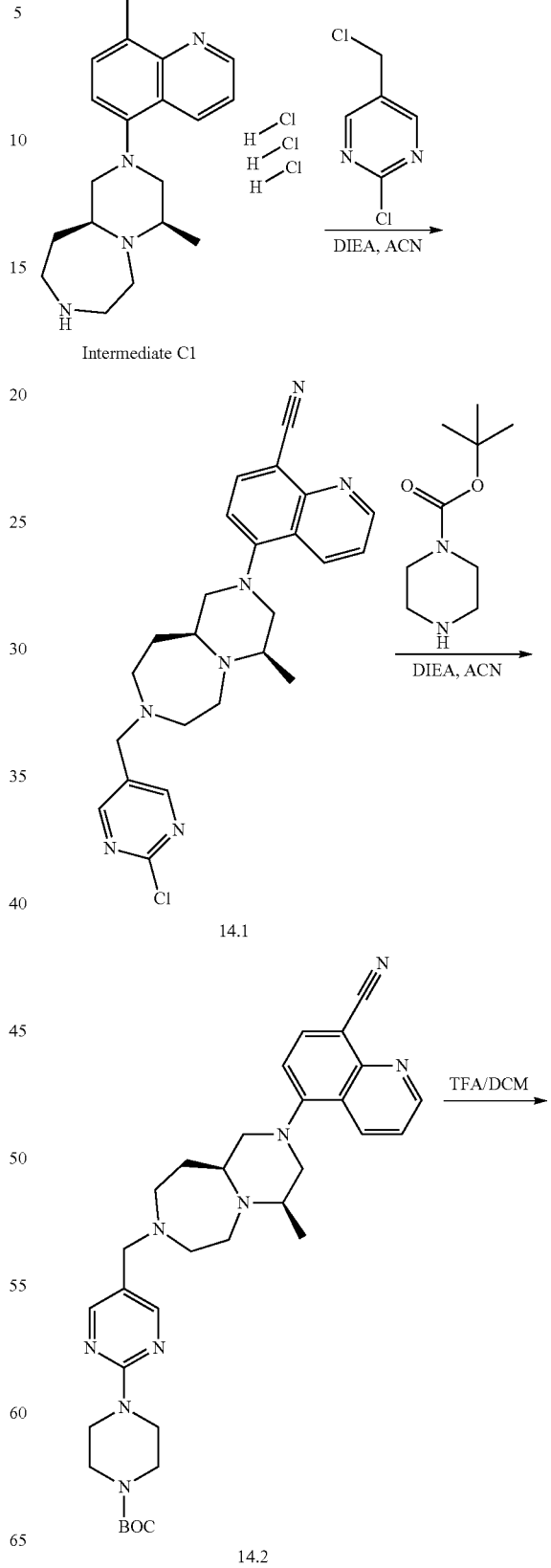

47
-continued

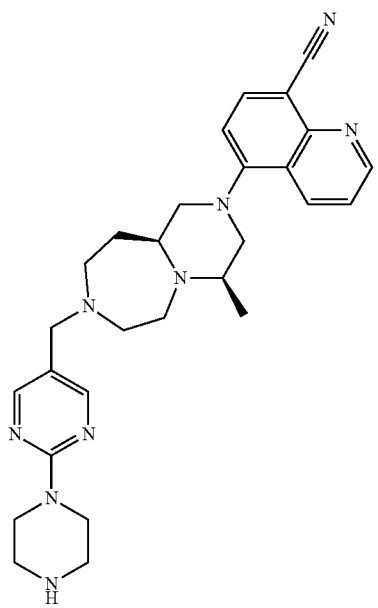

Example 14

Step (a): Preparation of 5-[(4R,10aS)-8-[(2-chloro-pyrimidin-5-yl)methyl]-4-methyl-1,3,4,6,7,9,10,10a-octahydropyrazino[1,2-d][1,4]diazepin-2-yl]quinoline-8-carbonitrile (Compound 14.1)

To a solution of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1, 90 mg, 209 µmol) in acetonitrile (8 mL) was added 2-chloro-5-(chloromethyl)pyrimidine (CAS: 148406-13-7, BePharm, Catalog: BD223762, 68.1 mg, 418 µmol) and DIEA (135 mg, 1.04 mmol). The mixture was stirred at reflux for 2 hrs, then concentrated, the residue was purified by flash chromatography to afford compound 14.1 (25 mg, 26.7% yield). MS: calc'd 448,450 [(M+H)$^+$], measured 448,450 [(M+H)$^+$].

Step (b): Preparation of tert-butyl 4-[5-[[(4R,10aS)-2-(8-cyano-5-quinolyl)-4-methyl-1,3,4,6,7,9,10,10a-octahydropyrazino[1,2-d][1,4]diazepin-2-yl]methyl]pyrimidin-2-yl]piperazine-1-carboxylate (Compound 14.2)

To a 10 mL microwave vial was added 5-[(4R,10aS)-8-[(2-chloropyrimidin-5-yl)methyl]-4-methyl-1,3,4,6,7,9,10,10a-octahydropyrazino[1,2-d][1,4]diazepin-2-yl]quinoline-8-carbonitrile (compound 14.1, 20 mg, 44.6 µmol), tert-butyl piperazine-1-carboxylate (16.6 mg, 89.3 µmol) and DIEA (5.77 mg, 7.8 µl, 44.6 µmol) in acetonitrile (2 ml). The vial was capped and heated in the microwave at 120° C. for 8 h. The mixture was concentrated to afford compound 14.2 (26.7 mg, 100% yield), which was used directly to the next step. 598 [(M+H)$^+$], measured 598 [(M+H)$^+$].

48

Step (c): Preparation of 5-[(4R,10aS)-4-methyl-8-[(2-piperazin-1-ylpyrimidin-5-yl)methyl]-1,3,4,6,7,9,10,10a-octahydropyrazino[1,2-d][1,4]diazepin-2-yl]quinoline-8-carbonitrile (Example 14)

To a solution of tert-butyl 4-[5-[[(4R,10aS)-2-(8-cyano-5-quinolyl)-4-methyl-1,3,4,6,7,9,10,10a-octahydropyrazino[1,2-d][1,4]diazepin-8-yl]methyl]pyrimidin-2-yl]piperazine-1-carboxylate (compound 14.2, 20 mg, 33.5 µmol) in DCM (6 mL) was added TFA (2 mL). The reaction mixture was stirred at room temperature for 2 hrs, then concentrated to afford a crude product, which was purified by pre-HPLC to afford Example 14 (15 mg, 90.1% yield). MS: calc'd 498 [(M+H)$^+$], measured 498 [(M+H)$^+$]. $^1$H NMR (400 MHz, METHANOL-$d_4$) δ ppm 9.05-8.97 (m, 1H), 8.65-8.60 (m, 1H), 8.55 (s, 2H), 8.16 (d, J=7.9 Hz, 1H), 7.68-7.60 (m, 1H), 7.26 (d, J=7.9 Hz, 1H), 4.21 (s, 2H), 4.18-4.11 (m, 4H), 3.52-3.36 (m, 6H), 3.31-3.13 (m, 5H), 2.99-2.85 (m, 2H), 2.81-2.71 (m, 1H), 2.30-2.12 (m, 1H), 2.02-1.84 (m, 1H), 1.26 (d, J=6.1 Hz, 3H).

Example 15

5-[(4R,10aS)-4-methyl-8-[(5-piperazin-1-ylpyrazin-2-yl)methyl]-1,3,4,6,7,9,10,10a-octahydropyrazino[1,2-d][1,4]diazepin-2-yl]quinoline-8-carbonitrile

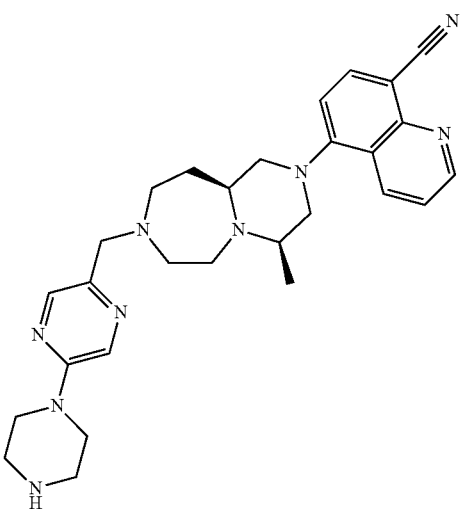 [SMILES: C[C@@H]1CN(c2ccc(C#N)c3ncccc23)C[C@@H]2CCN(Cc3cnc(N4CCNCC4)cn3)CCN21]

The title compound was prepared in analogy to the preparation of Example 14 by using 2-(bromomethyl)-5-chloropyrazine (CAS: 1433707-80-2, BePharm, Catalog: BD00735886) instead of 2-chloro-5-(chloromethyl)pyrimidine in step (a). Example 15 was obtained. MS: calc'd 498 [(M+H)$^+$], measured 498 [(M+H$^+$)]. $^1$H NMR (400 MHz, METHANOL-$d_4$) δ ppm 9.06-8.98 (m, 1H), 8.70-8.63 (m, 1H), 8.45 (d, J=1.3 Hz, 1H), 8.30 (d, J=1.3 Hz, 1H), 8.18 (d, J=8.1 Hz, 1H), 7.73-7.60 (m, 1H), 7.31 (d, J=8.1 Hz, 1H), 4.45 (s, 2H), 4.05-3.93 (m, 4H), 3.82-3.42 (m, 10H), 3.41-3.36 (m, 4H), 3.09 (d, J=11.9 Hz, 1H), 3.01-2.92 (m, 1H), 2.31-2.09 (m, 2H), 1.37 (d, J=6.2 Hz, 3H).

Example 16

5-[(4R,10aS)-4-methyl-8-[(5-piperazin-1-yl-3-pyridyl)methyl]-1,3,4,6,7,9,10,10a-octahydropyrazino[1,2-d][1,4]diazepin-2-yl]quinoline-8-carbonitrile

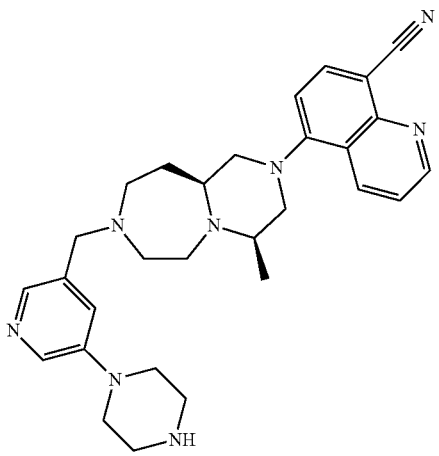 [SMILES: C[C@@H]1CN(c2ccc(C#N)c3ncccc23)C[C@@H]2CCN(Cc3cncc(N4CCNCC4)c3)CCN21]

The title compound was prepared in analogy to the preparation of Example 13 by using 3-bromo-5-(bromomethyl)pyridine (CAS: 145743-85-7, BePharm, Catalog: BD162034) instead of 5-bromo-2-(bromomethyl)pyrimidine in step (a). Example 16 was obtained. MS: calc'd 497 [(M+H)$^+$], measured 497 [(M+H)$^+$]. $^1$H NMR (400 MHz, METHANOL-d$_4$) δ ppm 9.02-8.96 (m, 1H), 8.70-8.60 (m, 1H), 8.40 (d, J=2.7 Hz, 1H), 8.22 (d, J=1.5 Hz, 1H), 8.16 (d, J=7.9 Hz, 1H), 7.70-7.60 (m, 2H), 7.27 (d, J=8.1 Hz, 1H), 4.28 (s, 2H), 3.63-3.56 (m, 4H), 3.55-3.36 (m, 10H), 3.33-3.19 (m, 3H), 3.11-3.01 (m, 1H), 3.00-2.90 (m, 1H), 2.89-2.74 (m, 1H), 2.28-2.14 (m, 1H), 2.08-1.94 (m, 1H), 1.27 (d, J=6.2 Hz, 3H).

Example 17

5-[(4R,10aS)-4-methyl-8-[(6-piperazin-1-yl-3-pyridyl)methyl]-1,3,4,6,7,9,10,10a-octahydropyrazino[1,2-d][1,4]diazepin-2-yl]quinoline-8-carbonitrile

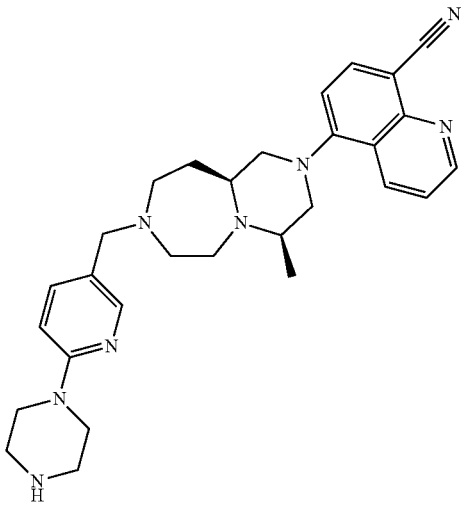 [SMILES: C[C@@H]1CN(c2ccc(C#N)c3ncccc23)C[C@@H]2CCN(Cc3ccc(N4CCNCC4)nc3)CCN21]

The title compound was prepared in analogy to the preparation of Example 13 by using 2-chloro-5-(chloromethyl)pyridine (CAS: 70258-18-3, TCI, Catalog: C1628) instead of 5-bromo-2-(bromomethyl)pyrimidine in step (a). Example 17 was obtained. MS: calc'd 497 [(M+H)$^+$], measured 497 [(M+H)$^+$]. $^1$H NMR (400 MHz, METHANOL-d$_4$) δ ppm 9.04-8.99 (m, 1H), 8.73-8.61 (m, 1H), 8.33 (d, J=2.2 Hz, 1H), 8.18 (d, J=7.9 Hz, 1H), 7.91-7.78 (m, 1H), 7.73-7.62 (m, 1H), 7.32 (d, J=8.1 Hz, 1H), 7.04 (d, J=8.9 Hz, 1H), 4.37 (s, 2H), 4.00-3.89 (m, 4H), 3.84 (br d, J=16.8 Hz, 1H), 3.71-3.47 (m, 8H), 3.46-3.34 (m, 5H), 3.17-3.07 (m, 1H), 3.06-2.97 (m, 1H), 2.36-2.14 (m, 2H), 1.39 (d, J=6.1 Hz, 3H).

Example 18

5-[(4R,10aS)-4-methyl-8-[(6-piperazin-1-yl-2-pyridyl)methyl]-1,3,4,6,7,9,10,10a-octahydropyrazino[1,2-d][1,4]diazepin-2-yl]quinoline-8-carbonitrile

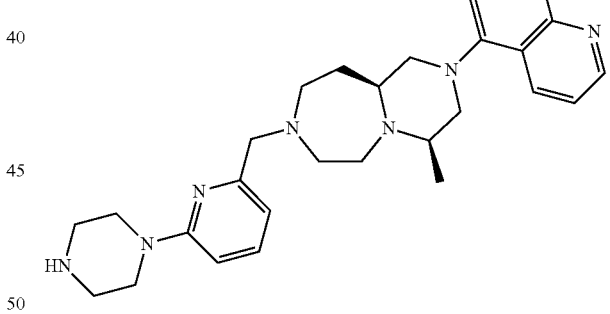

The title compound was prepared in analogy to the preparation of Example 13 by using 2-chloro-6-(chloromethyl)pyridine (CAS: 78846-88-5, BePharm, Catalog: BD120582) instead of 5-bromo-2-(bromomethyl)pyrimidine in step (a). Example 18 was obtained. MS: calc'd 497 [(M+H)$^+$], measured 497 [(M+H)$^+$]. $^1$H NMR (400 MHz, METHANOL-d$_4$) δ ppm 9.06-8.93 (m, 1H), 8.68-8.58 (m, 1H), 8.15 (d, J=7.9 Hz, 1H), 7.78-7.68 (m, 1H), 7.68-7.58 (m, 1H), 7.24 (d, J=8.1 Hz, 1H), 6.98 (d, J=8.6 Hz, 1H), 6.89 (d, J=7.2 Hz, 1H), 4.42 (s, 2H), 3.99-3.86 (m, 4H), 3.72-3.49 (m, 3H), 3.47-3.34 (m, 8H), 3.19-3.11 (m, 1H), 3.09-3.01 (m, 1H), 3.00-2.92 (m, 1H), 2.91-2.81 (m, 1H), 2.77-2.64 (m, 1H), 2.35-2.17 (m, 1H), 2.05-1.91 (m, 1H), 1.23 (d, J=6.1 Hz, 3H).

Example 19

5-[(4R,10aS)-4-methyl-8-[(5-piperazin-1-yl-2-pyridyl)methyl]-1,3,4,6,7,9,10,10a-octahydropyrazino[1,2-d][1,4]diazepin-2-yl]quinoline-8-carbonitrile

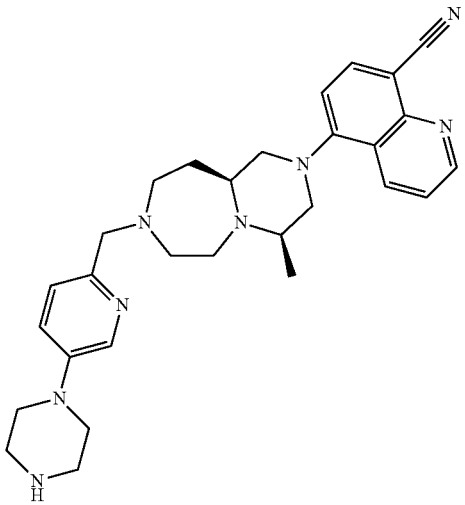 [SMILES: C[C@@H]1CN(c2ccc(C#N)c3ncccc23)C[C@@H]2CCN(Cc3ccc(N4CCNCC4)cn3)CCN21]

The title compound was prepared in analogy to the preparation of Example 13 by using 5-bromo-2-(chloromethyl)pyridine (CAS: 168823-76-5, BePharm, Catalog: BD223172) instead of 5-bromo-2-(bromomethyl)pyrimidine in step (a). Example 19 was obtained. MS: calc'd 497 [(M+H)$^+$], measured 497 [(M+H)$^+$]. $^1$H NMR (400 MHz, METHANOL-d$_4$) δ ppm 9.14-8.95 (m, 1H), 8.71-8.62 (m, 1H), 8.48 (d, J=2.8 Hz, 1H), 8.19 (d, J=7.9 Hz, 1H), 7.75-7.59 (m, 2H), 7.52 (d, J=8.7 Hz, 1H), 7.31 (d, J=8.1 Hz, 1H), 4.40 (s, 2H), 3.65 (br s, 1H), 3.61-3.36 (m, 16H), 3.28-3.17 (m, 1H), 3.08-2.97 (m, 1H), 2.96-2.84 (m, 1H), 2.21 (br s, 1H), 2.11 (br s, 1H), 1.35 (d, J=6.1 Hz, 3H).

Example 20

5-[(4R,10aS)-8-[[5-[(3R,4S)-3-amino-4-fluoro-pyrrolidin-1-yl]-2-pyridyl]methyl]-4-methyl-1,3,4,6,7,9,10,10a-octahydropyrazino[1,2-d][1,4]diazepin-2-yl]quinoline-8-carbonitrile

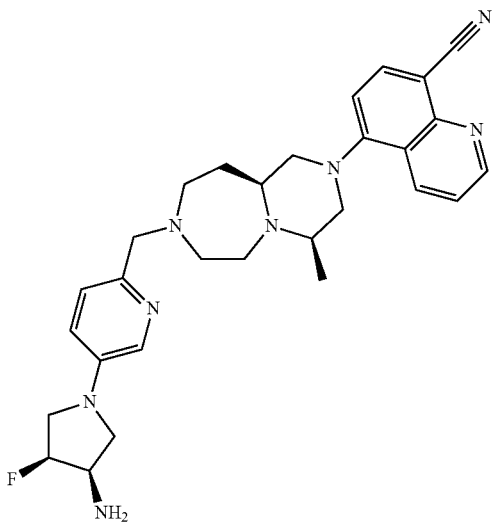 [SMILES: C[C@@H]1CN(c2ccc(C#N)c3ncccc23)C[C@@H]2CCN(Cc3ccc(N4C[C@@H](N)[C@@H](F)C4)cn3)CCN21]

The title compound was prepared in analogy to the preparation of Example 19 by using tert-butyl N-[(3R,4S)-4-fluoropyrrolidin-3-yl]carbamate (CAS: 1033718-91-0, PharmaBlock, Catalog: PB09204) instead of tert-butyl piperazine-1-carboxylate in step (b). Example 20 was obtained. MS: calc'd 515 [(M+H)$^+$], measured 515 [(M+H)$^+$]. $^1$H NMR (400 MHz, METHANOL-d$_4$) δ ppm 9.04-8.92 (m, 1H), 8.66-8.58 (m, 1H), 8.15 (d, J=7.9 Hz, 1H), 8.10 (d, J=2.8 Hz, 1H), 7.71-7.59 (m, 1H), 7.45 (d, J=8.6 Hz, 1H), 7.25 (d, J=8.1 Hz, 1H), 7.19-7.10 (m, 1H), 5.64-5.43 (m, 1H), 4.37 (s, 2H), 4.29-4.15 (m, 1H), 3.95 (t, J=8.9 Hz, 1H), 3.89-3.84 (m, 1H), 3.79 (d, J=2.0 Hz, 1H), 3.61-3.35 (m, 8H), 3.30-3.22 (m, 1H), 3.21-3.12 (m, 1H), 3.07-2.87 (m, 2H), 2.83-2.70 (m, 1H), 2.31-2.17 (m, 1H), 2.03-1.92 (m, 1H), 1.26 (d, J=6.1 Hz, 3H).

Example 21

5-[(4R,10aS)-8-[[5-[(6R)-6-amino-1,4-oxazepan-4-yl]-2-pyridyl]methyl]-4-methyl-1,3,4,6,7,9,10,10a-octahydropyrazino[1,2-d][1,4]diazepin-2-yl]quinoline-8-carbonitrile

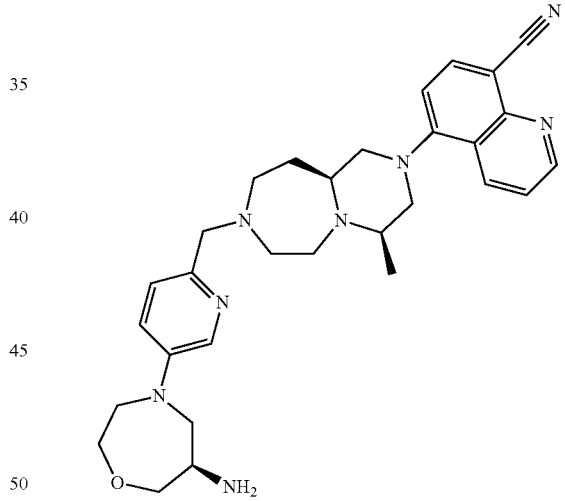

The title compound was prepared in analogy to the preparation of Example 19 by using tert-butyl N-[(6R)-1,4-oxazepan-6-yl]carbamate (PharmaBlock, Catalog: PB97932) instead of tert-butyl piperazine-1-carboxylate in step (b). Example 21 was obtained. MS: calc'd 527 [(M+H)$^+$], measured 527 [(M+H)$^+$]. $^1$H NMR (400 MHz, METHANOL-d$_4$) δ ppm 9.06-8.91 (m, 1H), 8.67-8.59 (m, 1H), 8.34 (d, J=2.8 Hz, 1H), 8.15 (d, J=7.9 Hz, 1H), 7.75-7.59 (m, 1H), 7.51-7.31 (m, 2H), 7.25 (d, J=8.1 Hz, 1H), 4.36 (s, 2H), 4.23-4.15 (m, 1H), 4.12-4.05 (m, 1H), 4.04-3.91 (m, 2H), 3.88-3.75 (m, 2H), 3.74-3.64 (m, 2H), 3.63-3.54 (m, 2H), 3.53-3.46 (m, 2H), 3.45-3.35 (m, 4H), 3.23-3.13 (m, 1H), 3.12-3.04 (m, 1H), 2.98-2.81 (m, 2H), 2.79-2.68 (m, 1H), 2.30-2.10 (m, 1H), 1.99-1.89 (m, 1H), 1.24 (d, J=6.1 Hz, 3H).

Example 22

5-[(4R,10aS)-8-[[5-[(3R,4R)-3-amino-4-methoxypyrrolidin-1-yl]-2-pyridyl]methyl]-4-methyl-1,3,4,6,7,9,10,10a-octahydropyrazino[1,2-d][1,4]diazepin-2-yl]quinoline-8-carbonitrile

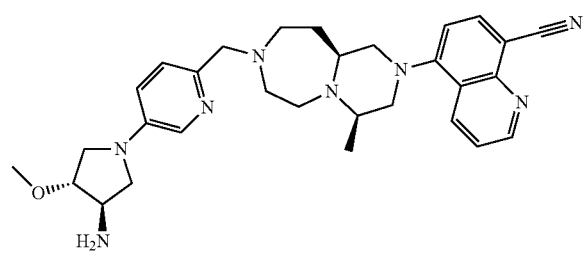 [SMILES: CO[C@@H]1CN(c2ccc(CN3CC[C@H]4CN(c5ccc(C#N)c6ncccc56)C[C@@H](C)N4CC3)nc2)C[C@H]1N]

The title compound was prepared in analogy to the preparation of Example 19 by using tert-butyl N-[(3R,4R)-4-methoxypyrrolidin-3-yl]carbamate (CAS: 1932066-52-8, PharmaBlock, Catalog: PBZ4728) instead of tert-butyl piperazine-1-carboxylate in step (b). Example 22 was obtained. MS: calc'd 527 [(M+H)$^+$], measured 527 [(M+H)$^+$]. $^1$H NMR (400 MHz, METHANOL-d$_4$) δ ppm 9.01-8.95 (m, 1H), 8.65-8.59 (m, 1H), 8.15 (d, J=8.1 Hz, 1H), 8.11 (d, J=2.9 Hz, 1H), 7.70-7.60 (m, 1H), 7.44 (d, J=8.6 Hz, 1H), 7.25 (d, J=8.1 Hz, 1H), 7.19-7.11 (m, 1H), 4.36 (s, 2H), 4.24-4.16 (m, 1H), 4.04-3.97 (m, 1H), 3.95-3.86 (m, 1H), 3.81-3.72 (m, 1H), 3.61-3.35 (m, 6H), 3.48 (s, 3H), 3.30-3.22 (m, 1H), 3.22-3.12 (m, 1H), 3.06-2.86 (m, 2H), 2.84-2.72 (m, 1H), 2.33-2.12 (m, 1H), 2.04-1.91 (m, 1H), 1.26 (d, J=6.2 Hz, 3H).

Example 23

5-[(4R,10aS)-8-[(3-fluoro-5-piperazin-1-yl-2-pyridyl)methyl]-4-methyl-1,3,4,6,7,9,10,10a-octahydropyrazino[1,2-d][1,4]diazepin-2-yl]quinoline-8-carbonitrile

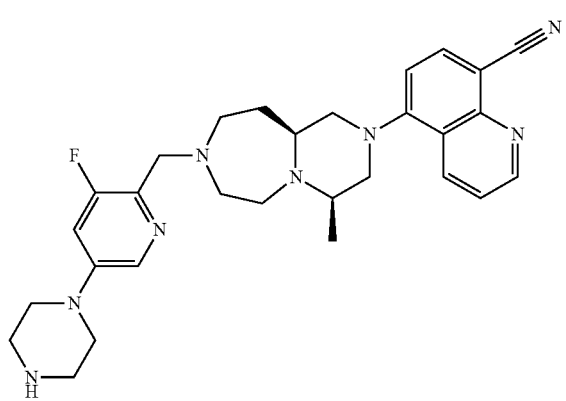 [SMILES: C[C@@H]1CN(c2ccc(C#N)c3ncccc23)C[C@@H]2CCN(Cc3ncc(N4CCNCC4)cc3F)CCN21]

The titled compound was synthesized according to the following scheme:

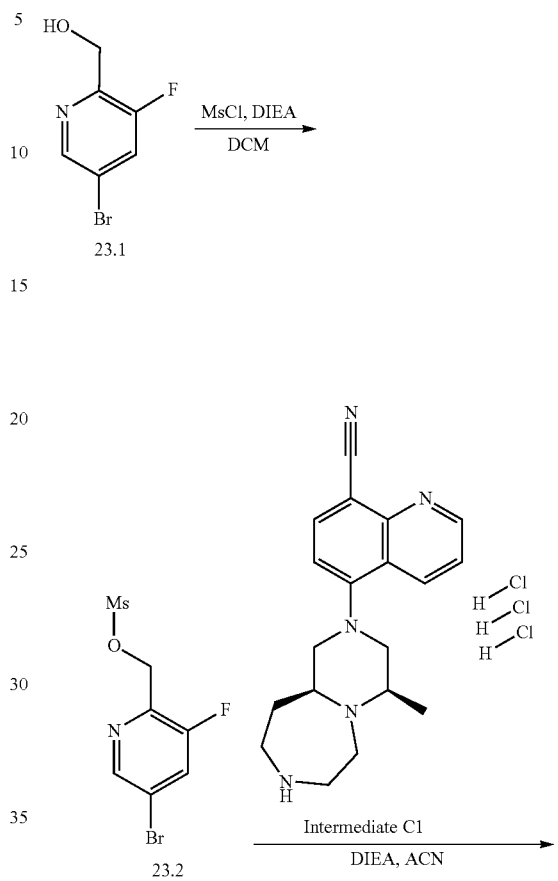

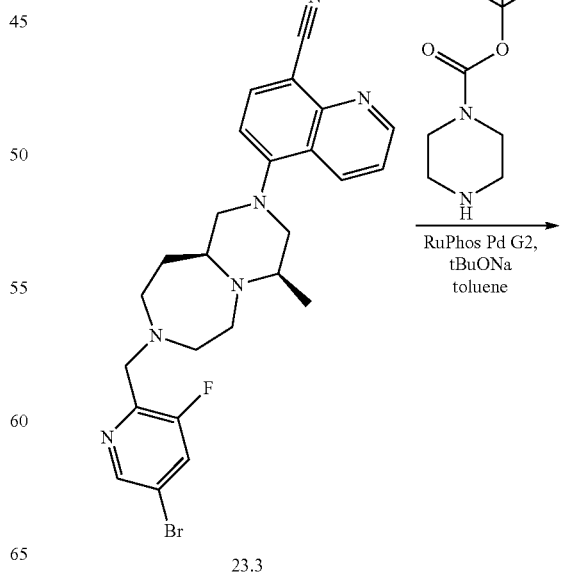

-continued

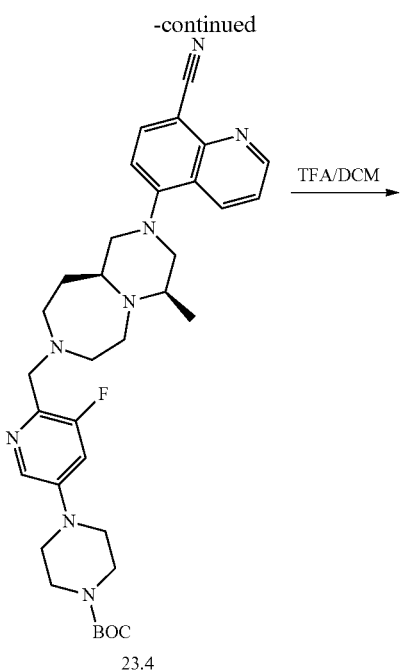

23.4

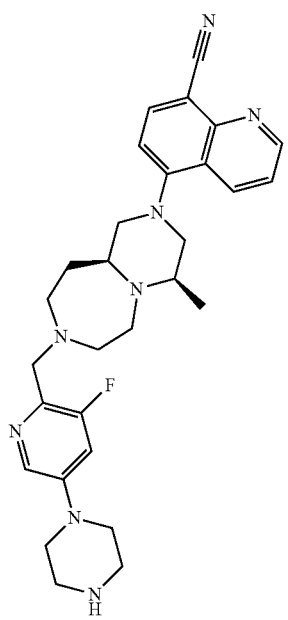

Example 23

Step (a): Preparation of (5-bromo-3-fluoro-2-pyridyl)methyl methanesulfonate (Compound 23.2)

To a solution of (5-bromo-3-fluoropyridin-2-yl)methanol (CAS: 1206968-92-4, BePharm, Catalog: BD264415, 300 mg, 1.46 mmol) and DIEA (565 mg, 4.37 mmol) in DCM (40 mL) was added dropwise methanesulfonyl chloride (183 mg, 1.6 mmol). The resultant mixture was stirred at room temperature for 2 hrs, then quenched with aq.NaHCO$_3$, extracted with DCM (20 mL) twice. The combined organic layer was washed with brine, dried over Na$_2$SO$_4$, filtered and the filtrate was concentrated to afford compound 23.2 (414 mg, 100% yield) which was used directly for the next step without further purification. MS: calc'd 284 [(M+H)$^+$], measured 284 [(M+H)$^+$].

Step (b): Preparation of 5-[(4R,10aS)-8-[(5-bromo-3-fluoro-2-pyridyl)methyl]-4-methyl-1,3,4,6,7,9,10,10a-octahydropyrazino[1,2-d][1,4]diazepin-2-yl]quinoline-8-carbonitrile (Compound 23.3)

To a solution of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1, 320 mg, 743 μmol) in acetonitrile (30 mL) was added (5-bromo-3-fluoropyridin-2-yl)methyl methanesulfonate (compound 23.2, 414 mg, 1.46 mmol) and DIEA (480 mg, 3.71 mmol). The resultant mixture was stirred at reflux for 5 hrs. The mixture was concentrated, the residue was purified by flash chromatography to afford compound 23.3 (220 mg, 58.1% yield). MS: calc'd 509,511 [(M+H)$^+$], measured 509,511 [(M+H)$^+$].

Step (c): Preparation of tert-butyl 4-[6-[[(4R,10aS)-2-(8-cyano-5-quinolyl)-4-methyl-1,3,4,6,7,9,10,10a-octahydropyrazino[1,2-d][1,4]diazepin-8-yl]methyl]-5-fluoro-3-pyridyl]piperazine-1-carboxylate (Compound 23.4)

To a solution of 5-[(4R,10aS)-8-[(5-bromo-3-fluoro-2-pyridyl)methyl]-4-methyl-1,3,4,6,7,9,10,10a-octahydropyrazino[1,2-d][1,4]diazepin-2-yl]quinoline-8-carbonitrile (compound 23.3, 45 mg, 88.3 μmol) in toluene (8 mL) was added tert-butyl piperazine-1-carboxylate (32.9 mg, 177 μmol), RuPhos Pd G2 (6.86 mg, 8.83 μmol) and tBuONa (17 mg, 177 μmol). The resultant mixture was stirred at 100° C. overnight. Then the mixture was cooled to room temperature, diluted with water (20 mL) and extracted with EA (20 mL) for three times. The combined organic layer was washed with brine, dried over Na$_2$SO$_4$, filtered and concentrated in vacuo. The residue was purified by flash chromatography to afford compound 23.4 (27 mg, 49.7% yield). 615 [(M+H)$^+$], measured 615 [(M+H)$^+$].

Step (d): Preparation of 5-[(4R,10aS)-8-[(3-fluoro-5-piperazin-1-yl-2-pyridyl)methyl]-4-methyl-1,3,4,6,7,9,10,10a-octahydropyrazino[1,2-d][1,4]diazepin-2-yl]quinoline-8-carbonitrile (Example 23)

To a solution of tert-butyl 4-[6-[[(4R,10aS)-2-(8-cyano-5-quinolyl)-4-methyl-1,3,4,6,7,9,10,10a-octahydropyrazino[1,2-d][1,4]diazepin-8-yl]methyl]-5-fluoro-3-pyridyl]piperazine-1-carboxylate (compound 23.4, 27 mg, 43.9 μmol) in DCM (8 mL) was added TFA (4 mL). The reaction mixture was stirred at room temperature for 2 hrs, then concentrated to afford a crude product, which was purified by pre-HPLC to afford Example 23 (20 mg, 88.6% yield). MS: calc'd 515 [(M+H)$^+$], measured 515 [(M+H)$^+$]. $^1$H NMR (400 MHz, METHANOL-d$_4$) δ ppm 9.09-8.94 (m, 1H), 8.68-8.60 (m, 1H), 8.33 (d, J=1.3 Hz, 1H), 8.16 (d, J=7.9 Hz, 1H), 7.70-7.61 (m, 1H), 7.42-7.35 (m, 1H), 7.26 (d, J=8.1 Hz, 1H), 4.45 (s, 2H), 3.67-3.52 (m, 6H), 3.52-3.36 (m, 9H), 3.29-3.21 (m, 1H), 3.20-3.07 (m, 1H), 3.03-2.84 (m, 2H), 2.82-2.66 (m, 1H), 2.31-2.11 (m, 1H), 2.03-1.84 (m, 1H), 1.26 (d, J=6.1 Hz, 3H).

Example 24

5-[(4R,10aS)-8-[[5-[(3R,4R)-3-amino-4-methoxy-pyrrolidin-1-yl]-3-fluoro-2-pyridyl]methyl]-4-methyl-1,3,4,6,7,9,10,10a-octahydropyrazino[1,2-d][1,4]diazepin-2-yl]quinoline-8-carbonitrile

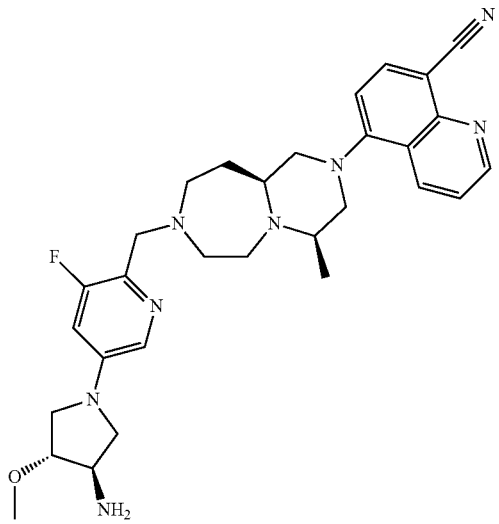 [SMILES: CO[C@@H]1CN(c2cnc(CN3CC[C@H]4CN(c5ccc(C#N)c6ncccc56)C[C@@H](C)N4CC3)c(F)c2)C[C@H]1N]

The title compound was prepared in analogy to the preparation of Example 23 by using tert-butyl N-[(3R,4R)-4-methoxypyrrolidin-3-yl]carbamate (CAS: 1932066-52-8, PharmaBlock, Catalog: PBZ4728) instead of tert-butyl piperazine-1-carboxylate in step (c). Example 24 was obtained. MS: calc'd 545 [(M+H)$^+$], measured 545 [(M+H)$^+$]. $^1$H NMR (400 MHz, METHANOL-d$_4$) δ ppm 9.03-8.96 (m, 1H), 8.65-8.59 (m, 1H), 8.16 (d, J=7.9 Hz, 1H), 7.98 (d, J=0.9 Hz, 1H), 7.68-7.61 (m, 1H), 7.25 (d, J=8.1 Hz, 1H), 7.00-6.94 (m, 1H), 4.43 (s, 2H), 4.22-4.14 (m, 1H), 4.03-3.95 (m, 1H), 3.94-3.85 (m, 1H), 3.83-3.76 (m, 1H), 3.66-3.36 (m, 6H), 3.51 (s, 3H), 3.25-3.17 (m, 1H), 3.13-3.07 (m, 1H), 2.99-2.84 (m, 2H), 2.80-2.68 (m, 1H), 2.30-2.13 (m, 1H), 2.00-1.86 (m, 1H), 1.24 (d, J=6.1 Hz, 3H).

Example 25

4-[(4R,10aS)-8-[[5-[(3R,4R)-3-amino-4-methoxy-pyrrolidin-1-yl]pyrazin-2-yl]methyl]-4-methyl-1,3,4,6,7,9,10,10a-octahydropyrazino[1,2-d][1,4]diazepin-2-yl]pyrazolo[1,5-a]pyridine-7-carbonitrile

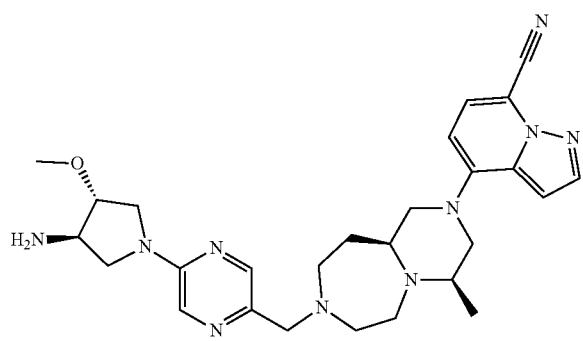 [SMILES: CO[C@@H]1CN(c2cnc(CN3CC[C@H]4CN(c5ccc(C#N)n6nccc56)C[C@@H](C)N4CC3)cn2)C[C@H]1N]

The title compound was prepared in analogy to the preparation of Example 15 by using 4-[(4R,10aS)-4-methyl-3,4,6,7,8,9,10,10a-octahydro-1H-pyrazino[1,2-d][1,4]diazepin-2-yl]pyrazolo[1,5-a]pyridine-7-carbonitrile;trihydrochloride (Intermediate C3) instead of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1) in step (a) and tert-butyl N-[(3R,4R)-4-methoxypyrrolidin-3-yl]carbamate instead of tert-butyl piperazine-1-carboxylate in step (b). Example 25 was obtained. MS: calc'd 517 [(M+H)$^+$], measured 517 [(M+H)$^+$]. $^1$H NMR (400 MHz, METHANOL-d$_4$) δ ppm 8.23 (d, J=1.3 Hz, 1H), 8.12 (d, J=1.3 Hz, 1H), 8.04 (d, J=2.4 Hz, 1H), 7.47 (d, J=7.9 Hz, 1H), 6.85 (d, J=2.4 Hz, 1H), 6.59 (d, J=8.1 Hz, 1H), 4.38 (s, 2H), 4.27-4.17 (m, 1H), 4.04-3.91 (m, 3H), 3.82-3.57 (m, 5H), 3.56-3.45 (m, 2H), 3.51 (s, 3H), 3.10-2.88 (m, 3H), 2.79-2.70 (m, 1H), 2.33-2.20 (m, 1H), 1.96 (br d, J=2.2 Hz, 1H), 1.24 (d, J=6.0 Hz, 3H).

Example 26

4-[(4R,10aS)-8-[[5-[(3R,4R)-3-amino-4-methoxy-pyrrolidin-1-yl]-3-fluoro-2-pyridyl]methyl]-4-methyl-1,3,4,6,7,9,10,10a-octahydropyrazino[1,2-d][1,4]diazepin-2-yl]pyrazolo[1,5-a]pyridine-7-carbonitrile The title compound was prepared in analogy to the preparation of Example 24 by using 4-[(4R,10aS)-4-methyl-3,4,6,7,8,9,10,10a-octahydro-1H-pyrazino[1,2-d][1,4]diazepin-2-yl]pyrazolo[1,5-a]pyridine-7-carbonitrile;trihydrochloride (Intermediate C3) instead of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1) in step (a). Example 26 was obtained. MS: calc'd 534 [(M+H)$^+$], measured 534 [(M+H)$^+$]. $^1$H NMR (400 MHz, METHANOL-d$_4$) δ ppm 7.91 (d, J=2.3 Hz, 1H), 7.72 (d, J=1.0 Hz, 1H), 7.34 (d, J=7.9 Hz, 1H), 6.76-6.67 (m, 2H), 6.45 (d, J=8.1 Hz, 1H), 3.95 (s, 2H), 3.87-3.76 (m, 1H), 3.70-3.63 (m, 1H), 3.62-3.54 (m, 2H), 3.55-3.46 (m, 1H), 3.33 (s, 3H), 3.19-2.86 (m, 5H), 2.81-2.65 (m, 3H), 2.64-2.55 (m, 2H), 2.04-1.92 (m, 1H), 1.77-1.67 (m, 1H), 1.08 (d, J=6.0 Hz, 3H).

Example 27

4-[(4R,10aS)-8-[[5-[(3R,4R)-3-amino-4-methoxy-pyrrolidin-1-yl]-3-fluoro-2-pyridyl]methyl]-4-methyl-1,3,4,6,7,9,10,10a-octahydropyrazino[1,2-d][1,4]diazepin-2-yl]-3-fluoro-pyrazolo[1,5-a]pyridine-7-carbonitrile

Example 28

4-[(4R,10aS)-4-methyl-8-(1,2,3,4-tetrahydroisoquinolin-7-ylmethyl)-1,3,4,6,7,9,10,10a-octahydropyrazino[1,2-d][1,4]diazepin-2-yl]-1-methyl-1,8-naphthyridin-2-one

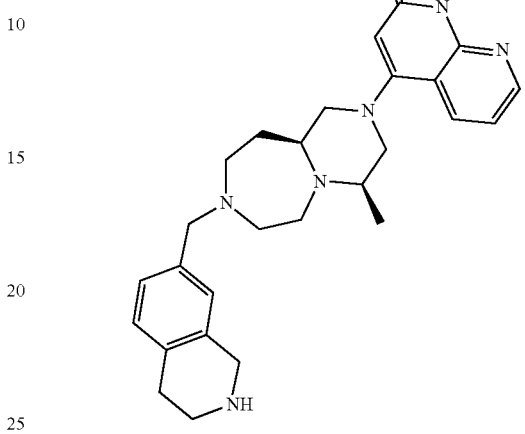

The title compound was prepared in analogy to the preparation of Example 12 by using 4-[(4R,10aS)-4-methyl-3,4,6,7,8,9,10,10a-octahydro-1H-pyrazino[1,2-d][1,4]diazepin-2-yl]-1-methyl-1,8-naphthyridin-2-one;trihydrochloride (Intermediate C2) instead of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1) in step (a). Example 28 was obtained. MS: calc'd 473 [(M+H)$^+$], measured 373 [(M+H)$^+$]. $^1$H NMR (400 MHz, METHANOL-d$_4$) δ ppm 8.66-8.57 (m, 1H), 8.22-8.13 (m, 1H), 7.32-7.25 (m, 1H), 7.16-6.95 (m, 3H), 6.09 (s, 1H), 3.96 (s, 2H), 3.74 (s, 3H), 3.59 (s, 2H), 3.23 (br d, J=11.9 Hz, 1H), 3.15-3.06 (m, 3H), 2.95-2.48 (m, 12H), 1.96-1.78 (m, 1H), 1.72 (br s, 1H), 1.13 (d, J=6.1 Hz, 3H).

Example 29

The following tests were carried out in order to determine the activity of the compounds of formula (I), (Ia) or (Ib) in HEK293-Blue-hTLR-7/8/9 cells assay.

HEK293-Blue-hTLR-7 Cells Assay:

A stable HEK293-Blue-hTLR-7 cell line was purchased from InvivoGen (Cat. #: hkb-htlr7, San Diego, California, USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was declined by TLR7 antagonist under the stimulation of a ligand, such as R848 (Resiquimod), for incubation of 20 hrs. The cell culture supernatant SEAP reporter activity was determined using QUANTI-Blue™ kit (Cat. #: rep-qb1, Invivogen, San Diego, Ca., USA) at a wavelength of 640 nm, a detection medium that turns purple or blue in the presence of alkaline phosphatase.

HEK293-Blue-hTLR7 cells were incubated at a density of 250,000-450,000 cells/mL in a volume of 170 μL in a 96-well plate in Dulbecco's Modified Eagle's medium

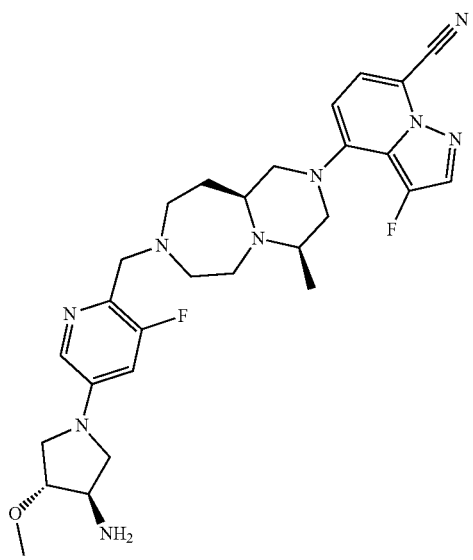 [SMILES: CO[C@@H]1CN(c2cnc(CN3CC[C@H]4CN(c5ccc(C#N)n6ncc(F)c56)C[C@@H](C)N4CC3)c(F)c2)C[C@H]1N]

The title compound was prepared in analogy to the preparation of Example 24 by using 4-[(4R,10aS)-4-methyl-3,4,6,7,8,9,10,10a-octahydro-1H-pyrazino[1,2-d][1,4]diazepin-2-yl]-3-fluoro-pyrazolo[1,5-a]pyridine-7-carbonitrile;trihydrochloride (Intermediate C4) instead of 5-[(4R,10aS)-4-methyl-3,4,6,7,8,9,10,10a-octahydro-1H-pyrazino[1,2-d][1,4]diazepin-2-yl]quinoline-8-carbonitrile;trihydrochloride (Intermediate C1) in step (a). Example 27 was obtained. MS: calc'd 552 [(M+H)$^+$], measured 552 [(M+H)$^+$]. $^1$H NMR (400 MHz, METHANOL-d$_4$) δ ppm 8.00 (d, J=3.7 Hz, 1H), 7.99-7.97 (m, 1H), 7.43 (d, J=8.1 Hz, 1H), 6.97 (s, 1H), 6.51 (d, J=8.1 Hz, 1H), 4.44 (s, 2H), 4.20-4.13 (m, 1H), 4.01-3.95 (m, 1H), 3.93-3.85 (m, 1H), 3.84-3.75 (m, 1H), 3.67-3.42 (m, 6H), 3.49 (s, 3H), 2.99 (br d, J=2.7 Hz, 1H), 2.95-2.78 (m, 3H), 2.74-2.61 (m, 1H), 2.30-2.17 (m, 1H), 2.02-1.91 (m, 1H), 1.23 (d, J=6.1 Hz, 3H).

(DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM R848 in above DMEM, perform incubation under 37° C. in a $CO_2$ incubator for 20 hrs. Then 20 μL of the supernatant from each well was incubated with 180 μL Quanti-blue substrate solution at 37° C. for 2 hrs and the absorbance was read at 620655 nm using a spectrophotometer. The signaling pathway that TLR7 activation leads to downstream NF-κB activation has been widely accepted, and therefore similar reporter assay was modified for evaluating TLR7 antagonist.

HEK293-Blue-hTLR-8 Cells Assay:

A stable HEK293-Blue-hTLR-8 cell line was purchased from InvivoGen (Cat. #: hkb-htlr8, San Diego, California, USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore the reporter expression was declined by TLR8 antagonist under the stimulation of a ligand, such as R848, for incubation of 20 hrs. The cell culture supernatant SEAP reporter activity was determined using QUANTI-Blue™ kit (Cat. #: rep-qb1, Invivogen, San Diego, Ca., USA) at a wavelength of 640 nm, a detection medium that turns purple or blue in the presence of alkaline phosphatase.

HEK293-Blue-hTLR8 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 60 uM R848 in above DMEM, perform incubation under 37° C. in a $CO_2$ incubator for 20 hrs. Then 20 μL of the supernatant from each well was incubated with 180 μL Quanti-blue substrate solution at 37° C. for 2 hrs and the absorbance was read at 620-655 nm using a spectrophotometer. The signaling pathway that TLR8 activation leads to downstream NF-κB activation has been widely accepted, and therefore similar reporter assay was modified for evaluating TLR8 antagonist.

HEK293-Blue-hTLR-9 Cells Assay:

A stable HEK293-Blue-hTLR-9 cell line was purchased from InvivoGen (Cat. #: hkb-htlr9, San Diego, California, USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR9 cells with TLR9 ligands. Therefore the reporter expression was declined by TLR9 antagonist under the stimulation of a ligand, such as ODN2006 (Cat. #: tlrl-2006-1, Invivogen, San Diego, California, USA), for incubation of 20 hrs. The cell culture supernatant SEAP reporter activity was determined using QUANTI-Blue™ kit (Cat. #: rep-qb1, Invivogen, San Diego, California, USA) at a wavelength of 640 nm, a detection medium that turns purple or blue in the presence of alkaline phosphatase.

HEK293-Blue-hTLR9 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM ODN2006 in above DMEM, perform incubation under 37° C. in a $CO_2$ incubator for 20 hrs. Then 20 μL of the supernatant from each well was incubated with 180 μL Quanti-blue substrate solution at 37° C. for 2 h and the absorbance was read at 620-655 nm using a spectrophotometer. The signaling pathway that TLR9 activation leads to downstream NF-κB activation has been widely accepted, and therefore similar reporter assay was modified for evaluating TLR9 antagonist.

The compounds of formula (I) have TLR7 and/or TLR8 inhibitory activities ($IC_{50}$ value) <0.1 μM. Moreover, most compounds also have TLR9 inhibitory activity <0.3 μM. Activity data of the compounds of the present invention were shown in Table 1.

TABLE 1

The activity of the compounds of present invention in HEK293-Blue-hTLR-7/8/9 cells assays

| Example No | HEK/hTLR7 $IC_{50}$ (nM) | HEK/hTLR8 $IC_{50}$ (nM) | HEK/hTLR9 $IC_{50}$ (nM) |
| --- | --- | --- | --- |
| 1 | 88.5 | 61.7 | 207.0 |
| 2 | 58.6 | 25.2 | 59.3 |
| 3 | 54.0 | 4.8 | 52.0 |
| 4 | 17.8 | 2.4 | <31.8 |
| 5 | 38.5 | 3.9 | 72.1 |
| 6 | 48.1 | <3.2 | 100.7 |
| 7 | 61.3 | 1.5 | 81.9 |
| 8 | 14.3 | 8.6 | 62.2 |
| 9 | 8.2 | 6.4 | 35.0 |
| 10 | 9.3 | 5.2 | <31.8 |
| 11 | 6.1 | 4.2 | 48.7 |
| 12 | 4.5 | 2.7 | 43.8 |
| 13 | 49.6 | 31.7 | 96.4 |
| 14 | 1.8 | 4.9 | 70.5 |
| 15 | 2.2 | 8.6 | 36.1 |
| 16 | 11.1 | 12.1 | 35.4 |
| 17 | 1.2 | 3.4 | <31.8 |
| 18 | 12.1 | 8.1 | <31.8 |
| 19 | 4.8 | 10.2 | 45.8 |
| 20 | 1.6 | 11.0 | 34.9 |
| 21 | 59.9 | 86.9 | 104.8 |
| 22 | 4.9 | 14.1 | 62.8 |
| 23 | 2.9 | 8.3 | 39.1 |
| 24 | 3.2 | 7.9 | 60.9 |
| 26 | 35.8 | 85.7 | 87.4 |
| 27 | 8.5 | 10.1 | 65.4 |
| 28 | 36.3 | 51.1 | <31.8 |

Example 30

Human Microsomal Stability Assay

Human liver microsomes (Cat. NO.: 452117, Corning, USA) were preincubated with test compound for 10 minutes at 37° C. in 100 mM potassium phosphate buffer, pH 7.4. The reactions were initiated by adding NADPH regenerating system. The final incubation mixtures contained 1 μM test compound, 0.5 mg/mL liver microsomal protein, 1 mM $MgCl_2$, 1 mM NADP, 1 unit/mL isocitric dehydrogenase and 6 mM isocitric acid in 100 mM potassium phosphate buffer, pH 7.4. After incubation times of 0, 3, 6, 9, 15 and 30 minutes at 37° C., 300 μL of cold ACN (including internal standard) was added to 100 μL incubation mixture to terminate the reaction. Following precipitation and centrifugation, 100 uL supernatant will be taken out and added 300 uL water. The amount of compound remaining in the samples was determined by LC-MS/MS. Controls of no NADPH regenerating system at zero and 30 minutes were also prepared and analyzed. The results were categorized as: low (<7.0 mL/min/kg), medium (7.0-16.2 mL/min/kg) and high (16.2-23.2 mL/min/kg). Test results were summarized in Table 2.

TABLE 2

Human microsomal stability results

| Example No | CL (h) (mL/min/kg) |
| --- | --- |
| 11 | 8.2 |
| 14 | 9.8 |
| 15 | 9.9 |
| 17 | 9.2 |
| 21 | 8.5 |
| 23 | 8.8 |
| 24 | 9.4 |
| 28 | 6.5 |

Example 31 hERG Channel Inhibition Assay

The hERG channel inhibition assay is a highly sensitive measurement that identifies compounds exhibiting hERG inhibition related to cardiotoxicity in vivo. The hERG K+ channels were cloned in humans and stably expressed in a CHO (Chinese hamster ovary) cell line. CHO$_{hERG}$ cells were used for patch-clamp (voltage-clamp, whole-cell) experiments. Cells were stimulated by a voltage pattern to activate hERG channels and conduct I$_{KhERG}$ currents (rapid delayed outward rectifier potassium current of the hERG channel). After the cells were stabilized for a few minutes, the amplitude and kinetics of I$_{KhERG}$ were recorded at a stimulation frequency of 0.1 Hz (6 bpm). Thereafter, the test compound was added to the preparation at increasing concentrations. For each concentration, an attempt was made to reach a steady-state effect, usually, this was achieved within 3-10 min at which time the next highest concentration was applied. The amplitude and kinetics of I$_{KhERG}$ are recorded in each concentration of the drug which were compared to the control values (taken as 100%). (references: Redfern W S, Carlsson L, Davis A S, Lynch W G, MacKenzie I, Palethorpe S, Siegl P K, Strang I, Sullivan A T, Wallis R, Camm A J, Hammond T G. 2003; Relationships between preclinical cardiac electrophysiology, clinical QT interval prolongation and torsade de pointes for a broad range of drugs: evidence for a provisional safety margin in drug development. Cardiovasc. Res. 58:32-45, Sanguinetti M C, Tristani-Firouzi M. 2006; hERG potassium channels and cardiac arrhythmia. Nature 440:463-469, Webster R, Leishman D, Walker D. 2002; Towards a drug concentration effect relationship for QT prolongation and torsades de pointes. Curr. Opin. Drug Discov. Devel. 5:116-26). Results of hERG are given in Table 3.

TABLE 3 hERG results

| Example No | hERG IC$_{20}$ (µM) | hERG IC$_{50}$ (µM) |
| --- | --- | --- |
| 7 | >10 | >20 |
| 10 | >10 | >20 |
| 15 | >10 | >20 |

The invention claimed is:
1. A compound of formula (I),

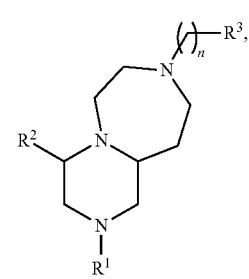

wherein
R$^1$ is

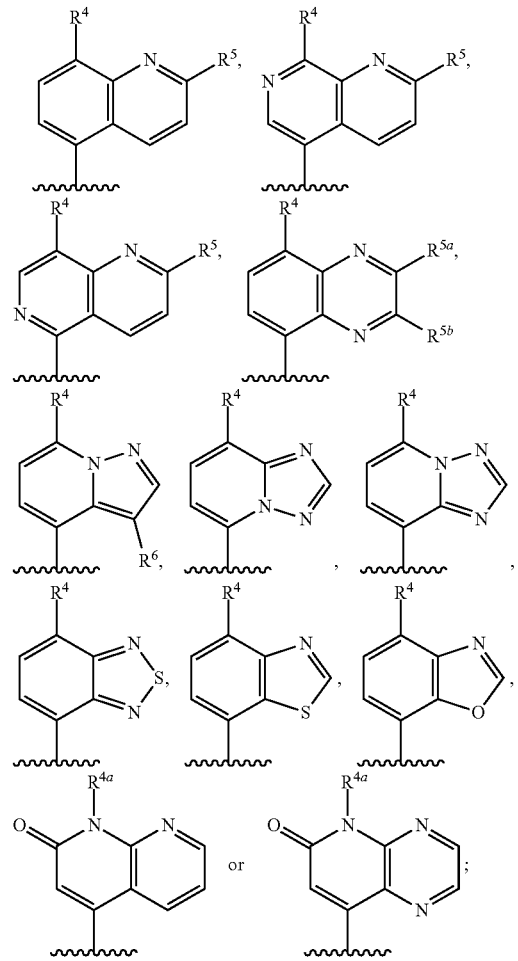

wherein R⁴ is C₁₋₆alkyl, C₁₋₆alkoxy, haloC₁₋₆alkyl, halogen, nitro or cyano; R⁴ᵃ is C₁₋₆alkyl or C₃₋₇cycloalkyl; R⁵, R⁵ᵃ and R⁵ᵇ are independently selected from H and deuterium; and R⁶ is H or halogen;
R² is C₁₋₆alkyl;
R³ is a 5-7 membered monocyclic aryl or heteroaryl; or a 7-12 membered bicyclic heterocyclyl; and
n is 0, 1 or 2;
or a pharmaceutically acceptable salt thereof.

2. A compound according to claim 1, or a pharmaceutically acceptable salt thereof, wherein
R³ is 1,2,3,4-tetrahydroisoquinolinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl;
5,6,7,8-tetrahydro-2,7-naphthyridinyl;
phenyl substituted by morpholinyl;
pyrazinyl substituted by piperazinyl;
pyridinyl which is substituted by one or two substituents independently selected from halogen, piperazinyl, aminohalopyrrolidinyl, amino-1,4-oxazepanyl and amino (C₁₋₆alkoxy) pyrrolidinyl; or
pyrimidinyl substituted by piperazinyl or amino (C₁₋₆alkoxy) pyrrolidinyl.

3. A compound according to claim 1, wherein R¹ is

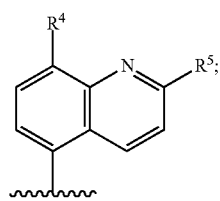

wherein R⁴ is cyano; and R⁵ is H;
R² is C₁₋₆alkyl;
R³ is 5,6,7,8-tetrahydro-2,6-naphthyridinyl; 5,6,7,8-tetrahydro-2,7-naphthyridinyl; pyridinyl substituted by amino (C₁₋₆alkoxy) pyrrolidinyl; or pyrimidinyl substituted by piperazinyl; and
n is 0 or 1;
or a pharmaceutically acceptable salt thereof.

4. A compound according to claim 3, wherein R¹ is

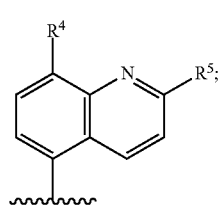

wherein R⁴ is cyano; and R⁵ is H;
R² is methyl;
R³ is 5,6,7,8-tetrahydro-2,7-naphthyridin-4-yl; 5,6,7,8-tetrahydro-2,6-naphthyridin-3-yl; piperazin-1-ylpyrimidinyl; or 3-amino-4-methoxy-pyrrolidin-1-ylpyridinyl; and
n is 0 or 1;
or a pharmaceutically acceptable salt thereof.

5. A process for the preparation of a compound according to claim 1, comprising any one of the following steps:

a) Buchwald-Hartwig amination reaction or nucleophilic substitution between compound of formula (IX),

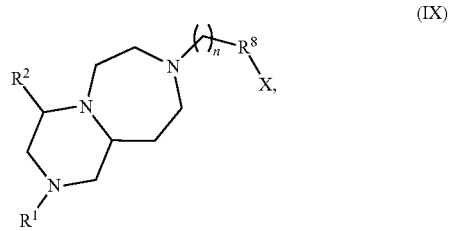

(IX)

and amine (X),

(X)

b) Buchwald-Hartwig amination reaction or nucleophilic substitution between compound of formula (V),

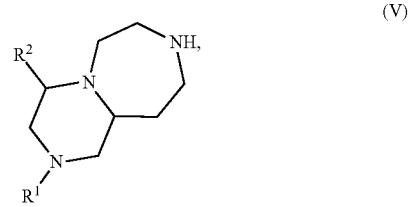

(V)

and compound of formula (VI),

(VI)

wherein R¹ and R² are as defined in claim 1; n is 0, 1 or 2; X is halogen; Y is halogen or methanesulfonate; R⁷ and R⁸ is aryl or heteroaryl; and R⁹ and R¹⁰ together with the nitrogen atom they are attached to form a heterocyclyl.

6. A pharmaceutical composition comprising a compound in accordance with claim 1, or a pharmaceutically acceptable salt thereof, and a therapeutically inert carrier.

7. A method for the treatment of systemic lupus erythematosus or lupus nephritis in a mammal in need thereof, which method comprises administering a therapeutically effective amount of a compound according to claim 1, or a pharmaceutically acceptable salt thereof, to said mammal.

8. A compound of formula (Ia),

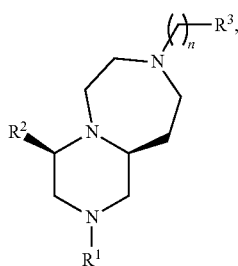

wherein
R¹ is

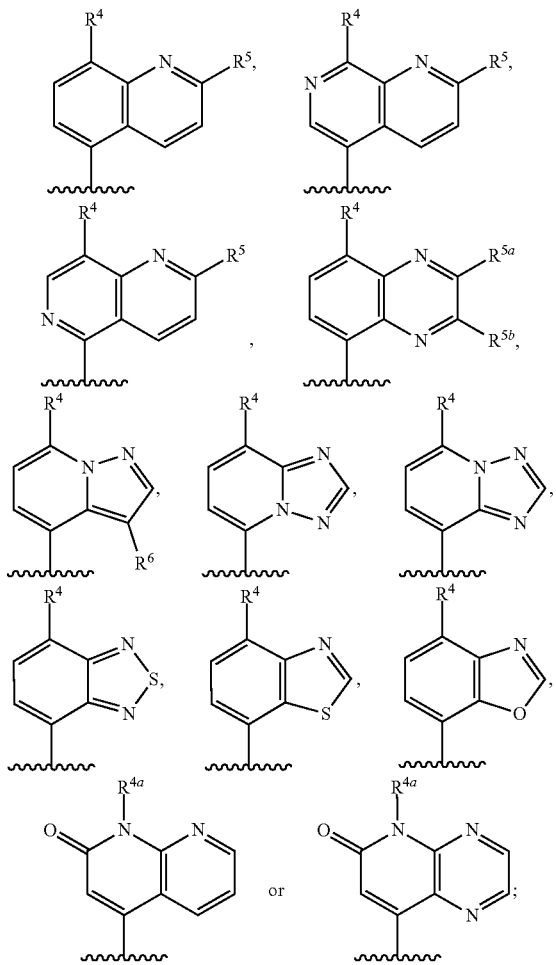

wherein R⁴ is $C_{1-6}$alkyl, $C_{1-6}$alkoxy, halo$C_{1-6}$alkyl, halogen, nitro or cyano; R⁴ᵃ is $C_{1-6}$alkyl or $C_{3-7}$cycloalkyl; R⁵, R⁵ᵃ and R⁵ᵇ are independently selected from H and deuterium; and R⁶ is H or halogen;
R² is $C_{1-6}$alkyl;
R³ is 1,2,3,4-tetrahydroisoquinolinyl;
5,6,7,8-tetrahydro-1,6-naphthyridinyl;
5,6,7,8-tetrahydro-1,7-naphthyridinyl;
5,6,7,8-tetrahydro-2,6-naphthyridinyl;
5,6,7,8-tetrahydro-2,7-naphthyridinyl;

phenyl substituted by morpholinyl;
pyrazinyl substituted by piperazinyl;
pyridinyl which is substituted by one or two substituents independently selected from halogen, piperazinyl, aminohalopyrrolidinyl, amino-1,4-oxazepanyl and amino ($C_{1-6}$alkoxy) pyrrolidinyl; or
pyrimidinyl substituted by piperazinyl or amino ($C_{1-6}$alkoxy) pyrrolidinyl; and
n is 0, 1 or 2;
or a pharmaceutically acceptable salt thereof.

9. A compound according to claim 8, or a pharmaceutically acceptable salt thereof, wherein
R¹ is

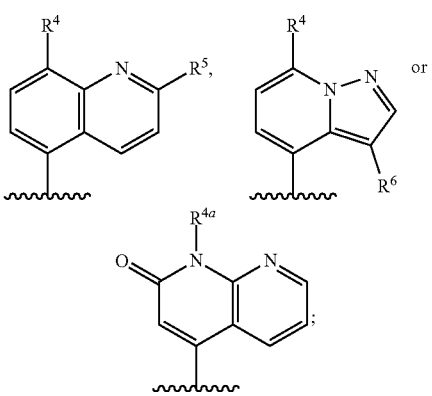

wherein R⁴ is cyano; R⁴ᵃ is $C_{1-6}$alkyl; R⁵ is H; and R⁶ is H or halogen; and
n is 0 or 1.

10. A compound according to claim 9, wherein
R¹ is

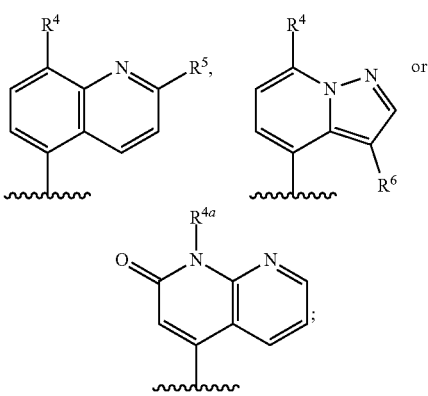

wherein R⁴ is cyano; R⁴ᵃ is methyl; R⁵ is H; and R⁶ is H or fluoro;
R² is methyl;
R³ is 1,2,3,4-tetrahydroisoquinolin-6-yl;
1,2,3,4-tetrahydroisoquinolin-7-yl;
5,6,7,8-tetrahydro-1,6-naphthyridin-2-yl;
5,6,7,8-tetrahydro-1,6-naphthyridin-3-yl;
5,6,7,8-tetrahydro-1,7-naphthyridin-2-yl;
5,6,7,8-tetrahydro-2,6-naphthyridin-3-yl;
5,6,7,8-tetrahydro-2,7-naphthyridin-3-yl;
5,6,7,8-tetrahydro-2,7-naphthyridin-4-yl;
morpholin-2-ylphenyl;
piperazin-1-ylpyrazinyl;

pyridinyl which is substituted by one or two substituents independently selected from fluoro, piperazin-1-yl, 3-amino-4-fluoro-pyrrolidin-1-yl, 6-amino-1,4-oxazepan-4-yl and 3-amino-4-methoxy-pyrrolidin-1-yl; or pyrimidinyl substituted by piperazin-1-yl or 3-amino-4-methoxy-pyrrolidin-1-yl; and n is 0 or 1;

or a pharmaceutically acceptable salt thereof.

11. A compound according to claim 9, or a pharmaceutically acceptable salt thereof, wherein $R^1$ is

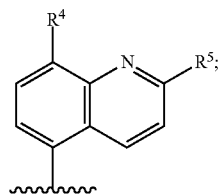

wherein $R^4$ is cyano; and $R^5$ is H.

12. A compound according to claim 11, or a pharmaceutically acceptable salt thereof, wherein $R^3$ is 5,6,7,8-tetrahydro-2,6-naphthyridinyl; 5,6,7,8-tetrahydro-2,7-naphthyridinyl; pyridinyl substituted by amino ($C_{1-6}$alkoxy) pyrrolidinyl; or pyrimidinyl substituted by piperazinyl.

13. A compound according to claim 12, or a pharmaceutically acceptable salt thereof, wherein $R^3$ is 5,6,7,8-tetrahydro-2,7-naphthyridin-4-yl; 5,6,7,8-tetrahydro-2,6-naphthyridin-3-yl; piperazin-1-ylpyrimidinyl; or 3-amino-4-methoxy-pyrrolidin-1-ylpyridinyl.

14. A compound selected from:
5-[(4R,10aS)-4-methyl-8-(6-piperazin-1-yl-3-pyridyl)-1,3,4,6,7,9,10,10a-octahydropyrazino [1,2-d][1,4]diazepin-2-yl]quinoline-8-carbonitrile;
5-[(4R,10aS)-4-methyl-8-(2-piperazin-1-ylpyrimidin-5-yl)-1,3,4,6,7,9,10,10a-octahydropyrazino [1,2-d][1,4]diazepin-2-yl]quinoline-8-carbonitrile;
5-[(4R,10aS)-4-methyl-8-[4-[(2S)-morpholin-2-yl]phenyl]-1,3,4,6, 7,9,10,10a-octahydropyrazino [1,2-d][1,4]diazepin-2-yl]quinoline-8-carbonitrile;
5-[(4R,10aS)-4-methyl-8-(5,6,7,8-tetrahydro-2,7-naphthyridin-4-yl)-1,3,4,6,7,9,10,10a-octahydropyrazino [1,2-d][1,4]diazepin-2-yl]quinoline-8-carbonitrile;
5-[(4R,10aS)-4-methyl-8-(5,6,7,8-tetrahydro-1,7-naphthyridin-2-yl)-1,3,4,6,7,9,10,10a-octahydropyrazino [1,2-d][1,4]diazepin-2-yl]quinoline-8-carbonitrile;
5-[(4R,10aS)-4-methyl-8-(5,6,7,8-tetrahydro-1,6-naphthyridin-2-yl)-1,3,4,6,7,9,10,10a-octahydropyrazino [1,2-d][1,4]diazepin-2-yl]quinoline-8-carbonitrile;
5-[(4R,10aS)-4-methyl-8-(5,6,7,8-tetrahydro-2,7-naphthyridin-3-yl)-1,3,4,6,7,9,10,10a-octahydropyrazino [1,2-d][1,4]diazepin-2-yl]quinoline-8-carbonitrile;
5-[(4R,10aS)-4-methyl-8-(5,6,7,8-tetrahydro-2,7-naphthyridin-3-ylmethyl)-1,3,4,6,7,9,10, 10a-octahydropyrazino [1,2-d][1,4]diazepin-2-yl]quinoline-8-carbonitrile;
5-[(4R,10aS)-4-methyl-8-(5,6,7,8-tetrahydro-2,6-naphthyridin-3-ylmethyl)-1,3,4,6,7,9,10,10a-octahydropyrazino [1,2-d][1,4]diazepin-2-yl]quinoline-8-carbonitrile;
5-[(4R,10aS)-4-methyl-8-(5,6,7,8-tetrahydro-1,6-naphthyridin-3-ylmethyl)-1,3,4,6,7,9,10,10a-octahydropyrazino [1,2-d][1,4]diazepin-2-yl]quinoline-8-carbonitrile;
5-[(4R,10aS)-4-methyl-8-(1,2,3,4-tetrahydroisoquinolin-6-ylmethyl)-1,3,4,6,7,9,10,10a-octahydropyrazino [1,2-d][1,4]diazepin-2-yl]quinoline-8-carbonitrile;
5-[(4R,10aS)-4-methyl-8-(1,2,3,4-tetrahydroisoquinolin-7-ylmethyl)-1,3,4,6,7,9,10,10a-octahydropyrazino [1,2-d][1,4]diazepin-2-yl]quinoline-8-carbonitrile;
5-[(4R,10aS)-4-methyl-8-[(5-piperazin-1-ylpyrimidin-2-yl)methyl]-1,3,4,6,7,9,10,10a-octahydropyrazino [1,2-d][1,4]diazepin-2-yl]quinoline-8-carbonitrile;
5-[(4R,10aS)-4-methyl-8-[(2-piperazin-1-ylpyrimidin-5-yl)methyl]-1,3,4,6,7,9,10,10a-octahydropyrazino [1,2-d][1,4]diazepin-2-yl]quinoline-8-carbonitrile;
5-[(4R,10aS)-4-methyl-8-[(5-piperazin-1-ylpyrazin-2-yl)methyl]-1,3,4,6,7,9,10,10a-octahydropyrazino [1,2-d][1,4]diazepin-2-yl]quinoline-8-carbonitrile;
5-[(4R,10aS)-4-methyl-8-[(5-piperazin-1-yl-3-pyridyl)methyl]-1,3,4,6,7,9,10,10a-octahydropyrazino [1,2-d][1,4]diazepin-2-yl]quinoline-8-carbonitrile;
5-[(4R,10aS)-4-methyl-8-[(6-piperazin-1-yl-3-pyridyl)methyl]-1,3,4,6,7,9,10,10a-octahydropyrazino [1,2-d][1,4]diazepin-2-yl]quinoline-8-carbonitrile;
5-[(4R,10aS)-4-methyl-8-[(6-piperazin-1-yl-2-pyridyl)methyl]-1,3,4,6,7,9,10,10a-octahydropyrazino [1,2-d][1,4]diazepin-2-yl]quinoline-8-carbonitrile;
5-[(4R,10aS)-4-methyl-8-[(5-piperazin-1-yl-2-pyridyl)methyl]-1,3,4,6,7,9, 10,10a-octahydropyrazino [1,2-d][1,4]diazepin-2-yl]quinoline-8-carbonitrile;
5-[(4R,10aS)-8-[[5-[(3R,4S)-3-amino-4-fluoro-pyrrolidin-1-yl]-2-pyridyl]methyl]-4-methyl-1,3,4,6,7,9,10,10a-octahydropyrazino [1,2-d][1,4]diazepin-2-yl]quinoline-8-carbonitrile;
5-[(4R,10aS)-8-[5-[(6R)-6-amino-1,4-oxazepan-4-yl]-2-pyridyl]methyl]-4-methyl-1,3,4,6,7,9,10,10a-octahydropyrazino [1,2-d][1,4]diazepin-2-yl]quinoline-8-carbonitrile;
5-[(4R,10aS)-8-[[5-[(3R,4R)-3-amino-4-methoxy-pyrrolidin-1-yl]-2-pyridyl]methyl]-4-methyl-1,3,4,6,7,9,10,10a-octahydropyrazino [1,2-d][1,4]diazepin-2-yl]quinoline-8-carbonitrile;
5-[(4R,10aS)-8-[(3-fluoro-5-piperazin-1-yl-2-pyridyl)methyl]-4-methyl-1,3,4,6,7,9,10,10a-octahydropyrazino [1,2-d][1,4]diazepin-2-yl]quinoline-8-carbonitrile;
5-[(4R,10aS)-8-[5-[(3R,4R)-3-amino-4-methoxy-pyrrolidin-1-yl]-3-fluoro-2-pyridyl]methyl]-4-methyl-1,3,4,6,7,9,10,10a-octahydropyrazino [1,2-d][1,4]diazepin-2-yl]quinoline-8-carbonitrile;
4-[(4R,10aS)-8-[5-[(3R,4R)-3-amino-4-methoxy-pyrrolidin-1-yl]pyrazin-2-yl]methyl]-4-methyl-1,3,4,6,7,9,10,10a-octahydropyrazino [1,2-d][1,4]diazepin-2-yl]pyrazolo[1,5-a]pyridine-7-carbonitrile;
4-[(4R,10aS)-8-[5-[(3R,4R)-3-amino-4-methoxy-pyrrolidin-1-yl]-3-fluoro-2-pyridyl]methyl]-4-methyl-1,3,4,6,7,9,10,10a-octahydropyrazino [1,2-d][1,4]diazepin-2-yl]pyrazolo[1,5-a]pyridine-7-carbonitrile;
4-[(4R,10aS)-8-[5-[(3R,4R)-3-amino-4-methoxy-pyrrolidin-1-yl]-3-fluoro-2-pyridyl]methyl]-4-methyl-1,3,4,6,7,9,10,10a-octahydropyrazino [1,2-d][1,4]diazepin-2-yl]-3-fluoro-pyrazolo[1,5-a]pyridine-7-carbonitrile; and
4-[(4R,10aS)-4-methyl-8-(1,2,3,4-tetrahydroisoquinolin-7-ylmethyl)-1,3,4,6,7,9,10,10a-octahydropyrazino [1,2-d][1,4]diazepin-2-yl]-1-methyl-1,8-naphthyridin-2-one;

or a pharmaceutically acceptable salt thereof.

15. A pharmaceutical composition comprising a compound in accordance with claim 14, or a pharmaceutically acceptable salt thereof, and a therapeutically inert carrier.

16. A method for the treatment of systemic lupus erythematosus or lupus nephritis in a mammal in need thereof, which method comprises administering a therapeutically effective amount of a compound according to claim 14, or a pharmaceutically acceptable salt thereof, to said mammal.

* * * * *